United States Patent
Jeanmart et al.

(10) Patent No.: US 10,662,182 B2
(45) Date of Patent: May 26, 2020

(54) MICROBIOCIDAL THIAZOLE DERIVATIVES

(71) Applicant: SYNGENTA PARTICIPATIONS AG, Basel (CH)

(72) Inventors: Stephane André Marie Jeanmart, Stein (CH); Werner Zambach, Stein (CH); Stefano Rendine, Stein (CH); Clemens Lamberth, Stein (CN); Renaud Beaudegnies, Stein (CH); Martin Pouliot, Stein (CH); Damien Bonvalot, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 16/305,452

(22) PCT Filed: May 23, 2017

(86) PCT No.: PCT/EP2017/062443
§ 371 (c)(1),
(2) Date: Nov. 29, 2018

(87) PCT Pub. No.: WO2017/207362
PCT Pub. Date: Dec. 7, 2017

(65) Prior Publication Data
US 2019/0330168 A1    Oct. 31, 2019

(30) Foreign Application Priority Data
May 30, 2016    (EP) .................................... 16171966

(51) Int. Cl.
| C07D 417/12 | (2006.01) |
| C07D 417/14 | (2006.01) |
| A01N 43/78 | (2006.01) |
| C07D 277/56 | (2006.01) |

(52) U.S. Cl.
CPC .......... *C07D 417/12* (2013.01); *A01N 43/78* (2013.01); *C07D 277/56* (2013.01); *C07D 417/14* (2013.01)

(58) Field of Classification Search
CPC ........................... C07D 417/12; C07D 417/14
See application file for complete search history.

(56) References Cited

FOREIGN PATENT DOCUMENTS

| WO | 2010/012793 A1 | 2/2010 | |
| WO | WO-2010012793 A1 * | 2/2010 | ............. A01N 43/78 |

OTHER PUBLICATIONS

International Search Report and Written Opinion for International Patent Application No. PCT/EP2017/062443 dated Jul. 19, 2017.

* cited by examiner

*Primary Examiner* — Matthew P Coughlin
(74) *Attorney, Agent, or Firm* — Baker & Hostetler, LLP; Toni-Junell Herbert

(57) ABSTRACT

Compounds of the formula (I): wherein the substituents are as defined in claim 1, useful as pesticides, and especially fungicides.

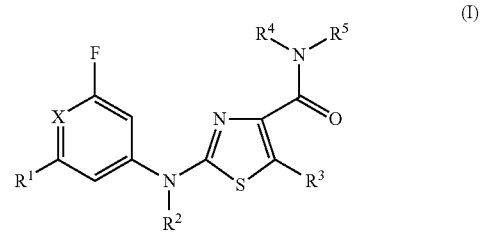

19 Claims, No Drawings

MICROBIOCIDAL THIAZOLE DERIVATIVES

CROSS-REFERENCE TO RELATED APPLICATIONS

This application is a 371 National Stage application of International Application No. PCT/EP2017/062443, filed May 23, 2017, the entire contents of which is hereby incorporated by reference, which claims priority to European Patent Application No. 16171966.1 filed May 30, 2016.

The present invention relates to microbiocidal thiazole derivatives, e.g., as active ingredients, which have microbiocidal activity, in particular fungicidal activity. The invention also relates to the preparation of these thiazole derivatives, to agrochemical compositions which comprise at least one of the thiazole derivatives and to uses of the thiazole derivatives or compositions thereof in agriculture or horticulture for controlling or preventing the infestation of plants, harvested food crops, seeds or non-living materials by phytopathogenic microorganisms, preferably fungi.

WO 2010/012793 describes amino-thiazole derivatives as pesticidal agents.

According to the present invention, there is provided a compound of formula (I):

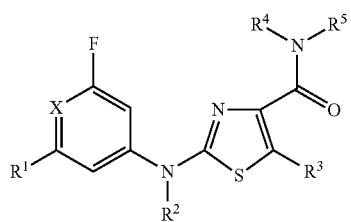

wherein, $R^1$ is halogen, cyano, $C_1$-$C_6$alkyl or $C_1$-$C_6$alkoxy, wherein $C_1$-$C_6$alkyl and $C_1$-$C_6$alkoxy are optionally substituted with 1 to 3 groups represented by $R^6$;

$R^2$ and $R^4$ are independently hydrogen, $C_1$-$C_6$alkyl, $C_1$-$C_6$alkoxy or $C_3$-$C_6$cycloalkyl, wherein $C_1$-$C_6$alkyl, $C_1$-$C_6$alkoxy and $C_3$-$C_6$cycloalkyl are optionally substituted with 1 to 3 groups represented by $R^6$;

$R^3$ is halogen, $C_1$-$C_6$alkyl, $C_1$-$C_6$alkoxy or $C_3$-$C_6$cycloalkyl, wherein $C_1$-$C_6$alkyl, $C_1$-$C_6$alkoxy and $C_3$-$C_6$cycloalkyl are optionally substituted with 1 to 3 groups represented by $R^6$;

$R^5$ is $C_1$-$C_{10}$alkyl, $C_3$-$C_{10}$cycloalkyl, $C_3$-$C_{10}$cycloalkenyl, $C_3$-$C_{10}$cycloalkyl$C_1$-$C_2$alkyl, $C_2$-$C_{10}$alkenyl, $C_2$-$C_{10}$alkynyl, aryl, heteroaryl wherein the heteroaryl is a 5- or 6-membered aromatic monocyclic ring comprising 1, 2, 3 or 4 heteroatoms individually selected from nitrogen, oxygen and sulfur, heterocyclyl wherein the heterocyclyl is a 4-, 5- or 6-membered non-aromatic monocyclic ring comprising 1, 2 or 3 heteroatoms individually selected from nitrogen, oxygen and sulfur, heterocyclyl$C_1$-$C_2$alkyl, or a 5- to 10-membered non-aromatic annulated or spirocyclic carbobicyclyl ring system optionally comprising 1, 2, 3, 4 or 5 heteroatoms individually selected from nitrogen, oxygen and sulfur, and optionally bonded to the rest of the molecule through a $C_1$-$C_2$alkylene linker;

wherein any of said $C_1$-$C_{10}$alkyl, $C_3$-$C_{10}$cycloalkyl, $C_3$-$C_{10}$cycloalkenyl, $C_2$-$C_{10}$alkenyl and $C_2$-$C_{10}$alkynyl moieties are optionally substituted with 1 to 4 groups represented by $R^7$ or 1 group represented by $R^8$; or wherein any of said aryl, heteroaryl and heterocyclyl moieties are optionally substituted with 1 to 3 groups represented by $R^9$ or 1 group represented by $R^{10}$, or are optionally substituted with 1 or 2 groups represented by $R^9$ and 1 group represented by $R^{10}$; or wherein the annulated or spirocyclic carbobicyclyl ring system is optionally substituted with 1 to 3 groups represented by $R^7$, or the annulated carbobicyclyl ring system is optionally substituted by $C_3$-$C_6$cycloalkyl to form a spirocyclyl moiety;

$R^6$ is independently selected from halogen, cyano, hydroxyl, $C_1$-$C_6$alkoxy, and $C_3$-$C_6$cycloalkyl;

$R^7$ is independently selected from halogen, cyano, hydroxyl, $C_1$-$C_6$alkyl, $C_1$-$C_6$haloalkyl, $C_1$-$C_6$alkoxy, $C_1$-$C_6$alkoxy$C_1$-$C_6$alkyl, $C_3$-$C_6$cycloalkyl, $C_3$-$C_6$cycloalkyl$C_{1-2}$alkyl, $C_2$-$C_6$acyl, $C_2$-$C_6$acyloxy, $C_2$-$C_6$acyloxy$C_1$-$C_6$alkyl and $C_1$-$C_4$alkoxycarbonyl;

wherein when $R^7$ is $C_3$-$C_6$cycloalkyl$C_{1-2}$alkyl, the $C_3$-$C_6$cycloalkyl moiety is optionally substituted with 1 or 2 groups independently selected from halogen and $C_1$-$C_6$alkyl;

$R^8$ is aryl, aryloxy, aryl$C_1$-$C_6$alkyl, heteroaryl wherein the heteroaryl is a 5- or 6-membered aromatic monocyclic ring comprising 1, 2, 3 or 4 heteroatoms individually selected from nitrogen, oxygen and sulfur, heteroaryloxy or heteroaryl$C_1$-$C_6$alkyl, wherein aryl and heteroaryl are optionally substituted with 1 to 3 groups represented by $R^9$ or 1 group represented by $R^{10}$;

$R^9$ is independently selected from halogen, cyano, hydroxyl, $C_1$-$C_6$alkyl, $C_1$-$C_6$alkoxy, $C_1$-$C_6$alkylthio, $C_2$-$C_6$alkenyl, $C_2$-$C_6$alkenyloxy, $C_2$-$C_6$alkynyl, $C_2$-$C_6$alkynyloxy, wherein $C_1$-$C_6$alkyl, $C_1$-$C_6$alkoxy, $C_1$-$C_6$alkylthio, $C_2$-$C_6$alkenyl, $C_2$-$C_6$alkenyloxy, $C_2$-$C_6$alkynyl, $C_2$-$C_6$alkynyloxy, are optionally substituted with 1 to 3 groups represented by $R^{11}$;

$R^{10}$ is selected from $C_3$-$C_6$cycloalkyl, $C_3$-$C_8$cycloalkoxy, $C_3$-$C_6$cycloalkylthio, aryl, aryloxy, arylthio, aryl$C_1$-$C_6$alkyl, heteroaryl wherein the heteroaryl is a 5- or 6-membered aromatic monocyclic ring comprising 1, 2, 3 or 4 heteroatoms individually selected from nitrogen, oxygen and sulfur, heteroaryloxy, heteroarylthio, heteroaryl$C_1$-$C_6$alkyl, heterocyclyl wherein the heterocyclyl is a 4-, 5- or 6-membered non-aromatic monocyclic ring comprising 1, 2 or 3 heteroatoms individually selected from nitrogen, oxygen and sulfur, heterocyclyloxy, heterocyclylthio or heterocyclyl$C_1$-$C_6$alkyl, wherein $C_3$-$C_6$cycloalkyl, $C_3$-$C_8$cycloalkoxy, $C_3$-$C_6$cycloalkylthio, aryl, aryloxy, arylthio, aryl$C_1$-$C_6$alkyl, heteroaryl, heteroaryloxy, heteroarylthio, heteroaryl$C_1$-$C_6$alkyl, heterocyclyl, heterocyclyloxy, heterocyclylthio and heterocyclyl$C_1$-$C_6$alkyl are optionally substituted with 1 to 3 groups represented by $R^{11}$;

$R^{11}$ is independently selected from halogen and methyl;

X is C—H or N;

or a salt or an N-oxide thereof.

Surprisingly, it has been found that the novel compounds of formula (I) have, for practical purposes, a very advantageous level of biological activity for protecting plants against diseases that are caused by fungi.

According to a second aspect of the invention, there is provided an agrochemical composition comprising a fungicidally effective amount of a compound of formula (I) according to the present invention.

According to a third aspect of the invention, there is provided a method of controlling or preventing infestation of useful plants by phytopathogenic microorganisms, wherein a fungicidally effective amount of a compound of formula (I), or a composition comprising this compound as active ingredient, is applied to the plants, to parts thereof or the locus thereof.

According to a fourth aspect of the invention, there is provided the use of a compound of formula (I) as a fungicide. According to this particular aspect of the invention, the use may or may not include methods for the treatment of the human or animal body by surgery or therapy.

Where substituents are indicated as being "optionally substituted", this means that they may or may not carry one or more identical or different substituents, e.g., one, two or three $R^9$ substituents. For example, $C_1$-$C_6$alkyl substituted by 1, 2 or 3 halogens, may include, but not be limited to, —$CH_2Cl$, —$CHCl_2$, —$CCl_3$, —$CH_2F$, —$CHF_2$, —$CF_3$, —$CH_2CF_3$ or —$CF_2CH_3$ groups. As another example, $C_1$-$C_6$alkoxy substituted by 1, 2 or 3 halogens, may include, but not be limited to, $CH_2ClO$—, $CHCl_2O$—, $CCl_3O$—, $CH_2FO$—, $CHF_2O$—, $CF_3O$—, $CF_3CH_2O$— or $CH_3CF_2O$— groups.

As used herein, the term "hydroxyl" or "hydroxy" means a —OH group.

As used herein, the term "cyano" means a —CN group.

As used herein, the term "halogen" refers to fluorine (fluoro), chlorine (chloro), bromine (bromo) or iodine (iodo).

As used herein, the term "$C_1$-$C_6$alkyl" refers to a straight or branched hydrocarbon chain radical consisting solely of carbon and hydrogen atoms, containing no unsaturation, having from one to six carbon atoms, and which is attached to the rest of the molecule by a single bond. The term "$C_1$-$C_{10}$alkyl" is to be construed accordingly. Examples of $C_1$-$C_6$alkyl include, but are not limited to, methyl, ethyl, n-propyl, n-butyl, n-pentyl, n-hexyl and the isomers thereof, for example, iso-propyl, iso-butyl, sec-butyl, tert-butyl or iso-amyl. A "$C_1$-$C_6$alkylene" group refers to the corresponding definition of $C_1$-$C_6$alkyl, except that such radical is attached to the rest of the molecule by two single bonds. The term "$C_1$-$C_2$alkylene" is to be construed accordingly. Examples of $C_1$-$C_6$alkylene, include, but are not limited to, —$CH_2$—, —$CH_2CH_2$— and —$(CH_2)_3$—.

As used herein, the term "$C_2$-$C_6$alkenyl" refers to a straight or branched hydrocarbon chain radical group consisting solely of carbon and hydrogen atoms, containing at least one double bond that can be of either the (E)- or (Z)-configuration, having from two to six carbon atoms, which is attached to the rest of the molecule by a single bond. The term "$C_2$-$C_{10}$alkenyl" is to be construed accordingly. Examples of $C_2$-$C_6$alkenyl include, but are not limited to, ethenyl (vinyl), prop-1-enyl, prop-2-enyl (allyl), but-1-enyl.

As used herein, the term "$C_2$-$C_6$alkynyl" refers to a straight or branched hydrocarbon chain radical group consisting solely of carbon and hydrogen atoms, containing at least one triple bond, having from two to six carbon atoms, and which is attached to the rest of the molecule by a single bond. The term "$C_2$-$C_{10}$alkynyl" is to be construed accordingly. Examples of $C_2$-$C_6$alkynyl include, but are not limited to, ethynyl, prop-1-ynyl, but-1-ynyl.

As used herein, the term "$C_1$-$C_6$alkoxy" refers to a radical of the formula —$OR_a$ where $R_a$ is a $C_1$-$C_6$alkyl radical as generally defined above. The term "$C_1$-$C_4$alkoxy" is to be construed accordingly. Examples of $C_1$-$C_6$alkoxy include, but are not limited to, methoxy, ethoxy, 1-methylethoxy (iso-propoxy), propoxy, butoxy, 1-methylpropoxy and 2-methylpropoxy.

As used herein, the term "$C_1$-$C_6$alkoxy$C_1$-$C_6$alkyl" refers to radical of the formula $R_b$—O—$R_a$— where $R_b$ is a $C_1$-$C_6$alkyl radical as generally defined above, and $R_a$ is a $C_1$-$C_6$alkylene radical as generally defined above. Examples of $C_1$-$C_6$alkoxy$C_1$-$C_6$alkyl include, but are not limited to, methoxymethyl.

As used herein, the term "$C_1$-$C_4$alkoxycarbonyl" refers to radical of the formula —$C(O)OR_a$ where $R_a$ is a $C_1$-$C_4$alkyl radical as generally defined above. Examples of $C_1$-$C_4$alkoxycarbonyl include, but are not limited to, methoxycarbonyl, ethoxycarbonyl.

As used herein, the term $C_1$-$C_6$alkylthio means an —$SR_a$ group, wherein $R_a$ is a $C_1$-$C_6$alkyl radical as generally defined above.

As used herein, the term "$C_1$-$C_6$haloalkyl" refers a $C_1$-$C_6$alkyl radical as generally defined above substituted by one or more of the same or different halogen atoms. The terms "$C_1$-$C_4$haloalkyl" and "$C_1$-$C_2$haloalkyl" are to be construed accordingly. Examples of $C_1$-$C_6$haloalkyl include, but are not limited to trifluoromethyl.

As used herein, the term "$C_3$-$C_6$cycloalkyl" refers to a radical which is a monocyclic saturated ring system and which contains 3 to 6 carbon atoms. The terms "$C_3$-$C_{10}$cycloalkyl" and "$C_3$-$C_8$cycloalkyl" are to be construed accordingly and may include bridged structures (e.g., norbornane). Examples of $C_3$-$C_{10}$cycloalkyl include, but are not limited to, cyclopropyl, 1-methylcyclopropyl, 2-methylcyclopropyl, cyclobutyl, cyclopentyl, cyclohexyl, cycloheptyl and cyclooctyl.

As used herein, the term "$C_3$-$C_{10}$cycloalkyl$C_1$-$C_2$alkyl" refers to a cycloalkyl ring attached to the rest of the molecule by a $C_1$-$C_2$alkyl radical as defined above. The term "$C_3$-$C_6$cycloalkyl$C_1$-$C_2$alkyl" is to be construed accordingly. Examples of $C_3$-$C_{10}$cycloalkyl$C_1$-$C_2$alkyl include, but are not limited to cyclopropylmethyl, cyclobutylmethyl, and cyclopentylmethyl.

As used herein, the term "$C_3$-$C_{10}$cycloalkenyl" refers to a radical which is a monocyclic non-aromatic ring system consisting solely of carbon and hydrogen atoms and which contains 3 to 10 carbon atoms and 1 or 2 endocyclic double bonds. They may include bridged structures (e.g., norbornene and 2,5-norbornadiene. Examples of $C_3$-$C_{10}$cycloalkenyl include, but are not limited to, cyclobutenyl, cyclopentenyl, cyclohexenyl, cycloheptenyl and cyclooctenyl.

As used herein, the term "$C_3$-$C_8$cycloalkoxy" refers to a radical of the formula —$OR_a$ where $R_a$ is a $C_3$-$C_6$cycloalkyl radical as generally defined above. The term $C_3$-$C_6$cycloalkoxy is to be construed accordingly. Examples of $C_3$-$C_8$cycloalkoxy include, but are not limited to, cyclopropyloxy, cyclopentyloxy or cyclohexyloxy.

As used herein, the term "$C_3$-$C_6$cycloalkylthio" refers to a radical of the formula —$SR_a$ where $R_a$ is a $C_3$-$C_6$cycloalkyl radical as generally defined above. Examples of $C_3$-$C_6$cycloalkylthio include, but are not limited to, cyclopropylthio, cyclopentylthio or cyclohexylthio.

As used herein, the term "$C_2$-$C_6$alkenyloxy" refers to a radical of the formula —$OR_a$ where $R_a$ is a $C_2$-$C_6$alkenyl radical as generally defined above. Examples of $C_2$-$C_6$alkenyloxy include, but are not limited to, allyloxy or butenyloxy.

As used herein, the term "$C_2$-$C_6$alkynyloxy" refers to a radical of the formula —$OR_a$ where $R_a$ is a $C_2$-$C_6$alkynyl radical as generally defined above. Examples of $C_2$-$C_6$alkynyloxy include, but are not limited to, propargyloxy or butynyloxy.

As used herein, the term "$C_2$-$C_6$acyl" refers to a radical $R_aC(=O)—$, where $R_a$ is a $C_1$-$C_5$alkyl radical or aryl radical as generally defined above. Acyl groups include, but are not limited to, acetyl, propanoyl and benzoyl.

As used herein, the term "$C_2$-$C_6$acyloxy" refers to a radical of the formula —$OR_b$ where $R_b$ is a formyl or a $C_2$-$C_6$acyl radical as generally defined above. $C_2$-$C_6$acyloxy groups include, but are not limited to, acetoxy.

As used herein, the term "$C_2$-$C_6$acyloxy$C_1$-$C_6$alkyl" refers to a radical of the formula $R_aC(=O)OR_b$— where $R_a$ is a $C_1$-$C_5$alkyl radical or aryl radical as generally defined above and where $R_b$ is a $C_1$-$C_6$alkylene radical as generally defined above.

As used herein, the term "heterocyclyl" or "heterocyclic" refers to a stable 4-, 5- or 6-membered non-aromatic monocyclic ring which comprises 1, 2 or 3 heteroatoms, wherein the heteroatoms are individually selected from nitrogen, oxygen and sulfur. The heterocyclyl radical may be bonded to the rest of the molecule via a carbon atom or heteroatom. Examples of heterocyclyl include, but are not limited to, azetidinyl, oxetanyl, thietanyl, tetrahydrofuryl, pyrrolidinyl, pyrazolidinyl, imidazolidnyl, piperidinyl, piperazinyl, morpholinyl, dioxolanyl, dithiolanyl and thiazolidinyl.

As used herein, the term "heterocyclyloxy" refers to a radical of the formula —$OR_a$ where $R_a$ is a heterocyclyl radical as generally defined above. Examples of heterocyclyloxy include, but are not limited to, tetrahydrofuranyloxy and morpholinyloxy.

As used herein, the term "heterocyclylthio" refers to a radical of the formula —$SR_a$ where $R_a$ is a heterocyclyl radical as generally defined above. Examples of heterocyclylthio include, but are not limited to, tetrahydrofuranylthio and morpholinylthio.

As used herein, the term "heterocyclyl$C_1$-$C_6$alkyl" refers to a heterocyclyl ring attached to the rest of the molecule by a $C_1$-$C_6$alkyl radical as defined above. The term heterocyclyl$C_1$-$C_2$alkyl is to be construed accordingly. Examples of heterocyclyl$C_1$-$C_6$alkyl include, but are not limited to tetrahydrofuranylmethyl or morpholinylmethyl.

As used herein, the term "aryl" refers to an aromatic ring system consisting solely of carbon and hydrogen atoms which may be mono-, bi- or tricyclic. Examples of such ring systems include phenyl, naphthalenyl, anthracenyl, indenyl or phenanthrenyl.

As used herein, the term "aryloxy" refers to a radical of the formula —$OR_a$ where $R_a$ is an aryl radical as generally defined above. Examples of aryloxy include, but are not limited to, phenoxy and napthyloxy.

As used herein, the term "arylthio" refers to a radical of the formula —$SR_a$ where $R_a$ is an aryl radical as generally defined above. Examples of arylthio include, but are not limited to, phenylthio and napthylthio.

As used herein, the term "aryl$C_1$-$C_6$alkyl" refers to an aryl ring attached to the rest of the molecule by a $C_1$-$C_6$alkylene radical as defined above. Examples of aryl$C_1$-$C_6$alkyl include, but are not limited to benzyl or 2-phenylethyl.

As used herein, the term "heteroaryl" refers to a 5- or 6-membered aromatic monocyclic ring radical which comprises 1, 2, 3 or 4 heteroatoms individually selected from nitrogen, oxygen and sulfur.

Examples of heteroaryl include, but are not limited to, furanyl, pyrrolyl, thienyl, pyrazolyl, imidazolyl, thiazolyl, isothiazolyl, oxazolyl, isoxazolyl, triazolyl, tetrazolyl, pyrazinyl, pyridazinyl, pyrimidyl or pyridyl.

As used herein, the term "heteroaryloxy" refers to a radical of the formula —$OR_a$ where $R_a$ is a heteroaryl radical as generally defined above. Examples of heteroaryloxy include, but are not limited to, pyridyloxy and thienyloxy.

As used herein, the term "heteroarylthio" refers to a radical of the formula —$SR_a$ where $R_a$ is a heteroaryl radical as generally defined above. Examples of heteroarylthio include, but are not limited to, pyridylthio and thienylthio.

As used herein, the term "heteroaryl$C_1$-$C_6$alkyl" refers to a heteroaryl ring attached to the rest of the molecule by a $C_1$-$C_6$ alkyl radical as defined above. The term "heteroaryl$C_1$-$C_2$alkyl" is to be construed accordingly.

As used herein, the term $C_1$-$C_6$alkylsulfonyl means an —$S(O)_2R_a$ group, wherein $R_a$ is a $C_1$-$C_6$alkyl radical as generally defined above.

As used herein, the term $C_1$-$C_6$alkylcarbonyloxy means an —$OC(=O)R_a$ group, wherein $R_a$ is a $C_1$-$C_6$alkyl radical as generally defined above.

As used herein, =O means an oxo group, e.g., as found in a carbonyl (—$C(=O)—$) group.

As used herein, an "annulated carbobicyclyl ring" is a non-aromatic bicyclic ring system comprising two rings fused together, i.e., sharing two carbon atoms.

As used herein, a "spirocyclic carbobicyclyl ring" is a non-aromatic bicyclic ring system comprising two rings joined together at one carbon atom, i.e., sharing one carbon atom.

The presence of one or more possible asymmetric carbon atoms in a compound of formula (I) means that the compounds may occur in optically isomeric forms, i.e., enantiomeric or diastereomeric forms. Also, atropisomers may occur as a result of restricted rotation about a single bond. Formula (I) is intended to include all those possible isomeric forms and mixtures thereof. The present invention includes all those possible isomeric forms and mixtures thereof for a compound of formula (I). Likewise, formula (I) is intended to include all possible tautomers. The present invention includes all possible tautomeric forms for a compound of formula (I).

In each case, the compounds of formula (I) according to the invention are in free form, in oxidized form as an N-oxide, or in salt form, e.g., an agronomically usable salt form.

N-oxides are oxidized forms of tertiary amines or oxidized forms of nitrogen-containing heteroaromatic compounds. They are described for instance in the book "Heterocyclic N-oxides" by A. Albini and S. Pietra, CRC Press, Boca Raton (1991).

The following list provides definitions, including preferred definitions, for substituents $R^1$, $R^2$, $R^3$, $R^4$, $R^5$, $R^6$, $R^7$, $R^8$, $R^9$, $R^{10}$ and $R^{11}$ and X with reference to compounds of formula (I). For any one of these substituents, any of the definitions given below may be combined with any definition of any other substituent given below or elsewhere in this document.

$R^1$ is halogen, cyano, $C_1$-$C_6$alkyl or $C_1$-$C_6$alkoxy, wherein $C_1$-$C_6$alkyl and $C_1$-$C_6$alkoxy are optionally substituted with 1 to 3 groups represented by $R^6$. $R^1$ may be halogen, cyano, $C_1$-$C_4$alkyl or $C_1$-$C_4$alkoxy, wherein $C_1$-$C_4$alkyl and $C_1$-$C_4$alkoxy are optionally substituted with 1 to 3 groups represented by $R^6$. Preferably, $R^1$ is halogen, cyano, methyl, trifluoromethyl, methoxy or trifluoromethoxy. More preferably, $R^1$ is halogen or cyano, even more preferably halogen, and further more preferably fluoro.

$R^2$ is hydrogen, $C_1$-$C_6$alkyl, $C_1$-$C_6$alkoxy or $C_3$-$C_6$cycloalkyl, wherein $C_1$-$C_6$alkyl, $C_1$-$C_6$alkoxy and $C_3$-$C_6$cycloalkyl are optionally substituted with 1 to 3 groups represented by $R^6$. Preferably, $R^2$ is hydrogen or $C_1$-$C_6$alkoxy (including $C_1$-$C_4$alkoxy), more preferably hydrogen or methoxy, and even more preferably hydrogen.

$R^3$ is halogen, $C_1$-$C_6$alkyl, $C_1$-$C_6$alkoxy or $C_3$-$C_6$cycloalkyl, wherein $C_1$-$C_6$alkyl, $C_1$-$C_6$alkoxy and $C_3$-$C_6$cycloalkyl are optionally substituted with 1 to 3 groups represented by $R^6$. Preferably, $R^3$ is halogen or $C_1$-$C_6$alkyl (including $C_1$-$C_4$alkyl), more preferably halogen (in particular, chloro or bromo) or methyl, even more preferably bromo or methyl, and more preferably still, methyl.

$R^4$ is hydrogen, $C_1$-$C_6$alkyl, $C_1$-$C_6$alkoxy or $C_3$-$C_6$cycloalkyl, wherein $C_1$-$C_6$alkyl, $C_1$-$C_6$alkoxy and $C_3$-$C_6$cycloalkyl are optionally substituted with 1 to 3 groups represented by $R^6$. Preferably, $R^4$ is hydrogen or $C_1$-$C_6$alkoxy (including $C_1$-$C_4$alkoxy); more preferably hydrogen or methoxy, and even more preferably hydrogen.

$R^5$ is $C_1$-$C_{10}$alkyl, $C_3$-$C_{10}$cycloalkyl, $C_3$-$C_{10}$cycloalkyl$C_1$-$C_2$alkyl, $C_3$-$C_{10}$cycloalkenyl, $C_2$-$C_{10}$alkenyl, $C_2$-$C_{10}$alkynyl, aryl, heteroaryl wherein the heteroaryl is a 5- or 6-membered aromatic monocyclic ring comprising 1, 2, 3 or 4 heteroatoms individually selected from nitrogen, oxygen and sulfur, heterocyclyl wherein the heterocyclyl is a 4-, 5- or 6-membered non-aromatic monocyclic ring comprising 1, 2 or 3 heteroatoms individually selected from nitrogen, oxygen and sulfur, heterocyclyl$C_1$-$C_2$alkyl, or a 5- to 10-membered (preferably, 7- to 10-membered) non-aromatic annulated or spirocyclic carbobicyclyl ring system optionally comprising 1, 2, 3, 4 or 5 heteroatoms individually selected from nitrogen, oxygen and sulfur, and optionally bonded to the rest of the molecule through a $C_1$-$C_2$alkylene linker;

wherein any of said $C_1$-$C_{10}$alkyl, $C_3$-$C_{10}$cycloalkyl, $C_3$-$C_{10}$cycloalkenyl, $C_2$-$C_{10}$alkenyl and $C_2$-$C_{10}$alkynyl moieties are optionally substituted with 1 to 4 groups represented by $R^7$ or 1 group represented by $R^8$; or wherein any of said aryl, heteroaryl and heterocyclyl moieties are optionally substituted with 1 to 3 groups represented by $R^9$ or 1 group represented by $R^{10}$, or are optionally substituted with 1 or 2 groups represented by $R^9$ and 1 group represented by $R^{10}$; or wherein the annulated or spirocyclic carbobicyclyl ring is optionally substituted with 1 to 3 groups represented by $R^7$, or the annulated carbobicyclyl ring system is optionally substituted by $C_3$-$C_6$cycloalkyl to form a spirocyclyl moiety.

Preferably, $R^5$ is $C_1$-$C_6$alkyl, $C_3$-$C_6$cycloalkyl, $C_3$-$C_6$cycloalkyl$C_1$-$C_2$alkyl, $C_3$-$C_6$cycloalkenyl, $C_2$-$C_6$alkenyl, $C_2$-$C_6$alkynyl, phenyl, heteroaryl wherein the heteroaryl is a 5- or 6-membered aromatic monocyclic ring comprising 1, 2, 3 or 4 heteroatoms individually selected from nitrogen, oxygen and sulfur, heterocyclyl wherein the heterocyclyl is a 4-, 5- or 6-membered non-aromatic monocyclic ring comprising 1, 2 or 3 heteroatoms individually selected from nitrogen, oxygen and sulfur, heterocyclyl$C_1$-$C_2$alkyl, or a 5- to 10-membered non-aromatic annulated or spirocyclic carbobicyclyl ring system optionally comprising 1, 2 or 3 heteroatoms individually selected from nitrogen, oxygen and sulfur, and optionally bonded to the rest of the molecule through a $C_1$-$C_2$alkylene linker;

wherein any of said $C_1$-$C_6$alkyl, $C_3$-$C_6$cycloalkyl, $C_3$-$C_6$cycloalkenyl, $C_2$-$C_6$alkenyl and $C_2$-$C_6$alkynyl moieties are optionally substituted with 1 to 4 groups represented by $R^7$ or 1 group represented by $R^8$; or wherein any of said phenyl, heteroaryl and heterocyclyl moieties are optionally substituted with 1 to 3 groups represented by $R^9$ or 1 group represented by $R^{10}$, or are optionally substituted with 1 or 2 groups represented by $R^9$ and 1 group represented by $R^{10}$; or wherein the annulated or spirocyclic carbobicyclyl ring is optionally substituted with 1 to 3 groups represented by $R^7$, or the annulated carbobicyclyl ring system is optionally substituted by $C_3$-$C_6$cycloalkyl to form a spirocyclyl moiety.

More preferably, $R^5$ is $C_1$-$C_6$alkyl, $C_3$-$C_6$cycloalkyl, $C_3$-$C_8$cycloalkyl$C_{1-2}$alkyl, $C_2$-$C_6$alkynyl, phenyl, heterocyclyl, wherein the heterocyclyl is a 4- or 6-membered non-aromatic monocyclic ring comprising 1 oxygen atom, heterocyclyl$C_1$alkyl, or a 5- to 9-membered non-aromatic annulated or spirocyclic carbobicyclyl ring system optionally comprising 1 oxygen atom, and optionally bonded to the rest of the molecule through a methylene (—$CH_2$—) linker;

wherein any of said $C_1$-$C_6$alkyl, $C_3$-$C_6$cycloalkyl and $C_2$-$C_6$alkynyl, moieties are optionally substituted with 1 to 4 groups represented by $R^7$ or 1 group represented by $R^8$;

wherein any of said phenyl or heterocyclyl moieties are optionally substituted with 1 or 2 groups represented by $R^9$ or 1 group represented by $R^{10}$, or are optionally substituted with 1 or 2 groups represented by $R^9$ and 1 group represented by $R^{10}$; and wherein the annulated or spirocyclic carbobicyclyl ring is optionally substituted with 1 or 2 groups represented by $R^7$, or the annulated carbobicyclyl ring system is optionally substituted by $C_4$-$C_5$cycloalkyl to form a spirocyclyl moiety.

Even more preferably, $R^5$ is $C_1$-$C_6$alkyl, $C_3$-$C_6$cycloalkyl, $C_3$-$C_6$cycloalkyl$C_1$-$C_2$alkyl, or $C_2$-$C_6$alkynyl, wherein any of the $C_1$-$C_6$alkyl, $C_2$-$C_6$alkynyl and $C_3$-$C_6$cycloalkyl moieties are optionally substituted with 1 to 4 groups represented by $R^7$ or 1 group represented by $R^8$, wherein $R^7$ is independently selected from halogen, cyano, hydroxyl, $C_1$-$C_6$alkyl, $C_1$-$C_6$haloalkyl, $C_1$-$C_4$alkoxy, $C_1$-$C_4$alkoxy$C_1$-$C_4$alkyl, $C_3$-$C_6$cycloalkyl, $C_3$-$C_6$cycloalkyl$C_{1-2}$alkyl, and $C_1$-$C_3$alkoxycarbonyl, wherein $R^8$ is phenyl, benzyl or isoxazole optionally substituted with 1 to 3 groups represented by $R^9$ or 1 group represented by $R^{10}$, and wherein $R^9$ is halogen and $R^{10}$ is phenyl optionally substituted by 1 to 3 groups represented by $R^{11}$ which are halogen.

More preferably still, $R^5$ is $C_1$-$C_6$alkyl, $C_2$-$C_6$alkynyl, $C_3$-$C_6$cycloalkyl or $C_3$-$C_6$cycloalkyl$C_1$-$C_2$alkyl, optionally substituted with 1 group represented by $R^7$, wherein $R^7$ is methyl, hydroxyl, cyano, trifluoromethyl, methoxymethyl, $C_3$-$C_6$cycloalkyl, ethoxycarbonyl, acetyloxymethyl, or 2,2-dichlorocyclopropyl; or 2 groups represented by $R^7$, wherein each $R^7$ is independently methyl, cyano or cyclopropyl; or 3 groups represented by $R^7$, wherein each $R^7$ is independently methyl, bromo, chloro, fluoro or butoxy; or 4 groups represented by $R^7$ wherein each $R^7$ is methyl, or 1 group represented by $R^8$, wherein $R^8$ is phenyl, benzyl or isoxazole optionally substituted with 1 to 3 groups represented by $R^9$ or 1 group represented by $R^{10}$, and wherein $R^9$ is halogen and $R^{10}$ is phenyl optionally substituted by 1 to 3 groups represented by $R^{11}$ which are halogen; or $R^5$ is phenyl, pyridylmethyl (including 2-pyridylmethyl, 3-pyridylmethyl and 4-pyridylmethyl), oxetanyl (including oxetan-2-yl, oxetan-3-yl), tetrahydrofuranyl (tetrahydrofuran-2-yl, tetrahydrofuran-3-yl) or tetrahydropyranyl (tetrahydropyran-2-yl, tetrahydropyran-3-yl, tetrahydropyran-4-yl) each optionally substituted with 1 to 3 groups represented by $R^9$ or 1 group represented by $R^{10}$, or 1 or 2 groups represented by $R^9$ and 1 group represented by $R^{10}$, wherein $R^9$ is independently selected from halogen and $C_1$-$C_4$alkyl, and $R^{10}$ is selected from phenyl, benzyl or $C_6$-$C_8$cycloalkoxy each optionally substituted by 1 to 3 groups represented by $R^{11}$ which are independently selected from halogen or methyl;

or $R^5$ is an annulated or spirocyclic ring system selected from:

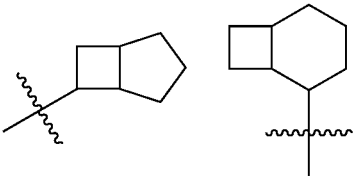

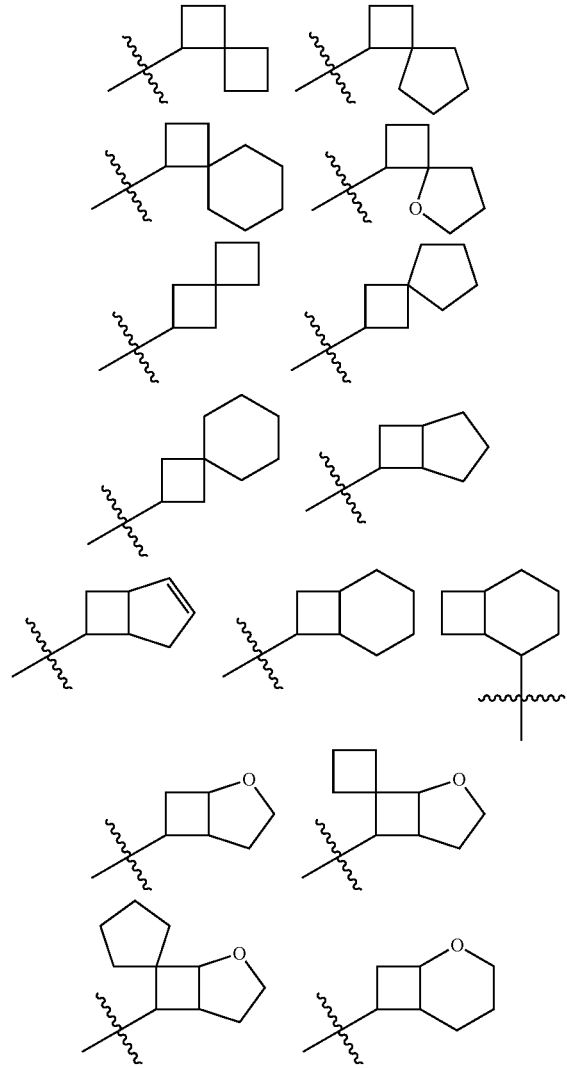

each optionally substituted by 1 to 3 groups represented by $R^7$ independently selected from $C_1$-$C_4$alkyl and $C_2$-$C_4$acyloxy$C_1$-$C_4$alkyl:

Still more preferably, $R^5$ is $C_1$-$C_4$alkyl optionally substituted by 1 group represented by $R^7$ selected from $C_3$-$C_6$cycloalkyl; or $R^5$ is an annulated or spirocyclic ring system selected from:

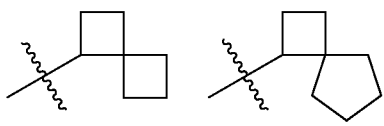

each optionally substituted by 1 to 3 groups represented by $R^7$ independently selected from $C_1$-$C_4$alkyl, in particular methyl.

In particularly preferred embodiments of the invention, $R^5$ is (3,4-difluorophenyl)methyl, (2,4,5-trifluorophenyl) methyl, (2-chloro-4,5-difluorophenyl)methyl, (2-bromo-4, 5-difluorophenyl)methyl, 1-cyclohexylethyl, 1-phenylethyl, 1-(3-phenylisoxazol-5-yl)ethyl, 1-[3-(2-iodophenyl)isoxazol-5-yl]ethyl, [2-methyl-1-(trifluoromethyl)propyl], [1-(hydroxymethyl)-2,2-dimethyl-propyl], (1-benzyl-2,2-dimethyl-propyl), (1-isopropyl-2-methyl-but-3-ynyl), [1-(1-cyanoethyl)-2-methyl-propyl], [3-methyl-1-(1-methyl-2-phenyl-ethyl)butyl], (1-cyclohexylcyclopropyl), (3-isobutoxy-2,2-dimethyl-cyclobutyl), spiro[3.3]heptan-7-yl], [(7R)-spiro[3.3]heptan-7-yl], spiro[3.4]octan-3-yl, spiro [3.4]octan-2-yl, [3-(acetoxymethyl)-8-oxaspiro[3.4]octan-1-yl], spiro[3.5]nonan-2-yl, [(1R,5S,6R)-6-bicyclo[3.2.0] heptanyl], [(1S,5R,7R)-5-methyl-7-bicyclo[3.2.0]heptanyl], 6,6-dimethyl-7-bicyclo[3.2.0]heptanyl], [(1 S,5R,7S)-6,6-dimethyl-7-bicyclo[3.2.0]heptanyl], [(1 S,5S)-6,6-dimethyl-7-bicyclo[3.2.0]hept-3-enyl], (6,6-dimethyl-4-oxabicyclo [3.2.0]heptan-7-yl), spiro[4-oxabicyclo[3.2.0]heptane-6,1'-cyclobutane]-7-yl, spiro[4-oxabicyclo[3.2.0]heptane-6,1'-cyclopentane]-7-yl, [(1 S,6R,8R)-6-methyl-8-bicyclo[4.2.0] octanyl], (7,7-dimethyl-5-oxabicyclo[4.2.0]octan-8-yl), (1-benzylcyclohexyl), (3,3,5,5-tetramethylcyclohexyl), (6-methyl-2-bicyclo[4.2.0]octanyl), [(3S)-2-(2,4-dichlorophenyl)oxetan-3-yl], (4-benzyl-2,6-dimethyl-tetrahydropyran-4-yl), [4-(4,4-dimethylcyclohexoxy)-2-fluoro-phenyl], [4-(cyclooctoxy)-2-fluoro-phenyl], [4-(4-chlorophenoxy) phenyl], 2,2-dimethylpropyl, (1-methylcyclopropyl)methyl, (1-m ethylcyclopentyl)methyl, (4-methyltetrahydropyran-4-yl)methyl, (3-methoxy-2,2-dimethyl-propyl), (1-methylcyclobutyl)methyl, (1-cyclopropylcyclopropyl), (1-cyano-1-cyclopropyl-ethyl), (1-ethoxycarbonylcyclopropyl)methyl, [1-(cyclopropylmethyl)cyclopropyl]methyl, (3-methyloxetan-3-yl)methyl, (1-methoxycyclopentyl)methyl, 1-(2-pyridyl)ethyl, spiro[2.2]pentan-5-yl, [1-(methoxymethyl) cyclopropyl]methyl, 6-oxaspiro[2.5]octan-2-ylmethyl, [1-(trifluoromethyl)cyclopropyl]methyl, and [1-(methoxymethyl)cyclopentyl]methyl.

In even more preferred embodiments, $R^5$ is (3,4-difluorophenyl)methyl, (2,4,5-trifluorophenyl)methyl, (2-chloro-4,5-difluorophenyl)methyl, (2-bromo-4,5-difluorophenyl) methyl, 1-cyclohexylethyl, 1-phenylethyl, 1-(3-phenylisoxazol-5-yl)ethyl, 1-[3-(2-iodophenyl)isoxazol-5-yl]ethyl, [2-methyl-1-(trifluoromethyl)propyl], [1-(hydroxymethyl)-2,2-dimethyl-propyl], (1-benzyl-2,2-dimethyl-propyl), (1-isopropyl-2-methyl-but-3-ynyl), [1-(1-cyanoethyl)-2-methyl-propyl], [3-methyl-1-(1-methyl-2-phenyl-ethyl)butyl], (1-cyclohexylcyclopropyl), (3-isobutoxy-2,2-dimethyl-cyclobutyl), spiro[3.3]heptan-7-yl], [(7R)-spiro[3.3]heptan-7-yl], spiro[3.4]octan-3-yl, spiro [3.4]octan-2-yl, [3-(acetoxymethyl)-8-oxaspiro[3.4]octan-1-yl], spiro[3.5]nonan-2-yl, [(1R,5S,6R)-6-bicyclo[3.2.0] heptanyl], [(1S,5R,7R)-5-methyl-7-bicyclo[3.2.0]heptanyl], 6,6-dimethyl-7-bicyclo[3.2.0]heptanyl], [(1 S,5R,7S)-6,6- dimethyl-7-bicyclo[3.2.0]heptanyl], [(1 S,5S)-6,6-dimethyl-7-bicyclo[3.2.0]hept-3-enyl], (6,6-dimethyl-4-oxabicyclo[3.2.0]heptan-7-yl), spiro[4-oxabicyclo[3.2.0]heptane-6,1'-cyclobutane]-7-yl), spiro[4-oxabicyclo[3.2.0]heptane-6,1'-cyclopentane]-7-yl, [(1 S,6R,8R)-6-methyl-8-bicyclo[4.2.0] octanyl], (7,7-dimethyl-5-oxabicyclo[4.2.0]octan-8-yl), (1-benzylcyclohexyl), (3,3,5,5-tetramethylcyclohexyl), (6-methyl-2-bicyclo[4.2.0]octanyl), [(3S)-2-(2,4-dichlorophenyl)oxetan-3-yl], (4-benzyl-2,6-dimethyl-tetrahydropyran-4-yl), [4-(4,4-dimethylcyclohexoxy)-2-fluoro-phenyl], [4-(cyclooctoxy)-2-fluoro-phenyl], [4-(4-chlorophenoxy)phenyl], 2,2-dimethylpropyl, (1-methylcyclopropyl)methyl, (1-m ethylcyclopentyl)methyl, (4-methyltetrahydropyran-4-yl)methyl, (3-methoxy-2,2-dimethyl-propyl), (1-methylcyclobutyl)methyl, (1-cyclopropylcyclopropyl), (1-cyano-1-cyclopropyl-ethyl), (1-ethoxycarbonylcyclopropyl)methyl, [1-(cyclopropylmethyl)cyclopropyl]methyl, (3-methyloxetan-3-yl)methyl, 1-(2-pyridyl)ethyl, spiro[2.2]pentan-5-yl, [1-(trifluoromethyl)cyclopropyl]methyl, and [1-(methoxymethyl)cyclopentyl]methyl.

In still even more preferred embodiments, $R^5$ is 1-cyclohexylethyl, 1-phenylethyl, 1-(3-phenylisoxazol-5-yl)ethyl, spiro[3.3]heptan-7-yl], spiro[3.4]octan-3-yl, spiro[3.4]octan-2-yl, spiro[3.5]nonan-2-yl, [3-(acetoxymethyl)-8-oxaspiro[3.4]octan-1-yl], 6,6-dimethyl-7-bicyclo[3.2.0]heptanyl], (6,6-dimethyl-4-oxabicyclo[3.2.0]heptan-7-yl), spiro [4-oxabicyclo[3.2.0]heptane-6,1'-cyclobutane]-7-yl, spiro [4-oxabicyclo[3.2.0]heptane-6,1'-cyclopentane]-7-yl, (6-methyl-2-bicyclo[4.2.0]octanyl), and spiro[2.2]pentan-5-yl.

$R^6$ is independently selected from halogen, cyano, hydroxyl, $C_1$-$C_6$alkoxy, and $C_3$-$C_6$cycloalkyl. Preferably, $R^6$ is independently selected from halogen, cyano, hydroxyl, $C_1$-$C_4$alkoxy, and $C_3$-$C_6$cycloalkyl.

$R^7$ is independently selected from halogen, cyano, hydroxyl, $C_1$-$C_6$alkyl, $C_1$-$C_6$haloalkyl, $C_1$-$C_6$alkoxy, $C_1$-$C_6$alkoxy$C_1$-$C_6$alkyl, $C_3$-$C_6$cycloalkyl, $C_3$-$C_6$cycloalkyl$C_{1-2}$alkyl, $C_2$-$C_6$acyl, $C_2$-$C_6$acyloxy, $C_2$-$C_6$acyloxy$C_1$-$C_6$alkyl, and $C_1$-$C_4$alkoxycarbonyl.

Preferably, $R^7$ is independently selected from halogen, cyano, hydroxyl, $C_1$-$C_4$alkyl, $C_1$-$C_4$haloalkyl, $C_1$-$C_4$alkoxy $C_1$-$C_4$alkoxy$C_1$-$C_4$alkyl, $C_3$-$C_6$cycloalkyl, $C_3$-$C_6$cycloalkyl$C_{1-2}$alkyl, and $C_1$-$C_4$alkoxycarbonyl; wherein the $C_3$-$C_6$cycloalkyl moiety is optionally substituted with 1 or 2 groups selected from halogen and $C_1$-$C_6$alkyl.

More preferably, $R^7$ is independently selected from chloro, bromo, fluoro, cyano, hydroxyl, methyl, trifluoromethyl, methoxy, butoxy, methoxymethyl, cyclopropyl, cyclohexyl, cyclooctyl, cyclopropylmethyl, acetyloxymethyl and ethoxycarbonyl; wherein cyclopropyl is optionally substituted with 2 chloro groups.

$R^8$ is aryl, aryloxy, aryl$C_1$-$C_6$alkyl, heteroaryl wherein the heteroaryl is a 5- or 6-membered aromatic monocyclic ring comprising 1, 2, 3 or 4 heteroatoms individually selected from nitrogen, oxygen and sulfur, heteroaryloxy or heteroaryl$C_1$-$C_6$alkyl, wherein aryl and heteroaryl are optionally substituted with 1 to 3 groups represented by $R^9$ or 1 group represented by $R^{10}$.

Preferably, $R^8$ is phenyl, benzyl or isoxazole optionally substituted with 1 to 3 groups represented by $R^9$ or 1 group represented by $R^{10}$. More preferably $R^8$ is phenyl, benzyl or isoxazole, wherein isoxazole is optionally substituted with 1 group represented by $R^{10}$.

$R^9$ is independently selected from halogen, cyano, hydroxyl, $C_1$-$C_6$alkyl, $C_1$-$C_6$alkoxy, $C_1$-$C_6$alkylthio, $C_2$-$C_6$alkenyl, $C_2$-$C_6$alkenyloxy, $C_2$-$C_6$alkynyl, $C_2$-$C_6$alkynyloxy, wherein $C_1$-$C_6$alkyl, $C_1$-$C_6$alkoxy, $C_1$-$C_6$alkylthio, $C_2$-$C_6$alkenyl, $C_2$-$C_6$alkenyloxy, $C_2$-$C_6$alkynyl, $C_2$-$C_6$alkynyloxy, are optionally substituted with 1 to 3 groups represented by $R^1$. Preferably, $R^9$ is independently selected from halogen, cyano, hydroxyl and $C_1$-$C_4$alkyl. More preferably, $R^9$ is independently selected from chloro, bromo, fluoro, and methyl.

$R^{10}$ is selected from $C_3$-$C_6$cycloalkyl, $C_3$-$C_8$cycloalkoxy (preferably $C_3$-$C_6$cycloalkoxy), $C_3$-$C_6$cycloalkylthio, aryl, aryloxy, arylthio, aryl$C_1$-$C_6$alkyl, heteroaryl wherein the heteroaryl is a 5- or 6-membered aromatic monocyclic ring comprising 1, 2, 3 or 4 heteroatoms individually selected from nitrogen, oxygen and sulfur, heteroaryloxy, heteroarylthio, heteroaryl$C_1$-$C_6$alkyl, heterocyclyl wherein the heterocyclyl is a 4-, 5- or 6-membered non-aromatic monocyclic ring comprising 1, 2 or 3 heteroatoms individually selected from nitrogen, oxygen and sulfur, heterocyclyloxy, heterocyclylthio and heterocyclyl$C_1$-$C_6$alkyl, wherein $C_3$-$C_6$cycloalkyl, $C_3$-$C_8$cycloalkoxy, $C_3$-$C_6$cycloalkylthio, aryl, aryloxy, arylthio, aryl$C_1$-$C_6$alkyl, heteroaryl, heteroaryloxy, heteroarylthio, heteroaryl$C_1$-$C_6$alkyl, heterocyclyl, heterocyclyloxy, heterocyclylthio and heterocyclyl$C_1$-$C_6$alkyl are optionally substituted with 1 to 3 groups represented by $R^{11}$.

Preferably, $R^{10}$ is selected from phenyl, benzyl and $C_6$-$C_5$cycloalkoxy each optionally substituted by 1 to 3 groups represented by $R^{11}$. More preferably, $R^{10}$ is phenyl, optionally substituted by 1 $R^{11}$.

$R^{11}$ is independently selected from halogen and methyl.

X is CH or N. In one embodiment of the invention, X is CH. In another embodiment of the invention, X is N.

According to the present invention, preferably:
$R^1$ is halogen or cyano;
$R^2$ is hydrogen or $C_1$-$C_4$alkoxy;
$R^3$ is halogen or $C_1$-$C_6$alkyl;
$R^4$ is hydrogen;
$R^5$ is $C_1$-$C_6$alkyl, $C_3$-$C_6$cycloalkyl, $C_3$-$C_6$cycloalkyl$C_1$-$C_2$alkyl, $C_3$-$C_6$cycloalkenyl, $C_2$-$C_6$alkenyl, $C_2$-$C_6$alkynyl, phenyl, heteroaryl wherein the heteroaryl is a 5- or 6-membered aromatic monocyclic ring comprising 1, 2, 3 or 4 heteroatoms individually selected from nitrogen, oxygen and sulfur, heterocyclyl wherein the heterocyclyl is a 4-, 5- or 6-membered non-aromatic monocyclic ring comprising 1, 2 or 3 heteroatoms individually selected from nitrogen, oxygen and sulfur, heterocyclyl$C_1$-$C_2$alkyl, or a 5- to 10-membered non-aromatic annulated or spirocyclic carbobicyclyl ring system optionally comprising 1, 2 or 3 heteroatoms individually selected from nitrogen, oxygen and sulfur, and optionally bonded to the rest of the molecule through a $C_1$-$C_2$alkylene linker;
wherein any of said $C_1$-$C_6$alkyl, $C_3$-$C_6$cycloalkyl, $C_3$-$C_6$cycloalkenyl, $C_2$-$C_6$alkenyl and $C_2$-$C_6$alkynyl moieties are optionally substituted with 1 to 4 groups represented by $R^7$ or 1 group represented by $R^8$; or
wherein any of said phenyl, heteroaryl and heterocyclyl moieties are optionally substituted with 1 to 3 groups represented by $R^9$ or 1 group represented by $R^{10}$, or are optionally substituted with 1 or 2 groups represented by $R^9$ and 1 group represented by $R^{10}$, and
wherein the annulated or spirocyclic carbobicyclyl ring system is optionally substituted with 1 to 3 groups represented by $R^7$, or the annulated carbobicyclyl ring system is optionally substituted by $C_3$-$C_6$cycloalkyl to form a spirocyclic moiety; and $R^7$ is independently selected from halogen, cyano, hydroxyl, $C_1$-$C_6$alkyl, $C_1$-$C_6$haloalkyl, $C_1$-$C_4$alkoxy, $C_1$-$C_4$alkoxy$C_1$-$C_4$alkyl, $C_3$-$C_6$cycloalkyl, $C_3$-$C_6$cycloalkyl$C_1$-$C_2$alkyl, $C_2$-$C_4$acyloxy$C_1$-$C_4$alkyl, and $C_1$-$C_4$alkoxycarbonyl, wherein the $C_3$-$C_6$cycloalkyl moiety of $C_3$-$C_6$cycloalkyl$C_{1-2}$alkyl is optionally substituted with 1 or 2 groups selected from halogen and $C_1$-$C_6$alkyl; $R^8$ is phenyl, benzyl or isoxazole optionally substituted with 1 to 3 groups represented by $R^9$ or 1 group represented by $R^{10}$;

$R^9$ is independently selected from halogen and $C_1$-$C_4$alkyl;

$R^{10}$ is phenyl, benzyl or $C_6$-$C_5$cycloalkoxy optionally substituted by 1 to 3 groups represented by $R^{11}$;

$R^{11}$ is halogen; and

X is CH.

More preferably, $R^1$ is halogen;

$R^2$ is hydrogen or methoxy;

$R^3$ is bromo or methyl;

$R^4$ is hydrogen;

$R^5$ is $C_1$-$C_6$alkyl, $C_3$-$C_6$cycloalkyl, $C_3$-$C_6$cycloalkyl$C_1$-$C_2$alkyl, $C_3$-$C_6$cycloalkenyl, $C_2$-$C_6$alkenyl, $C_2$-$C_6$alkynyl, phenyl, heteroaryl wherein the heteroaryl is a 5- or 6-membered aromatic monocyclic ring comprising 1, 2 or 3 heteroatoms individually selected from nitrogen, oxygen and sulfur, heterocyclyl wherein the heterocyclyl is a 4-, 5- or 6-membered non-aromatic monocyclic ring comprising 1, 2 or 3 heteroatoms individually selected from nitrogen, oxygen and sulfur, heterocyclyl$C_1$-$C_2$alkyl, or a 5- to 10-membered non-aromatic annulated or spirocyclic carbobicyclyl ring system optionally comprising 1, 2 or 3 heteroatoms individually selected from nitrogen, oxygen and sulfur, and optionally bonded to the rest of the molecule through a $C_1$-$C_2$alkylene linker;

wherein any of said $C_1$-$C_6$alkyl, $C_3$-$C_6$cycloalkyl, $C_3$-$C_6$cycloalkenyl, $C_2$-$C_6$alkenyl and $C_2$-$C_6$alkynyl moieties are optionally substituted with 1 to 4 groups represented by $R^7$ or 1 group represented by $R^8$;

wherein any of said phenyl, heteroaryl and heterocyclyl moieties are optionally substituted with 1 to 3 groups represented by $R^9$ or 1 group represented by $R^{10}$, or are optionally substituted with 1 or 2 groups represented by $R^9$ and 1 group represented by $R^{10}$, and wherein the annulated or spirocyclic carbobicyclyl ring is optionally substituted with 1 to 3 groups represented by $R^7$, or the annulated carbobicyclyl ring system is optionally substituted by $C_3$-$C_6$cycloalkyl to form a spirocyclic moiety; and $R^7$ is independently selected from halogen, cyano, hydroxyl, $C_1$-$C_6$alkyl, $C_1$-$C_6$haloalkyl, $C_1$-$C_4$alkoxy, $C_1$-$C_4$alkoxy$C_1$-$C_4$alkyl, $C_3$-$C_6$cycloalkyl, $C_3$-$C_6$cycloalkyl$C_1$-$C_2$alkyl, $C_2$-$C_4$acyloxy$C_1$-$C_4$alkyl, and $C_1$-$C_4$alkoxycarbonyl, wherein the $C_3$-$C_6$cycloalkyl moiety of $C_3$-$C_6$cycloalkyl$C_{1-2}$alkyl is optionally substituted with 1 or 2 groups selected from halogen and $C_1$-$C_6$alkyl;

$R^8$ is phenyl, benzyl or isoxazole optionally substituted with 1 to 3 groups represented by $R^9$ or 1 group represented by $R^{10}$ $R^9$ is independently selected from halogen and $C_1$-$C_4$alkyl;

$R^{10}$ is phenyl, benzyl or $C_6$-$C_8$cycloalkoxy optionally substituted by 1 to 3 groups represented by $R^{11}$;

$R^{11}$ is halogen; and

X is CH.

Even more preferably, $R^1$ is fluoro;

$R^2$ is hydrogen;

$R^3$ is bromo or methyl;

$R^4$ is hydrogen;

$R^5$ is $C_1$-$C_6$alkyl optionally substituted by 1 group represented by $R^7$ selected from $C_3$-$C_6$cycloalkyl, or an annulated or spirocyclic ring system selected from:

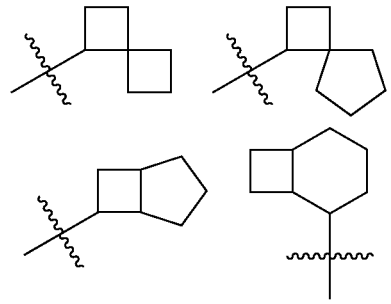

each optionally substituted by 1 to 3 groups represented by $R^7$ independently selected from $C_1$-$C_4$alkyl.

Still more preferably, $R^1$ is fluoro;

$R^2$ is hydrogen;

$R^3$ is bromo or methyl;

$R^4$ is hydrogen;

$R^5$ is $C_{1-4}$alkyl optionally substituted by 1 group represented by $R^7$ selected from cyclopropyl, cyclopentyl or cyclohexyl, or an annulated or spirocyclic ring system selected from:

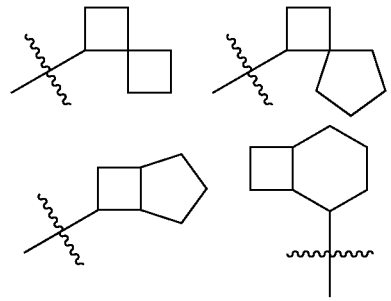

each optionally substituted by 1 to 3 groups represented by $R^7$ independently selected from methyl.

In a further preferable embodiment, $R^1$ is fluoro;

$R^2$ is hydrogen;

$R^3$ is bromo or methyl;

$R^4$ is hydrogen;

$R^5$ is $C_1$-$C_4$alkyl optionally substituted by 1 cyclohexyl group; or an annulated or spirocyclic ring system selected from:

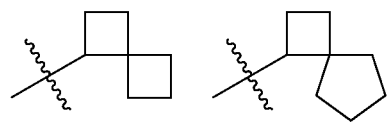

-continued

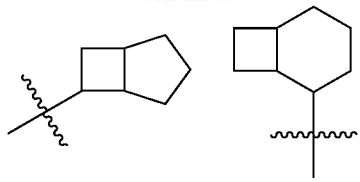

each optionally substituted by 1 or 2 groups represented by $R^7$, wherein $R^7$ is methyl.

Preferably, the compound according to Formula (I) is selected from:

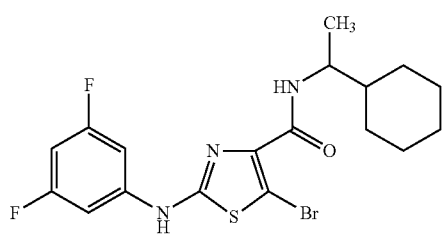 [SMILES: CC(NC(=O)c1nc(Nc2cc(F)cc(F)c2)sc1Br)C1CCCCC1]

5-bromo-N-(1-cyclohexylethyl)-2-(3,5-difluoroanilino)thiazole-4-carboxamide;

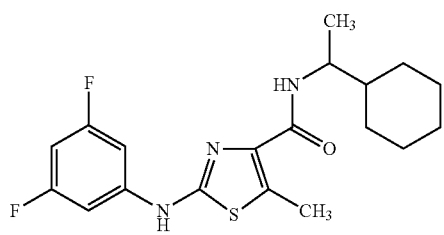 [SMILES: Cc1sc(Nc2cc(F)cc(F)c2)nc1C(=O)NC(C)C1CCCCC1]

N-(1-cyclohexylethyl)-2-(3,5-difluoroanilino)-5-methyl-thiazole-4-carboxamide;

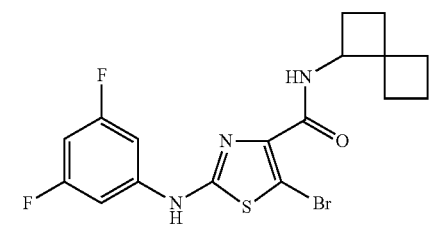 [SMILES: O=C(NC1CCC12CCC2)c1nc(Nc2cc(F)cc(F)c2)sc1Br]

5-bromo-2-(3,5-difluoroanilino)-N-spiro[3.3]heptan-7-yl-thiazole-4-carboxamide;

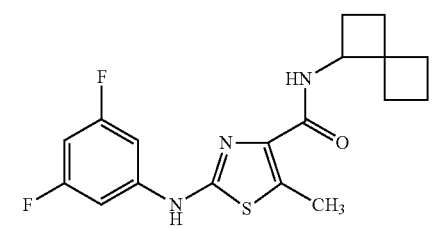 [SMILES: Cc1sc(Nc2cc(F)cc(F)c2)nc1C(=O)NC1CCC12CCC2]

2-(3,5-difluoroanilino)-5-methyl-N-spiro[3.3]heptan-7-yl-thiazole-4-carboxamide;

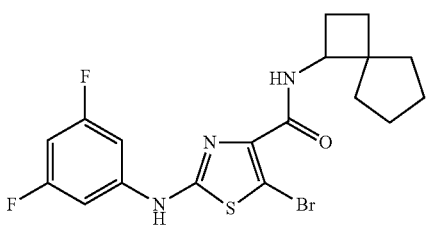 [SMILES: O=C(NC1CCC12CCCC2)c1nc(Nc2cc(F)cc(F)c2)sc1Br]

5-bromo-2-(3,5-difluoroanilino)-N-spiro[3.4]octan-3-yl-thiazole-4-carboxamide;

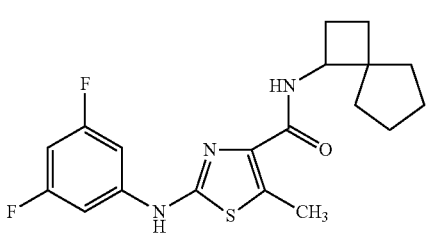 [SMILES: Cc1sc(Nc2cc(F)cc(F)c2)nc1C(=O)NC1CCC12CCCC2]

2-(3,5-difluoroanilino)-5-methyl-N-spiro[3.4]octan-3-yl-thiazole-4-carboxamide;

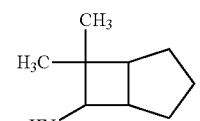
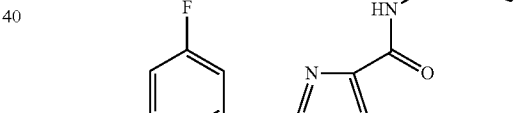

5-bromo-2-(3,5-difluoroanilino)-N-(6,6-dimethyl-7-bicyclo[3.2.0]heptanyl)thiazole-4-carboxamide;

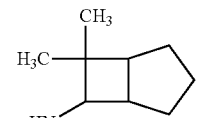
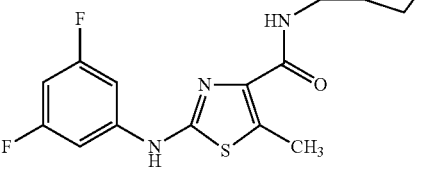

2-(3,5-difluoroanilino)-N-(6,6-dimethyl-7-bicyclo[3.2.0]heptanyl)-5-methyl-thiazole-4-carboxamide;

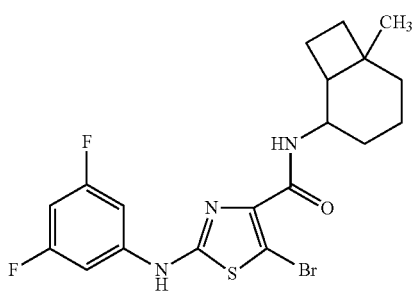 [SMILES: CC12CCCC(NC(=O)c3nc(Nc4cc(F)cc(F)c4)sc3Br)C1CC2]

5-bromo-2-(3,5-difluoroanilino)-N-(6-methyl-2-bicyclo[4.2.0]octanyl)thiazole-4-carboxamide;

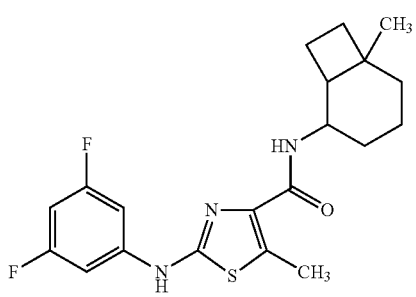 [SMILES: Cc1sc(Nc2cc(F)cc(F)c2)nc1C(=O)NC1CCCC2(C)CCC12]

2-(3,5-difluoroanilino)-5-methyl-N-(6-methyl-2-bicyclo[4.2.0]octanyl)thiazole-4-carboxamide.

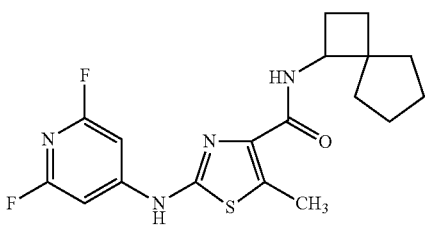

2-[(2,6-difluoro-4-pyridyl)amino]-5-methyl-N-spiro[3.4]octan-3-yl-thiazole-4-carboxamide;

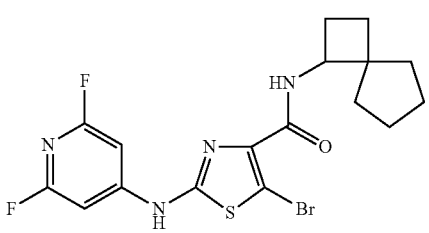 [SMILES: O=C(NC1CCC12CCCC2)c1nc(Nc2cc(F)nc(F)c2)sc1Br]

5-bromo-2-[(2,6-difluoro-4-pyridyl)amino]-N-spiro[3.4]octan-3-yl-thiazole-4-carboxamide;

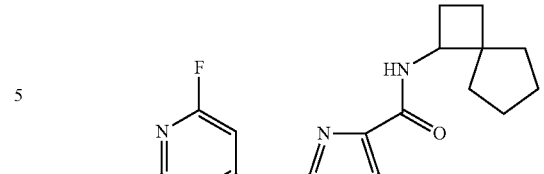

5-chloro-2-[(2,6-difluoro-4-pyridyl)amino]-N-spiro[3.4]octan-3-yl-thiazole-4-carboxamide;

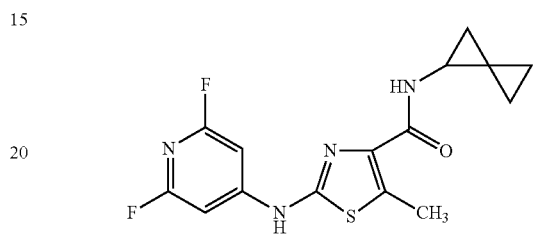

2-[(2,6-difluoro-4-pyridyl)amino]-5-methyl-N-spiro[2.2]pentan-2-yl-thiazole-4-carboxamide;

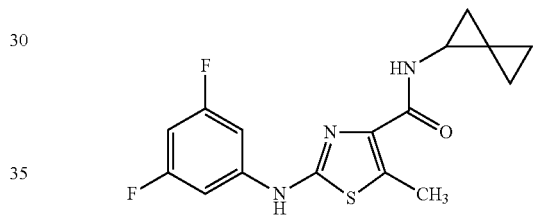

2-(3,5-difluoroanilino)-5-methyl-N-spiro[2.2]pentan-2-yl-thiazole-4-carboxamide; and

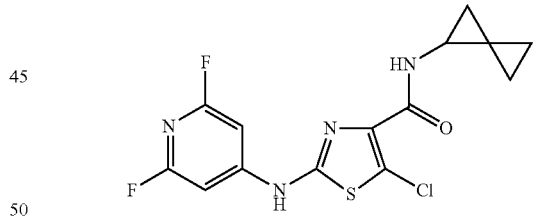

5-chloro-2-[(2,6-difluoro-4-pyridyl)amino]-N-spiro[2.2]pentan-2-yl-thiazole-4-carboxamide.

The invention also relates to compounds of formula I-1:

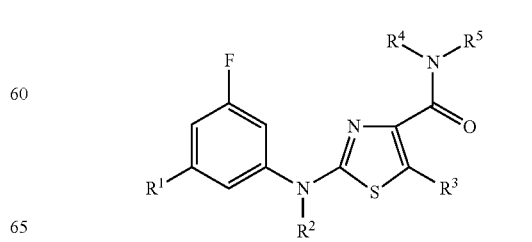

(I-1)

in which $R^1$, $R^2$, $R^3$, $R^4$ and $R^5$ have the definitions as described for formula I. Preferred definitions of $R^1$, $R^2$, $R^3$, $R^4$ and $R^5$ are as defined for formula (I).

The invention also relates to compounds of formula I-2:

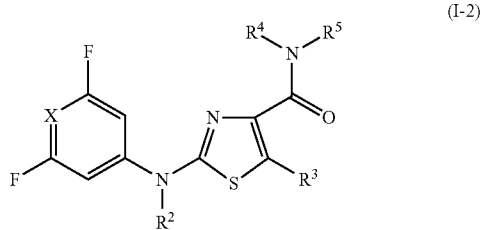

(I-2)

wherein $R^2$, $R^3$, $R^4$, $R^5$ and X have the definition as described for formula I. Preferred definitions of $R^2$, $R^3$, $R^4$, $R^5$ and X are as defined for formula (I).

The invention also relates to compounds of formula I-3:

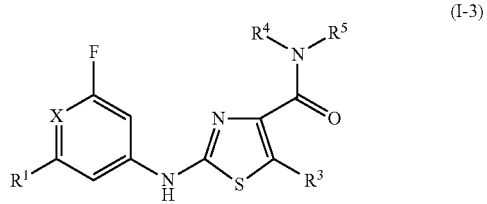

(I-3)

wherein $R^1$, $R^3$, $R^4$, $R^5$ and X have the definition as described for formula (I). Preferred definitions of $R^1$, $R^3$, $R^4$, $R^5$ and X are as defined for formula (I).

The invention also relates to compounds of formula I-4:

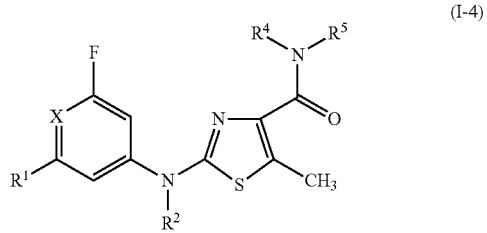

(I-4)

wherein $R^1$, $R^2$, $R^4$, $R^5$ and X have the definition as described for formula (I). Preferred definitions of $R^1$, $R^2$, $R^4$, $R^5$ and X are as defined for formula (I).

The invention also relates to compounds of formula I-5:

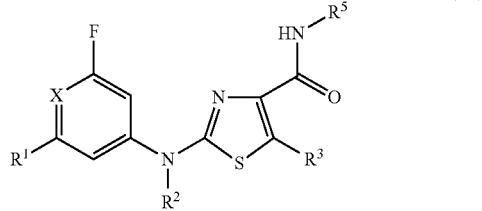

(I-5)

wherein $R^1$, $R^2$, $R^3$, $R^5$ and X have the definition as described for formula (I). Preferred definitions of $R^1$, $R^2$, $R^3$, $R^5$ and X are as defined for formula (I).

Further preferred embodiments of the present invention are the embodiments E-I.a to E-I.bk, which are defined as compounds of formula (I) which are represented by one formula selected from the group consisting of the formula (I.a) to (I.bk) as described below, wherein in formulae (I.a) to (I.bk) the meanings of the substituents $R^1$, $R^2$, $R^3$, $R^4$, $R^5$ and X have the preferred meanings as mentioned above or one of the meanings 1 to 80 given in the corresponding Table 1.

For example, embodiment E-I.a is represented by the compounds of formula (I.a)

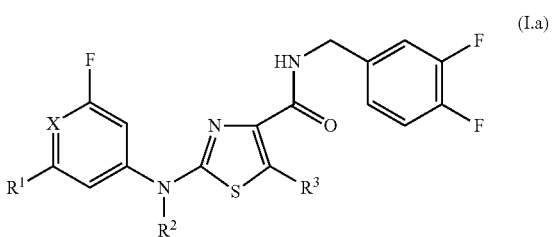

(I.a)

and the substituents $R^1$, $R^2$, $R^3$, $R^4$, $R^5$ and X have the meanings as defined above or one of the meanings 1 to 80 given in the Table 1.

Embodiments E-I.b to E-I.bk are defined accordingly and the substituents $R^1$, $R^2$, $R^3$, $R^4$, $R^5$ and X have the meanings as defined above or one of the meanings 1 to 80 given in the corresponding Table 1.

Compounds of the present invention can be made as shown in the following schemes, in which, unless otherwise stated, the definition of each variable is as defined above for a compound of formula (I).

The compounds of formula (I) according to the invention, wherein $R^1$, $R^2$, $R^3$, $R^4$, $R^5$ and X are as defined for formula (I), can be obtained by transformation of a compound of formula (II), wherein $R^1$, $R^2$ and X are as defined for formula (I), with a compound of formula (III), wherein $R^3$, $R^4$ and $R^5$ are as defined for formula (I) and $R^{12}$ is halogen, preferably bromo, either by thermal heating, or with the aid of a base or under the conditions of the transition metal catalysed Buchwald-Hartwig amination. This is shown in Scheme 1 below.

Scheme 1

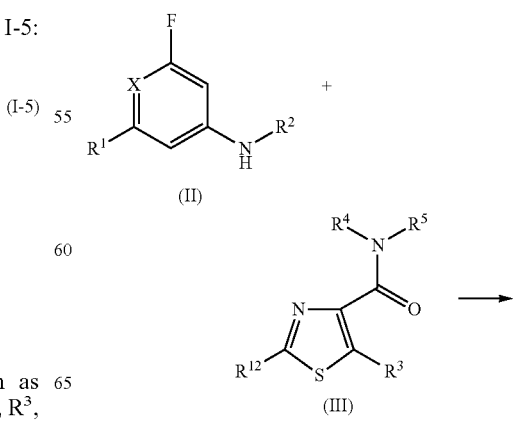

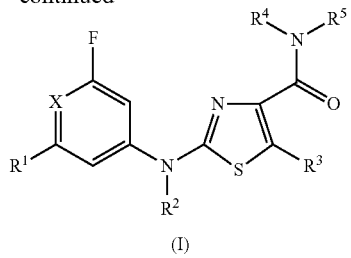

(I)

The compounds of formula (III), wherein $R^3$, $R^4$ and $R^5$ are as defined for formula (I) and $R^{12}$ is halogen, preferably bromo, can be obtained by transformation of a compound of formula (IV), wherein $R^3$ is as defined for formula (I) and $R^9$ is halogen, preferably bromo, and a compound of formula (V), wherein $R^4$ and $R^5$ are as defined for formula (I), either via an intermediate acid chloride or directly with an peptide coupling agent. This is shown in Scheme 2 below.

Scheme 2

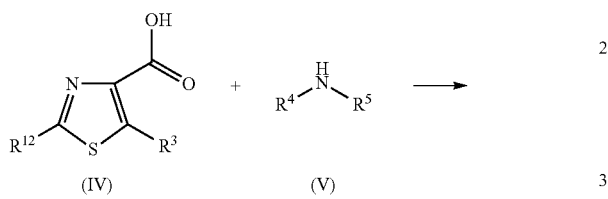

(IV)     (V)

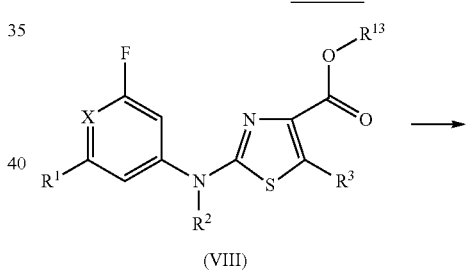

(III)

The compounds of formula (IV), wherein $R^3$ is as defined for formula (I) and $R^{12}$ is halogen, preferably bromo, can be obtained by transformation of a compound of formula (VI), wherein $R^3$ is as defined for formula (I), $R^{12}$ is halogen, preferably bromo, and $R^{13}$ is $C_1$-$C_6$alkyl, and with a base. This is shown in Scheme 3 below.

Scheme 3

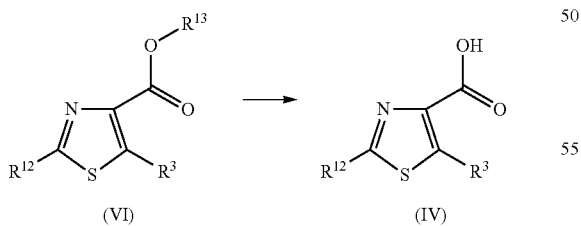

(VI)     (IV)

Alternatively, the compounds of formula (I), wherein $R^1$, $R^2$, $R^3$, $R^4$, $R^5$ and X are as defined for formula (I), can be obtained by transformation of a compound of formula (VII), wherein $R^1$, $R^2$, $R^3$ and X are as defined for formula (I), with a compound of formula (V), wherein $R^4$ and $R^5$ are as defined for formula (I), either via an intermediate acid chloride or directly with an peptide coupling agent. This is shown in Scheme 4 below.

Scheme 4

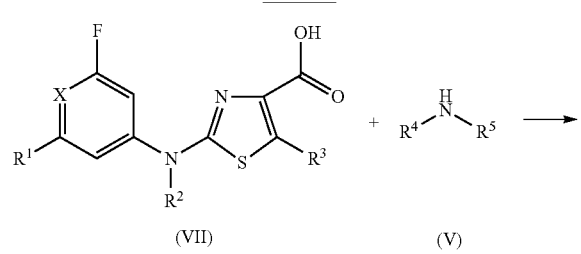

(VII)     (V)

(I)

The compounds of formula (VII), wherein $R^1$, $R^2$, $R^3$ and X are as defined for formula (I), can be obtained by transformation of a compound of formula (VIII), wherein $R^1$, $R^2$, $R^3$ and X are as defined for formula (I) and $R^{13}$ is $C_1$-$C_6$alkyl, and with a base. This is shown in Scheme 5 below.

Scheme 5

(VIII)

(VII)

The compounds of formula (VIII), wherein $R^1$, $R^2$, $R^3$ and X are as defined for formula (I) and $R^{13}$ is $C_1$-$C_6$alkyl, can be obtained by transformation of a compound of formula (II), wherein $R^1$, $R^2$ and X are as defined for formula (I), with a compound of formula (VI), wherein $R^3$ is as defined for formula (I), $R^{12}$ is halogen, preferably bromo, and $R^{13}$ is $C_1$-$C_6$alkyl, either by thermal heating, or with the aid of a base or under the conditions of the transition metal catalysed Buchwald-Hartwig amination. This is shown in Scheme 6 below.

Scheme 6

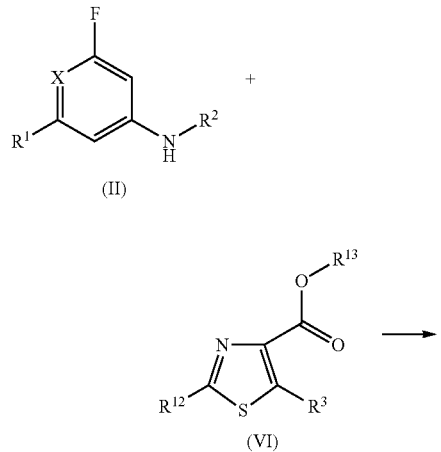

(II)

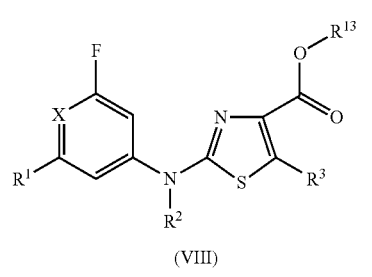

(VI)

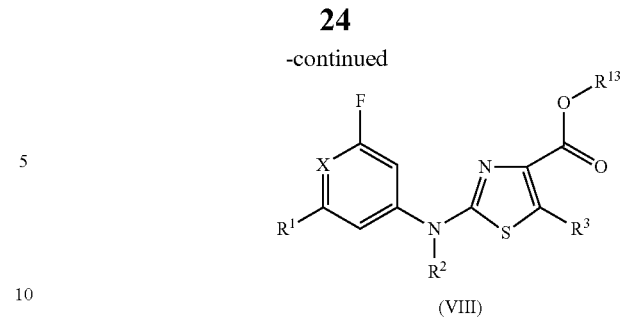

(VIII)

Alternatively, the compounds of formula (I) according to the invention, wherein $R^1$, $R^2$, $R^3$, $R^4$, $R^5$ and X are as defined for formula (I), can be obtained by transformation of a compound of formula (IX), wherein $R^1$ and X are as defined for formula (I) and $R^{12}$ is halogen, preferably bromo or iodo, with a compound of formula (XI), wherein $R^2$, $R^3$, $R^4$ and $R^5$ are as defined for formula (I), under the conditions of the transition metal catalysed Buchwald-Hartwig amination. This is shown in Scheme 8 below.

Scheme 8

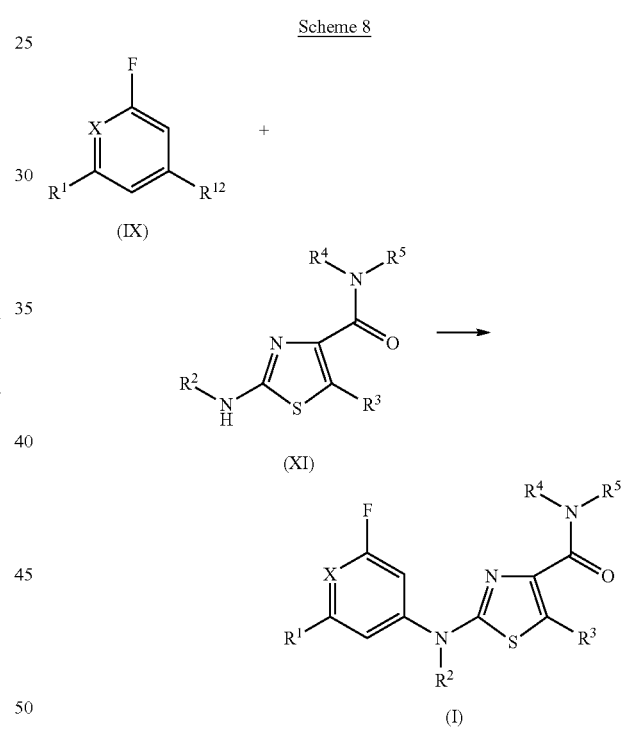

Alternatively, the compounds of formula (VIII), wherein $R^1$, $R^2$, $R^3$ and X are as defined for formula (I) and $R^{13}$ is $C_1$-$C_6$alkyl, can be obtained by transformation of a compound of formula (IX), wherein $R^1$ and X are as defined for formula (I) and $R^{12}$ is halogen, preferably bromo or iodo, with a compound of formula (X), wherein $R^2$ and $R^3$ and as defined for formula (I) and $R^{13}$ is $C_1$-$C_6$alkyl, under the conditions of the transition metal catalysed Buchwald-Hartwig amination. This is shown in Scheme 7 below.

Scheme 7

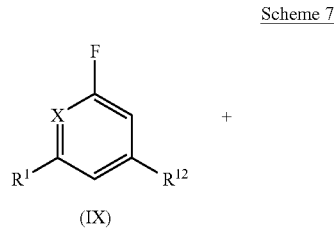

(IX)

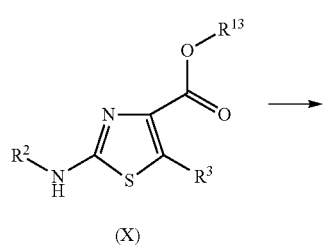

(X)

Surprisingly, it has now been found that the novel compounds of formula (I) have, for practical purposes, a very advantageous level of biological activity for protecting plants against diseases that are caused by fungi.

The compounds of formula (I) can be used in the agricultural sector and related fields of use, e.g., as active ingredients for controlling plant pests or on non-living materials for control of spoilage microorganisms or organisms potentially harmful to man. The novel compounds are distinguished by excellent activity at low rates of application, by being well tolerated by plants and by being environmentally safe. They have very useful curative, preventive and systemic properties and may be used for protecting numerous cultivated plants. The compounds of formula (I) can be used to inhibit or destroy the pests that occur on plants or parts of plants (fruit, blossoms, leaves, stems, tubers, roots) of different crops of useful plants, while at the same time protecting also those parts of the plants that grow later, e.g., from phytopathogenic microorganisms.

The present invention further relates to a method for controlling or preventing infestation of plants or plant propagation material and/or harvested food crops susceptible to microbial attack by treating plants or plant propagation material and/or harvested food crops wherein an effective amount a compound of formula (I) is applied to the plants, to parts thereof or the locus thereof.

It is also possible to use the compounds of formula (I) as fungicide. The term "fungicide" as used herein means a compound that controls, modifies, or prevents the growth of fungi. The term "fungicidally effective amount" means the quantity of such a compound or combination of such compounds that is capable of producing an effect on the growth of fungi. Controlling or modifying effects include all deviation from natural development, such as killing, retardation and the like, and prevention includes barrier or other defensive formation in or on a plant to prevent fungal infection.

It is also possible to use compounds of formula (I) as dressing agents for the treatment of plant propagation material, e.g., seed, such as fruits, tubers or grains, or plant cuttings (e.g., rice), for the protection against fungal infections, as well as against phytopathogenic fungi occurring in the soil. The propagation material can be treated with a composition comprising a compound of formula (I) before planting: seed, e.g., can be dressed before being sown.

The active ingredients according to the invention can also be applied to grains (coating), either by impregnating the seeds in a liquid formulation or by coating them with a solid formulation. The composition can also be applied to the planting site when the propagation material is being planted, e.g., to the seed furrow during sowing. The invention relates also to such methods of treating plant propagation material and to the plant propagation material so treated.

Furthermore, the compounds according to present invention can be used for controlling fungi in related areas, for example in the protection of technical materials, including wood and wood related technical products, in food storage, in hygiene management.

In addition, the invention could be used to protect non-living materials from fungal attack, e.g., lumber, wall boards and paint.

The compounds of formula (I) may be, for example, effective against fungi and fungal vectors of disease as well as phytopathogenic bacteria and viruses. These fungi and fungal vectors of disease as well as phytopathogenic bacteria and viruses are for example:

*Absidia corymbifera, Alternaria* spp, *Aphanomyces* spp, *Ascochyta* spp, *Aspergillus* spp. including *A. flavus, A. fumigatus, A. nidulans, A. niger, A. terrus, Aureobasidium* spp. including *A. pullulans, Blastomyces dermatitidis, Blumeria graminis, Bremia lactucae, Botryosphaeria* spp. including *B. dothidea, B. obtusa, Botrytis* spp. inclusing *B. cinerea, Candida* spp. including *C. albicans, C. glabrata, C. krusei, C. lusitaniae, C. parapsilosis, C. tropicalis, Cephaloascus fragrans,* Ceratocystis spp, *Cercospora* spp. including *C. arachidicola, Cercosporidium personatum, Cladosporium* spp, *Claviceps purpurea, Coccidioides immitis, Cochliobolus* spp, *Colletotrichum* spp. including *C. musae, Cryptococcus neoformans, Diaporthe* spp, *Didymella* spp, *Drechslera* spp, *Elsinoe* spp, *Epidermophyton* spp, *Erwinia amylovora, Erysiphe* spp. including *E. cichoracearum, Eutypa lata, Fusarium* spp. including *F. culmorum, F. graminearum, F. langsethiae, F. moniliforme, F. oxysporum, F. proliferatum, F. subglutinans, F. solani, Gaeumannomyces graminis, Gibberella fujikuroi, Gloeodes pomigena, Gloeosporium musarum, Glomerella cingulate, Guignardia bidwellii, Gymnosporangium juniperi-virginianae, Helminthosporium* spp, *Hemileia* spp, *Histoplasma* spp. including *H. capsulatum, Laetisaria fuciformis, Leptographium lindbergi, Leveillula taurica, Lophodermium seditiosum, Microdochium nivale, Microsporum* spp, *Monilinia* spp, *Mucor* spp, *Mycosphaerella* spp. including *M. graminicola, M. pomi, Oncobasidium theobromaeon, Ophiostoma piceae, Paracoccidioides* spp, *Penicillium* spp. including *P. digitatum, P. italicum, Petriellidium* spp, *Peronosclerospora* spp. Including *P. maydis, P. philippinensis* and *P. sorghi, Peronospora* spp, *Phaeosphaeria nodorum, Phakopsora pachyrhizi, Phellinus igniarus, Phialophora* spp, *Phoma* spp, *Phomopsis viticola, Phytophthora* spp. including *P. infestans, Plasmopara* spp. including *P. halstedii, P. viticola, Pleospora* spp., *Podosphaera* spp. including *P. leucotricha, Polymyxa graminis, Polymyxa betae, Pseudocercosporella herpotrichoides, Pseudomonas* spp, *Pseudoperonospora* spp. including *P. cubensis, P. humuli, Pseudopeziza tracheiphila, Puccinia* Spp. including *P. hordei, P. recondita, P. striiformis, P. triticina, Pyrenopeziza* spp, *Pyrenophora* spp, *Pyricularia* spp. including *P. oryzae, Pythium* spp. including *P. ultimum, Ramularia* spp, *Rhizoctonia* spp, *Rhizomucor pusillus, Rhizopus arrhizus, Rhynchosporium* spp, *Scedosporium* spp. including *S. apiospermum* and *S. prolificans, Schizothyrium pomi, Sclerotinia* spp, *Sclerotium* spp, *Septoria* spp, including *S. nodorum, S. tritici, Sphaerotheca macularis, Sphaerotheca fusca (Sphaerotheca fuliginea), Sporothorix* spp, *Stagonospora nodorum, Stemphylium* spp., *Stereum hirsutum, Thanatephorus cucumeris, Thielaviopsis basicola, Tilletia* spp, *Trichoderma* spp., including *T. harzianum, T. pseudokoningii, T. viride, Trichophyton* spp, *Typhula* spp, *Uncinula necator, Urocystis* spp, *Ustilago* spp, *Venturia* spp. including *V. inaequalis, Verticillium* spp, and *Xanthomonas* spp.

Within the scope of present invention, target crops and/or useful plants to be protected typically comprise perennial and annual crops, such as berry plants for example blackberries, blueberries, cranberries, raspberries and strawberries; cereals for example barley, maize (corn), millet, oats, rice, rye, sorghum triticale and wheat; fibre plants for example cotton, flax, hemp, jute and sisal; field crops for example sugar and fodder beet, coffee, hops, mustard, oilseed rape (canola), poppy, sugar cane, sunflower, tea and tobacco; fruit trees for example apple, apricot, avocado, banana, cherry, citrus, nectarine, peach, pear and plum; grasses for example Bermuda grass, bluegrass, bentgrass, centipede grass, fescue, ryegrass, St. Augustine grass and Zoysia grass; herbs such as basil, borage, chives, coriander, lavender, lovage, mint, oregano, parsley, rosemary, sage and thyme; legumes for example beans, lentils, peas and soya beans; nuts for example almond, cashew, ground nut, hazelnut, peanut, pecan, pistachio and walnut; palms for example oil palm; ornamentals for example flowers, shrubs and trees; other trees, for example cacao, coconut, olive and rubber; vegetables for example asparagus, aubergine, broccoli, cabbage, carrot, cucumber, garlic, lettuce, marrow, melon, okra, onion, pepper, potato, pumpkin, rhubarb, spinach and tomato; and vines for example grapes.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus Bacillus.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus Bacillus.

Toxins that can be expressed by such transgenic plants include, for example, insecticidal proteins from Bacillus cereus or Bacillus popilliae; or insecticidal proteins from Bacillus thuringiensis, such as 8-endotoxins, e.g. CryIAb, CryIAc, CryIF, CryIFa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example Photorhabdus spp. or Xenorhabdus spp., such as Photorhabdus luminescens, Xenorhabdus nematophilus; toxins produced by animals, such as scorpion toxins, arachnid toxins, wasp toxins and other insect-specific neurotoxins; toxins produced by fungi, such as Streptomycetes toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by 8-endotoxins, for example CryIAb, CryIAc, CryIF, CryIFa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated CryIAb, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIAb toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard II® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified Zea mays which has been rendered resistant to attack by the European corn borer (Ostrinia nubilalis and Sesamia nonagrioides) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified Zea mays which has been rendered resistant to attack by the European corn borer (Ostrinia nubilalis and Sesamia nonagrioides) by transgenic expression of a Cry1Ab toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIAb toxin obtained from *Bacillus thuringiensis* subsp. *kurstaki* which brings about tolerance to certain Lepidoptera, include the European corn borer.

The term "locus" as used herein means fields in or on which plants are growing, or where seeds of cultivated plants are sown, or where seed will be placed into the soil. It includes soil, seeds, and seedlings, as well as established vegetation.

The term "plants" refers to all physical parts of a plant, including seeds, seedlings, saplings, roots, tubers, stems, stalks, foliage, and fruits.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

Pesticidal agents referred to herein using their common name are known, for example, from "The Pesticide Manual", 15th Ed., British Crop Protection Council 2009.

The compounds of formula (I) may be used in unmodified form or, preferably, together with the adjuvants conventionally employed in the art of formulation. To this end, they may be conveniently formulated in known manner to emulsifiable concentrates, coatable pastes, directly sprayable or dilutable solutions or suspensions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants, e.g., for agricultural use, can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula (I) are normally used in the form of compositions and can be applied to the crop area or plant to be treated, simultaneously or in succession with further compounds. These further compounds can be, e.g., fertilizers or micronutrient donors or other preparations, which influence the growth of plants. They can also be selective herbicides or non-selective herbicides as well as insecticides, fungicides, bactericides, nematicides, molluscicides or mixtures of several of these preparations, if desired together with further carriers, surfactants or application promoting adjuvants customarily employed in the art of formulation.

The compounds of formula (I) may be used in the form of (fungicidal) compositions for controlling or protecting against phytopathogenic microorganisms, comprising as active ingredient at least one compound of formula (I) or of at least one preferred individual compound as above-defined, in free form or in agrochemically usable salt form, and at least one of the above-mentioned adjuvants.

The invention provides a composition, preferably a fungicidal composition, comprising at least one compound formula (I) an agriculturally acceptable carrier and optionally an adjuvant. An agricultural acceptable carrier is for example a carrier that is suitable for agricultural use. Agricultural carriers are well known in the art. Preferably, said composition may comprise at least one or more pesticidally active compounds, for example an additional fungicidal active ingredient in addition to the compound of formula (I).

The compound of formula (I) may be the sole active ingredient of a composition or it may be admixed with one or more additional active ingredients such as a pesticide, fungicide, synergist, herbicide or plant growth regulator where appropriate. An additional active ingredient may, in some cases, result in unexpected synergistic activities.

Examples of suitable additional active ingredients include the following acycloamino acid fungicides, aliphatic nitrogen fungicides, amide fungicides, anilide fungicides, antibiotic fungicides, aromatic fungicides, arsenical fungicides, aryl phenyl ketone fungicides, benzamide fungicides, benzanilide fungicides, benzimidazole fungicides, benzothiazole fungicides, botanical fungicides, bridged diphenyl fungicides, carbamate fungicides, carbanilate fungicides, conazole fungicides, copper fungicides, dicarboximide fungicides, dinitrophenol fungicides, dithiocarbamate fungicides, dithiolane fungicides, furamide fungicides, furanilide fungicides, hydrazide fungicides, imidazole fungicides, mercury fungicides, morpholine fungicides, organophosphorous fungicides, organotin fungicides, oxathiin fungicides, oxazole fungicides, phenylsulfamide fungicides, polysulfide fungicides, pyrazole fungicides, pyridine fungicides, pyrimidine fungicides, pyrrole fungicides, quaternary ammonium fungicides, quinoline fungicides, quinone fungicides, quinoxaline fungicides, strobilurin fungicides, sulfonanilide fungicides, thiadiazole fungicides, thiazole fungicides, thiazolidine fungicides, thiocarbamate fungicides, thiophene fungicides, triazine fungicides, triazole fungicides, triazolopyrimidine fungicides, urea fungicides, valinamide fungicides, and zinc fungicides.

Examples of suitable additional active ingredients also include the following: 3-difluoromethyl-1-methyl-1H-pyrazole-4-carboxylic acid (9-dichloromethylene-1,2,3,4-tetrahydro-1,4-methano-naphthalen-5-yl)-amide, 3-difluoromethyl-1-methyl-1H-pyrazole-4-carboxylic acid methoxy-[1-methyl-2-(2,4,6-trichlorophenyl)-ethyl]-amide, 1-methyl-3-difluoromethyl-1H-pyrazole-4-carboxylic acid (2-dichloromethylene-3-ethyl-1-methyl-indan-4-yl)-amide (1072957-71-1), 1-methyl-3-difluoromethyl-1H-pyrazole-4-carboxylic acid (4'-methylsulfanyl-biphenyl-2-yl)-amide, 1-methyl-3-difluoromethyl-4H-pyrazole-4-carboxylic acid [2-(2,4-dichloro-phenyl)-2-methoxy-1-methyl-ethyl]-amide, (5-Chloro-2,4-dimethyl-pyridin-3-yl)-(2,3,4-trimethoxy-6-methyl-phenyl)-methanone, (5-Bromo-4-chloro-2-methoxy-pyridin-3-yl)-(2,3,4-trimethoxy-6-methyl-phenyl)-methanone, 2-{2-[(E)-3-(2,6-Dichlorophenyl)-1-methyl-prop-2-en-(E)-ylideneaminooxymethyl]-phenyl}-2-[(Z)-methoxyimino]-N-methyl-acetamide, 3-[5-(4-Chloro-phenyl)-2,3-dimethyl-isoxazolidin-3-yl]-pyridine, (E)-N-methyl-2-[2-(2,5-dimethylphenoxymethyl)phenyl]-2-methoxy-iminoacetamide, 4-bromo-2-cyano-N,N-dimethyl-6-trifluoromethylbenzimidazole-1-sulphonamide, a-[N-(3-chloro-2, 6-xylyl)-2-methoxyacetamido]-y-butyrolactone, 4-chloro-2-cyano-N,-dimethyl-5-p-tolylimidazole-1-sulfonamide, N-allyl-4, 5,-dimethyl-2-trimethylsilylthiophene-3-carboxamide, N— (I-cyano-1, 2-dimethylpropyl)-2-(2, 4-dichlorophenoxy) propionamide, N-(2-methoxy-5-pyridyl)-cyclopropane carboxamide, (.+-.)-cis-1-(4-chlorophenyl)-2-(1H-1,2,4-triazol-1-yl)-cycloheptanol, 2-(1-tert-butyl)-1-(2-chlorophenyl)-3-(1,2,4-triazol-1-yl)-propan-2-ol, 2',6'-dibromo-2-methyl-4-trifluoromethoxy-4'-trifluoromethyl-1,3-thiazole-5-carboxanilide, 1-imidazolyl-1-(4'-chlorophenoxy)-3,3-dimethylbutan-2-one, methyl (E)-2-[2-[6-(2-cyanophenoxy)pyrimidin-4-yloxy]phenyl]3-methoxyacrylate, methyl (E)-2-[2-[6-(2-thioamidophenoxy)pyrimidin-4-yloxy]phenyl]-3-methoxyacrylate, methyl (E)-2-[2-[6-(2-fluorophenoxy)pyrimidin-4-yloxy]phenyl]-3-methoxyacrylate, methyl (E)-2-[2-[6-(2,6-difluorophenoxy)pyrimidin-4-yloxy]phenyl]-3-methoxyacrylate, methyl (E)-2-[2-[3-(pyrimidin-2-yloxy)phenoxy]phenyl]-3-methoxyacrylate, methyl (E)-2-[2-[3-(5-m ethylpyrimidin-2-yloxy)-phenoxy]phenyl]-3-methoxyacrylate, methyl (E)-2-[2-[3-(phenyl-sulphonyloxy)phenoxy]phenyl-3-methoxyacrylate, methyl (E)-2-[2-[3-(4-nitrophenoxy)phenoxy]phenyl]-3-methoxyacrylate, methyl (E)-2-[2-phenoxyphenyl]-3-methoxyacrylate, methyl (E)-2-[2-(3,5-dimethyl-benzoyl)pyrrol-1-yl]-3-methoxyacrylate, methyl (E)-2-[2-(3-methoxyphenoxy)phenyl]-3-methoxyacrylate, methyl (E)-2[2-(2-phenylethen-1-yl)-phenyl]-3-methoxyacrylate, methyl (E)-2-[2-(3,5-dichlorophenoxy)pyridin-3-yl]-3-methoxyacrylate, methyl (E)-2-(2-(3-(1,1,2,2-tetrafluoroethoxy)phenoxy)phenyl)-3-methoxyacrylate, methyl (E)-2-(2-[3-(alpha-hydroxybenzyl)phenoxy]phenyl)-3-methoxyacrylate, methyl (E)-2-(2-(4-phenoxypyridin-2-yloxy)phenyl)-3-methoxyacrylate, methyl (E)-2-[2-(3-n-propyloxy-phenoxy)phenyl]3-methoxyacrylate, methyl (E)-2-[2-(3-isopropyloxyphenoxy)phenyl]-3-methoxyacrylate, methyl (E)-2-[2-[3-(2-fluoro-phenoxy)phenoxy]phenyl]-3-methoxyacrylate, methyl (E)-2-[2-(3-ethoxyphenoxy)phenyl]-3-methoxyacrylate, methyl (E)-2-[2-(4-tert-butyl-pyridin-2-yloxy)phenyl]-3-methoxyacrylate, methyl (E)-2-[2-[3-(3-cyanophenoxy)phenoxy]phenyl]-3-methoxyacrylate, methyl (E)-2-[(3-methyl-pyridin-2-yloxymethyl)phenyl]-3-m ethoxyacrylate, methyl (E)-2-[2-[6-(2-methyl-phenoxy)pyrimidin-4-yloxy]phenyl]-3-m ethoxyacrylate, methyl (E)-2-[2-(5-bromo-pyridin-2-yloxymethyl)phenyl]-3-methoxyacrylate, methyl (E)-2-[2-(3-(3-iodopyridin-2-yloxy)phenoxy)phenyl]-3-methoxyacrylate, methyl (E)-2-[2-[6-(2-chloropyridin-3-yloxy)pyrimidin-4-yloxy]phenyl]-3-methoxyacrylate, methyl (E),(E)-2-[2-(5,6-dimethylpyrazin-2-ylmethyloximinomethyl)phenyl]-3-methoxyacrylate, methyl (E)-2-{2-[6-(6-methylpyridin-2-yloxy)pyrimidin-4-yloxy]phenyl}-3-methoxy-crylate, methyl (E),(E)-2-{2-(3-m ethoxyphenyl) methyloximinomethyl]-phenyl}-3-methoxyacrylate, methyl (E)-2-{2-[(6-(2-azidophenoxy)-pyrimidin-4-yloxy]phenyl}-3-methoxyacrylate, methyl (E),(E)-2-{2-[6-phenylpyrimidin-4-yl)-methyloximinomethyl]phenyl}-3-methoxyacrylate, methyl (E),(E)-2-{2-[(4-chlorophenyl)-methyloximinomethyl]-phenyl}-3-methoxyacrylate, methyl (E)-2-{2-[6-(2-n-propylphenoxy)-1,3,5-triazin-4-yloxy]phenyl}-3-methoxyacrylate, methyl (E),(E)-2-{2-[(3-nitrophenyl)methyloximinomethyl]phenyl}-3-methoxyacrylate, 3-chloro-7-(2-aza-2,7,7-trimethyl-oct-3-en-5-ine), 2,6-dichloro-N-(4-trifluoromethylbenzyl)-benzamide, 3-iodo-2-propinyl alcohol, 4-chlorophenyl-3-iodopropargyl formal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butylcarbamate, 3-iodo-2-propinyl n-hexylcarbamate, 3-iodo-2-propinyl cyclohexyl-carbamate, 3-iodo-2-propinyl phenylcarbamate; phenol derivatives, such as tribromophenol, tetrachlorophenol, 3-methyl-4-chlorophenol, 3,5-dimethyl-4-chlorophenol, phenoxyethanol, dichlorophene, o-phenylphenol, m-phenylphenol, p-phenylphenol, 2-benzyl-4-chlorophenol, 5-hydroxy-2(5H)-furanone; 4,5-dichlorodithiazolinone, 4,5-benzodithiazolinone, 4,5-trimethylenedithiazolinone, 4,5-dichloro-(3H)-1,2-dithiol-3-one, 3,5-dimethyl-tetrahydro-1,3,5-thiadiazine-2-thione, N-(2-p-chlorobenzoylethyl)-hexaminium chloride, acibenzolar, acypetacs, alanycarb, albendazole, aldimorph, allicin, allyl alcohol, ametoctradin, amisulbrom, amobam, ampropylfos, anilazine, asomate, aureofungin, azaconazole, azafendin, azithiram, azoxystrobin, barium polysulfide, benalaxyl, benalaxyl-M, benodanil, benomyl, benquinox, bentaluron, benthiavalicarb, benthiazole, benzalkonium chloride, benzamacril, benzamorf, benzohydroxamic acid, benzovindiflupyr, berberine, bethoxazin, biloxazol, binapacryl, biphenyl, bitertanol, bithionol, bixafen, blasticidin-S, boscalid, bromothalonil, bromuconazole, bupirimate, buthiobate, butylamine calcium polysulfide, captafol, captan, carbamorph, carbendazim, carbendazim chlorhydrate, carboxin, carpropamid, carvone, CGA41396, CGA41397, chinomethionate, chitosan, chlobenthiazone, chloraniformethan, chloranil, chlorfenazole, chloroneb, chloropicrin, chlorothalonil, chlorozolinate, chlozolinate, climbazole, clotrimazole, clozylacon, copper containing compounds such as copper acetate, copper carbonate, copper hydroxide, copper naphthenate, copper oleate, copper oxychloride, copper oxyquinolate, copper silicate, copper sulphate, copper tallate, copper zinc chromate and Bordeaux mixture, cresol, cufraneb, cuprobam, cuprous oxide, cyazofamid, cyclafuramid, cycloheximide, cyflufenamid, cymoxanil, cypendazole, cyproconazole, cyprodinil, dazomet, debacarb, decafentin, dehydroacetic acid, di-2-pyridyl disulphide 1, 1'-dioxide, dichlofluanid, diclomezine, dichlone, dichloran, dichlorophen, dichlozoline, diclobutrazol, diclocymet, diethofencarb, difenoconazole, difenoquat, diflumetorim, O-di-iso-propyl-S-benzyl thiophosphate, dimefluazole, dimethachlone, dimetconazole, dimethomorph, dimethirimol, diniconazole, diniconazole-M, dinobuton, dinocap, dinocton, dinopenton, dinosulfon, dinoterbon, diphenylamine, dipyrithione, disulfiram, ditalimfos, dithianon, dithioether, dodecyl dimethyl ammonium chloride, dodemorph, dodicin, dodine, doguadine, drazoxolon, edifenphos, enestroburin, epoxiconazole, etaconazole, etem, ethaboxam, ethirimol, ethoxyquin, ethilicin, ethyl (Z)—N-benzyl-N([methyl (methyl-thioethylideneamino-oxycarbonyl) amino]thio)-ß-alaninate, etridiazole, famoxadone, fenamidone, fenaminosulf, fenapanil, fenarimol, fenbuconazole, fenfuram, fenhexamid, fenitropan, fenoxanil, fenpiclonil, fenpicoxamid, fenpropidin, fenpropimorph, fenpyrazamine, fentin acetate, fentin hydroxide, ferbam, ferimzone, fluazinam, fludioxonil, flumetover, flumorph, flupicolide, fluopyram, fluoroimide, fluotrimazole, fluoxastrobin, fluquinconazole, flusilazole, flusulfamide, flutanil, flutolanil, flutriafol, fluxapyroxad, folpet, formaldehyde, fosetyl, fuberidazole, furalaxyl, furametpyr, furcarbanil, furconazole, furfural, furmecyclox, furophanate, glyodin, griseofulvin, guazatine, halacrinate, hexachlorobenzene, hexachlorobutadiene, hexachlorophene, hexaconazole, hexylthiofos, hydrargaphen, hydroxyisoxazole, hymexazole, imazalil, imazalil sulphate, imibenconazole, iminoctadine, iminoctadine triacetate, inezin, iodocarb, ipconazole, ipfentrifluconazole, iprobenfos, iprodione, iprovalicarb, isopropanyl butyl carbamate, isoprothiolane, isopyrazam, isotianil, isovaledione, izopamfos, kasugamycin, kresoxim-methyl, LY186054, LY211795, LY248908, mancozeb, mandiprop-amid, maneb, mebenil, mecarbinzid, mefenoxam, mefentrifluconazole, mepanipyrim, mepronil, mercuric chloride, mercurous chloride, meptyldinocap, metalaxyl, metalaxyl-M, metam, metazoxolon, metconazole, methasulfocarb, methfuroxam, methyl bromide, methyl iodide, methyl isothiocyanate, metiram, metiram-zinc, metominostrobin, metrafenone, metsulfovax, milneb, moroxydine, myclobutanil, myclozolin, nabam, natamycin, neoasozin, nickel dimethyldithiocarbamate, nitrostyrene, nitrothal-iso-propyl, nuarimol, octhilinone, ofurace, organomercury compounds, orysastrobin, osthol, oxadixyl, oxasulfuron, oxathiapiprolin, oxine-copper, oxolinic acid, oxpoconazole, oxycarboxin, parinol, pefurazoate, penconazole, pencycuron, penflufen, pentachlorophenol, penthiopyrad, phenamacril, phenazin oxide, phosdiphen, phosetyl-AI, phosphorus acids, phthalide, picoxystrobin, piperalin, polycarbamate, polyoxin D, polyoxrim, polyram, probenazole, prochloraz, procymidone, propamidine, propamocarb, propiconazole, propineb, propionic acid, proquinazid, prothiocarb, prothioconazole, pydiflumetofen, pyracarbolid, pyraclostrobin, pyrametrostrobin, pyraoxystrobin, pyrazophos, pyribencarb, pyridinitril, pyrifenox, pyrimethanil, pyriofenone, pyroquilon, pyroxychlor, pyroxyfur, pyrrolnitrin, quaternary ammonium compounds, quinacetol, quinazamid, quinconazole, quinomethionate, quinoxyfen, quintozene, rabenzazole, santonin, sedaxane, silthiofam, simeconazole, sipconazole, sodium pentachlorophenate, spiroxamine, streptomycin, sulphur, sultropen, tebuconazole, tebfloquin, tecloftalam, tecnazene, tecoram, tetraconazole, thiabendazole, thiadifluor, thicyofen, thifluzamide, 2-(thiocyanomethylthio) benzothiazole, thiophanate-methyl, thioquinox, thiram, tiadinil, timibenconazole, tioxymid, tolclofos-methyl, tolylfluanid, triadimefon, triadimenol, triamiphos, triarimol, triazbutil, triazoxide, tricyclazole, tridemorph, trifloxystrobin, triflumazole, triforine, triflumizole, triticonazole, uniconazole, urbacide, validamycin, valifenalate, vapam, vinclozolin, zarilamid, zineb, ziram, and zoxamide.

The compounds of the invention may also be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in U.S. Pat. No. 5,015,630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

The compounds of the invention may be used in combination with derivatives and analogues of the paraherquamide/marcfortine class of anthelmintic agents, as well as the antiparasitic oxazolines such as those disclosed in U.S. Pat. Nos. 5,478,855, 4,639,771 and DE-19520936.

The compounds of the invention may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

The compounds of the invention may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

The compounds of the invention may be used in combination with terpene alkaloids, for example those described in WO 95/19363 or WO 04/72086, particularly the compounds disclosed therein.

Other examples of such biologically active compounds that the compounds of the invention may be used in combination with include but are not restricted to the following:

Organophosphates: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl(methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)

(1 R)-cis-2,2-dimethyl-3-(2-oxothiolan-3-ylidenemethyl) cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, lambda-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, *Bacillus thuringiensis*, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195,RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Biological agents: *Bacillus thuringiensis* ssp *aizawai, kurstaki, Bacillus thuringiensis* delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

Another aspect of invention is related to the use of a compound of formula (I) or of a preferred individual compound as above-defined, of a composition comprising at least one compound of formula (I) or at least one preferred individual compound as above-defined, or of a fungicidal or insecticidal mixture comprising at least one compound of formula (I) or at least one preferred individual compound as above-defined, in admixture with other fungicides or insecticides as described above, for controlling or preventing infestation of plants, e.g. useful plants such as crop plants, propagation material thereof, e.g. seeds, harvested crops, e.g., harvested food crops, or non-living materials by insects or by phytopathogenic microorganisms, preferably fungal organisms.

A further aspect of invention is related to a method of controlling or preventing an infestation of plants, e.g., useful plants such as crop plants, propagation material thereof, e.g. seeds, harvested crops, e.g. harvested food crops, or of non-living materials by insects or by phytopathogenic or spoilage microorganisms or organisms potentially harmful to man, especially fungal organisms, which comprises the application of a compound of formula (I) or of a preferred individual compound as above-defined as active ingredient to the plants, to parts of the plants or to the locus thereof, to the propagation material thereof, or to any part of the non-living materials.

Controlling or preventing means reducing infestation by insects or by phytopathogenic or spoilage microorganisms or organisms potentially harmful to man, especially fungal organisms, to such a level that an improvement is demonstrated.

A preferred method of controlling or preventing an infestation of crop plants by phytopathogenic microorganisms, especially fungal organisms, or insects which comprises the application of a compound of formula (I), or an agrochemical composition which contains at least one of said compounds, is foliar application. The frequency of application and the rate of application will depend on the risk of infestation by the corresponding pathogen or insect. However, the compounds of formula (I) can also penetrate the plant through the roots via the soil (systemic action) by drenching the locus of the plant with a liquid formulation, or by applying the compounds in solid form to the soil, e.g., in granular form (soil application). In crops of water rice such granulates can be applied to the flooded rice field. The compounds of formula (I) may also be applied to seeds (coating) by impregnating the seeds or tubers either with a liquid formulation of the fungicide or coating them with a solid formulation.

A formulation, e.g. a composition containing the compound of formula (I), and, if desired, a solid or liquid adjuvant or monomers for encapsulating the compound of formula (I), may be prepared in a known manner, typically by intimately mixing and/or grinding the compound with extenders, for example solvents, solid carriers and, optionally, surface active compounds (surfactants).

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

When the combinations of the present invention are used for treating seed, rates of 0.001 to 50 g of a compound of formula (I) per kg of seed, preferably from 0.01 to 10 g per kg of seed are generally sufficient.

The compositions of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Such compositions may be produced in conventional manner, e.g., by mixing the active ingredients with appropriate formulation inerts (diluents, solvents, fillers and optionally other formulating ingredients such as surfactants, biocides, anti-freeze, stickers, thickeners and compounds that provide adjuvancy effects). Also conventional slow release formulations may be employed where long lasting efficacy is intended. Particularly formulations to be applied in spraying forms, such as water dispersible concentrates (e.g. EC, SC, DC, OD, SE, EW, EO and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

A seed dressing formulation is applied in a manner known per se to the seeds employing the combination of the invention and a diluent in suitable seed dressing formulation form, e.g., as an aqueous suspension or in a dry powder form having good adherence to the seeds. Such seed dressing formulations are known in the art. Seed dressing formulations may contain the single active ingredients or the combination of active ingredients in encapsulated form, e.g. as slow release capsules or microcapsules.

In general, the formulations include from 0.01 to 90% by weight of active agent, from 0 to 20% agriculturally acceptable surfactant and 10 to 99.99% solid or liquid formulation inerts and adjuvant(s), the active agent consisting of at least the compound of formula (I) together with component (B) and (C), and optionally other active agents, particularly microbiocides or conservatives or the like. Concentrated forms of compositions generally contain in between about 2 and 80%, preferably between about 5 and 70% by weight of active agent. Application forms of formulation may for example contain from 0.01 to 20% by weight, preferably from 0.01 to 5% by weight of active agent. Whereas commercial products will preferably be formulated as concentrates, the end user will normally employ diluted formulations.

EXAMPLES

The Examples which follow serve to illustrate the invention. The compounds of the invention can be distinguished from known compounds by virtue of greater efficacy at low application rates, which can be verified by the person skilled in the art using the experimental procedures outlined in the Examples, using lower application rates if necessary, for example 50 ppm, 12.5 ppm, 6 ppm, 3 ppm, 1.5 ppm, 0.8 ppm or 0.2 ppm.

Compounds of Formula (I) may possess any number of benefits including, inter alia, advantageous levels of biological activity for protecting plants against diseases that are caused by fungi or superior properties for use as agrochemical active ingredients (for example, greater biological activity, an advantageous spectrum of activity, an increased safety profile (including improved crop tolerance), improved physico-chemical properties, or increased biodegradability).

Example 1

This example illustrates the preparation of N-(1-cyano-1, 2-dimethyl-propyl)-2-(3,5-difluoroanilino)-5-methyl-thiazole-4-carboxamide (Compound I.n.3)

a) Preparation of methyl 2-(3,5-difluoroanilino)-5-methyl-thiazole-4-carboxylate A mixture of methyl 2-bromo-5-methyl-thiazole-4-carboxylate (5.0 g, 20 mmol) and 3,5-difluoroaniline (13.3 g, 101 mmol) were heated to 130° C. for 1 h under stirring. The reaction mixture was cooled to room temperature and diluted with ethyl acetate and water. The phases were separated, the aqueous phase was extracted with ethyl acetate, the combined organic layer was washed with water and brine, dried over magnesium sulfate and evaporated under reduced pressure. The residue was purified by chromatography on silica gel, using ethyl acetate and heptane as eluents, to deliver methyl 2-(3,5-difluoroanilino)-5-methyl-thiazole-4-carboxylate (4.9 g, 17 mmol). $^1$H-NMR (400 MHz, CDCl$_3$): $\delta$=2.73 (s, 3H), 3.94 (s, 3H), 6.52 (t, 1H), 6.86 (d, 2H), 7.43 (bs, 1H).

b) Preparation of 2-(3,5-difluoroanilino)-5-methyl-thiazole-4-carboxylic Acid

Lithium hydroxide monohydrate (1.7 g, 69 mmol) was added to a solution of methyl 2-(3,5-difluoroanilino)-5-methyl-thiazole-4-carboxylate (4.9 g, 17 mmol) in a mixture of 40 ml of tetrahydrofuran and 20 ml of water. The reaction mixture was stirred 16 h at room temperature, then the solvents were removed in vacuo. The residue was diluted with ethyl acetate and water, then 2 N hydrochloric acid was slowly added until a pH of 3-4 was reached. An insoluble solid was removed from the biphasic mixture by filtration and delivered a first batch of the desired product. The different phases of the filtrate were separated, the aqueous phase was extracted with ethyl acetate, the combined organic layer was washed with water and brine, dried over magnesium sulfate and evaporated under reduced pressure to deliver a second part of the desired product. Both solid batches were combined and dried in high-vacuum to deliver 2-(3,5-difluoroanilino)-5-methyl-thiazole-4-carboxylic acid (4.6 g, 16 mmol). $^1$H-NMR (400 MHz, MeOD): $\delta$=2.69 (s, 3H), 6.51 (t, 1H), 7.30 (d, 2H).

c) Preparation of N-(1-cyano-1,2-dimethyl-propyl)-2-(3,5-difluoroanilino)-5-methyl-thiazole-4-carboxamide (Compound I.n.3)

Triethylamine (0.22 g, 2.22 mmol) and propane phosphonic acid anhydride (T3P, 0.94 g, 1.48 mmol) were consecutively added to a solution of 2-(3,5-difluoroanilino)-5-methyl-thiazole-4-carboxylic acid (0.2 g, 0.74 mmol) in 10 ml of acetonitrile. The reaction mixture was stirred for 30 min at room temperature, then 2-amino-2,3-dimethylbutyronitrile (0.1 g, 0.89 mmol) was added. Stirring at room temperature was continued for 16 h, then the reaction mixture was diluted with ethyl acetate, washed with water, dried over magnesium sulfate and evaporated under reduced pressure. The residue was purified by chromatography on silica gel, using ethyl acetate and heptane as eluents, to deliver N-(1-cyano-1,2-dimethyl-propyl)-2-(3,5-difluoroanilino)-5-methyl-thiazole-4-carboxamide (Compound I.n.3, 0.14 g, 0.36 mmol). $^1$H-NMR (400 MHz, CDCl$_3$): $\delta$=1.19 (d, 3H), 1.25 (d, 3H), 1.78 (s, 3H), 2.39 (hep., 1H), 2.78 (s, 3H), 6.54 (t, 1H), 6.96-7.02 (m, 2H), 7.40 (bs, 1H).

Example 2

This example illustrates the preparation of 5-bromo-N-(1-cyclohexylethyl)-2-(3,5-difluoroanilino)thiazole-4-carboxamide (Compound I.e.2)

a) Preparation of ethyl 2-(3,5-difluoroanilino)thiazole-4-carboxylate

Potassium phosphate (1.9 g, 8.7 mmol), tris(dibenzylideneacetone)dipalladium (0.27 g, 0.29 mmol), Xantphos (0.17 g, 0.29 mmol) and 3,5-difluoroiodobenzene (1.5 g, 6.4 mmol) were added successively to a mixture of ethyl 2-aminothiazole-4-carboxylate (1.0 g, 5.8 mmol) in a mixture of 9 ml of toluene and 3 ml of water. The mixture was flushed with argon for 20 mins, then heated in the microwave to 140° C. for 1 h. The reaction mixture was diluted with water and extracted with ethyl acetate. The organic layer was washed with saturated aqueous sodium bicarbonate solution and water, dried over magnesium sulfate and evaporated under reduced pressure. The residue was purified by chromatography on silica gel, using ethyl acetate and cyclohexane as eluents, to deliver ethyl 2-(3,5-difluoroanilino)thiazole-4-carboxylate (0.16 g, 0.56 mmol). $^1$H-NMR (400 MHz, CDCl$_3$): δ=1.41 (t, 3H), 4.40 (q, 2H), 6.54 (t, 1H), 6.95 (d, 2H), 7.63 (s, 1H).

b) Preparation of 2-(3,5-difluoroanilino)thiazole-4-carboxylic Acid

Lithium hydroxide monohydrate (54 mg, 2.2 mmol) was added to a solution of ethyl 2-(3,5-difluoroanilino)thiazole-4-carboxylate (0.16 g, 0.56 mmol) in a mixture of 2 ml of tetrahydrofuran and 1 ml of water. The reaction mixture was stirred 16 h at room temperature, then the solvents were removed in vacuo. The residue was diluted with water, then 2 N hydrochloric acid was slowly added until a pH of 3-4 was reached. The mixture was extracted with ethyl acetate, the organic layer was washed with water and brine, dried over magnesium sulfate and evaporated under reduced pressure to deliver 2-(3,5-difluoroanilino)thiazole-4-carboxylic acid (98 mg, 0.38 mmol). $^1$H-NMR (400 MHz, MeOD): δ=6.52 (t, 1H), 7.33 (d, 2H), 7.72 (s, 1H).

c) Preparation of N-(1-cyclohexylethyl)-2-(3,5-difluoroanilino)thiazole-4-carboxamide Triethylamine (49 mg, 0.48 mmol) and propane phosphonic acid anhydride (T3P, 0.2 g, 0.32 mmol) were consecutively added to a solution of 2-(3,5-difluoroanilino)thiazole-4-carboxylic acid (47 mg, 0.16 mmol) in 5 ml of acetonitrile. The reaction mixture was stirred for 30 min at room temperature, then 1-cyclohexylethylamine (24 mg, 0.19 mmol) was added. Stirring at room temperature was continued for 16 h, then the reaction mixture was diluted with ethyl acetate, washed with water, dried over magnesium sulfate and evaporated under reduced pressure. The residue was purified by chromatography on silica gel, using ethyl acetate and cyclohexane as eluents, to deliver N-(1-cyclohexylethyl)-2-(3,5-difluoroanilino)thiazole-4-carboxamide (29 mg, 0.08 mmol). $^1$H-NMR (400 MHz, CDCl$_3$): δ=1.02-1.13 (m, 4H), 1.20 (d, 3H), 1.48 (q, 1H), 1.65-1.82 (m, 6H), 4.03 (q, 1H), 6.55 (t, 1H), 7.03 (d, 2H), 7.55 (s, 1H).

d) Preparation of 5-bromo-N-(1-cyclohexylethyl)-2-(3,5-difluoroanilino)thiazole-4-carboxamide (Compound 1.e.2)

N-bromosuccinimide (12 mg, 0.07 mmol) was added to a solution of N-(1-cyclohexylethyl)-2-(3,5-difluoroanilino)thiazole-4-carboxamide (23 mg, 0.06 mmol) in 2 ml of N,N-dimethylformamide. The reaction mixture was stirred for 1 h at room temperature, then diluted with ethyl acetate and washed with water. The organic layer was dried over magnesium sulfate and evaporated under reduced pressure. The residue was purified by chromatography on silica gel, using ethyl acetate and cyclohexane as eluents, to deliver 5-bromo-N-(1-cyclohexylethyl)-2-(3,5-difluoroanilino)thiazole-4-carboxamide (Compound I.e.2, 18 mg, 0.04 mmol). $^1$H-NMR (400 MHz, CDCl$_3$): δ=1.01-1.18 (m, 4H), 1.21 (d, 3H), 1.48 (q, 1H), 1.67-1.83 (m, 6H), 3.99 (q, 1H), 6.54 (t, 1H), 7.06 (d, 2H).

Table 1 below illustrates examples of individual compounds of formula (I) according to the invention.

TABLE 1

Individual compounds of formula (I) according to the invention

| Compound No. | X | $R^1$ | $R^2$ | $R^3$ |
|---|---|---|---|---|
| 1 | CH | F | H | Cl |
| 2 | CH | F | H | Br |
| 3 | CH | F | H | CH$_3$ |
| 4 | CH | F | CH$_3$ | CH$_3$ |
| 5 | CH | F | OCH$_3$ | CH$_3$ |
| 6 | CH | Cl | H | Cl |
| 7 | CH | Cl | H | Br |
| 8 | CH | Cl | H | CH$_3$ |
| 9 | CH | Cl | CH$_3$ | CH$_3$ |
| 10 | CH | Cl | OCH$_3$ | CH$_3$ |
| 11 | CH | Br | H | Cl |
| 12 | CH | Br | H | Br |
| 13 | CH | Br | H | CH$_3$ |
| 14 | CH | Br | CH$_3$ | CH$_3$ |
| 15 | CH | Br | OCH$_3$ | CH$_3$ |
| 16 | CH | CN | H | Cl |
| 17 | CH | CN | H | Br |
| 18 | CH | CN | H | CH$_3$ |
| 19 | CH | CN | CH$_3$ | CH$_3$ |
| 20 | CH | CN | OCH$_3$ | CH$_3$ |
| 21 | CH | CH$_3$ | H | Cl |
| 22 | CH | CH$_3$ | H | Br |
| 23 | CH | CH$_3$ | H | CH$_3$ |
| 24 | CH | CH$_3$ | CH$_3$ | CH$_3$ |
| 25 | CH | CH$_3$ | OCH$_3$ | CH$_3$ |
| 26 | CH | CF$_3$ | H | Cl |
| 27 | CH | CF$_3$ | H | Br |
| 28 | CH | CF$_3$ | H | CH$_3$ |
| 29 | CH | CF$_3$ | CH$_3$ | CH$_3$ |
| 30 | CH | CF$_3$ | OCH$_3$ | CH$_3$ |
| 31 | CH | OCH$_3$ | H | Cl |
| 32 | CH | OCH$_3$ | H | Br |
| 33 | CH | OCH$_3$ | H | CH$_3$ |
| 34 | CH | OCH$_3$ | CH$_3$ | CH$_3$ |
| 35 | CH | OCH$_3$ | OCH$_3$ | CH$_3$ |
| 36 | CH | OCF$_3$ | H | Cl |
| 37 | CH | OCF$_3$ | H | Br |
| 38 | CH | OCF$_3$ | H | CH$_3$ |
| 39 | CH | OCF$_3$ | CH$_3$ | CH$_3$ |
| 40 | CH | OCF$_3$ | OCH$_3$ | CH$_3$ |
| 41 | N | F | H | Cl |
| 42 | N | F | H | Br |
| 43 | N | F | H | CH$_3$ |
| 44 | N | F | CH$_3$ | CH$_3$ |
| 45 | N | F | OCH$_3$ | CH$_3$ |
| 46 | N | Cl | H | Cl |
| 47 | N | Cl | H | Br |
| 48 | N | Cl | H | CH$_3$ |
| 49 | N | Cl | CH$_3$ | CH$_3$ |
| 50 | N | Cl | OCH$_3$ | CH$_3$ |
| 51 | N | Br | H | Cl |
| 52 | N | Br | H | Br |
| 53 | N | Br | H | CH$_3$ |
| 54 | N | Br | CH$_3$ | CH$_3$ |
| 55 | N | Br | OCH$_3$ | CH$_3$ |
| 56 | N | CN | H | Cl |
| 57 | N | CN | H | Br |
| 58 | N | CN | H | CH$_3$ |
| 59 | N | CN | CH$_3$ | CH$_3$ |
| 60 | N | CN | OCH$_3$ | CH$_3$ |
| 61 | N | CH$_3$ | H | Cl |

TABLE 1-continued

Individual compounds of formula (I) according to the invention

| Compound No. | X | R¹ | R² | R³ |
|---|---|---|---|---|
| 62 | N | CH₃ | H | Br |
| 63 | N | CH₃ | H | CH₃ |
| 64 | N | CH₃ | CH₃ | CH₃ |
| 65 | N | CH₃ | OCH₃ | CH₃ |
| 66 | N | CF₃ | H | Cl |
| 67 | N | CF₃ | H | Br |
| 68 | N | CF₃ | H | CH₃ |
| 69 | N | CF₃ | CH₃ | CH₃ |
| 70 | N | CF₃ | OCH₃ | CH₃ |
| 71 | N | OCH₃ | H | Cl |
| 72 | N | OCH₃ | H | Br |
| 73 | N | OCH₃ | H | CH₃ |
| 74 | N | OCH₃ | CH₃ | CH₃ |
| 75 | N | OCH₃ | OCH₃ | CH₃ |
| 76 | N | OCF₃ | H | Cl |
| 77 | N | OCF₃ | H | Br |
| 78 | N | OCF₃ | H | CH₃ |
| 79 | N | OCF₃ | CH₃ | CH₃ |
| 80 | N | OCF₃ | OCH₃ | CH₃ | where
a) 80 compounds of formula (I.a):

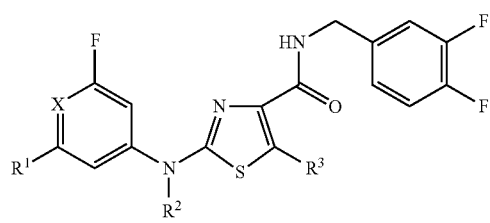

(I.a)

wherein $R^1$, $R^2$, $R^3$ and X are as defined in Table 1.
b) 80 compounds of formula (I.b):

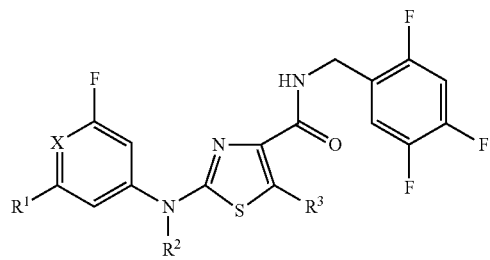

(I.b)

wherein $R^1$, $R^2$, $R^3$ and X are as defined in Table 1.

c) 80 compounds of formula (I.c):

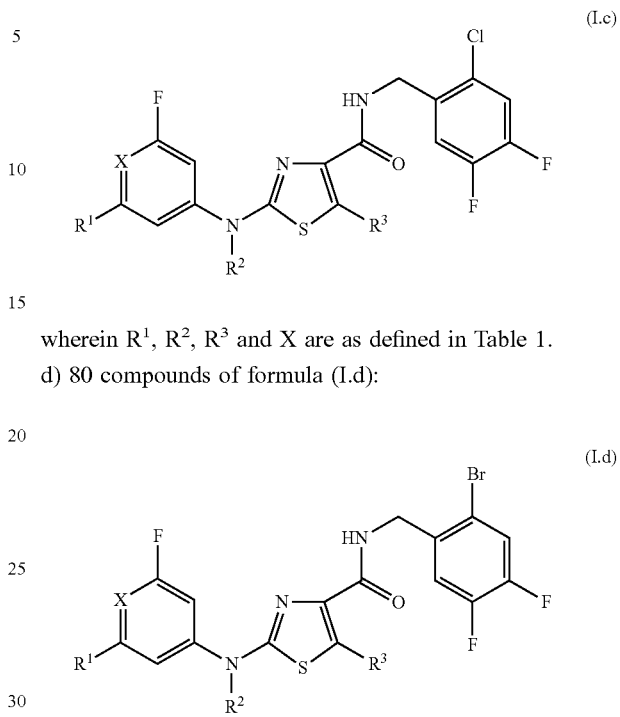

wherein $R^1$, $R^2$, $R^3$ and X are as defined in Table 1.
d) 80 compounds of formula (I.d):

(I.d)

wherein $R^1$, $R^2$, $R^3$ and X are as defined in Table 1.
e) 80 compounds of formula (I.e):

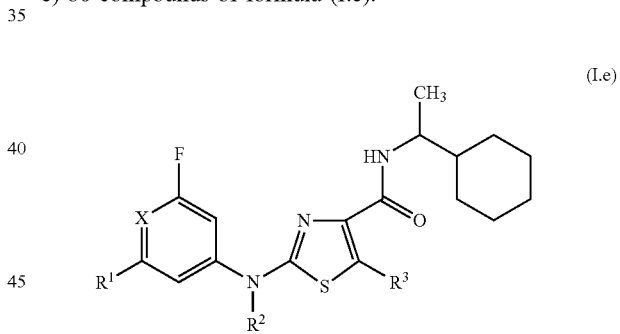

(I.e)

wherein $R^1$, $R^2$, $R^3$ and X are as defined in Table 1.
f) 80 compounds of formula (I.f):

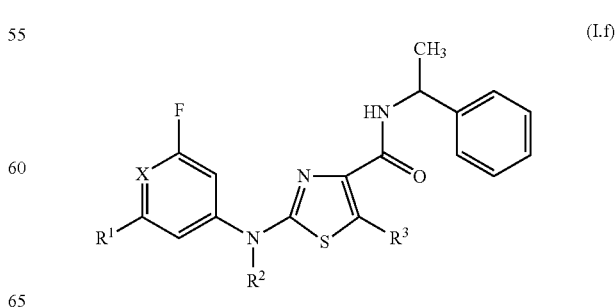

(I.f)

wherein $R^1$, $R^2$, $R^3$ and X are as defined in Table 1.

g) 80 compounds of formula (I.g):

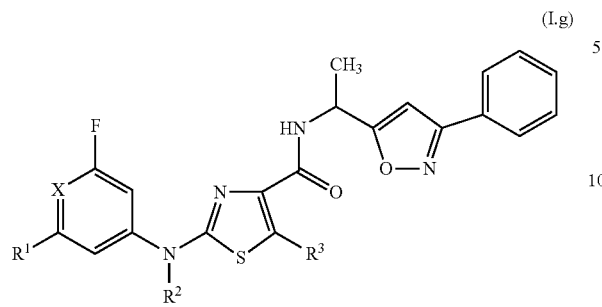

wherein $R^1$, $R^2$, $R^3$ and X are as defined in Table 1.

h) 80 compounds of formula (I.h):

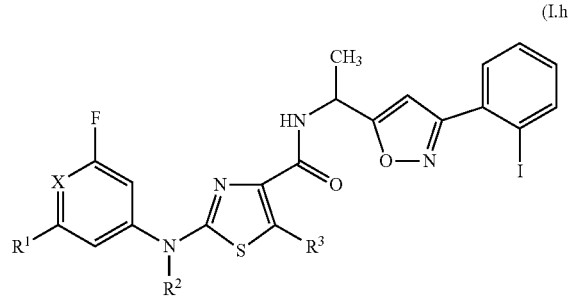

wherein $R^1$, $R^2$, $R^3$ and X are as defined in Table 1.

i) 80 compounds of formula (I.i):

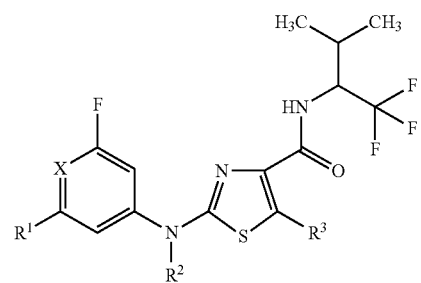

wherein $R^1$, $R^2$, $R^3$ and X are as defined in Table 1.

j) 80 compounds of formula (I.j):

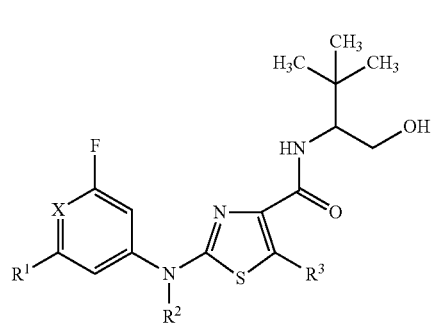

wherein $R^1$, $R^2$, $R^3$ and X are as defined in Table 1.

k) 80 compounds of formula (I.k):

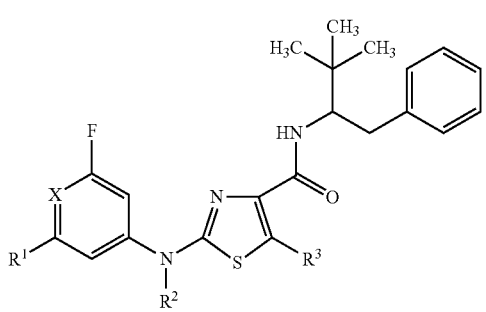

wherein $R^1$, $R^2$, $R^3$ and X are as defined in Table 1.

m) 80 compounds of formula (I.m):

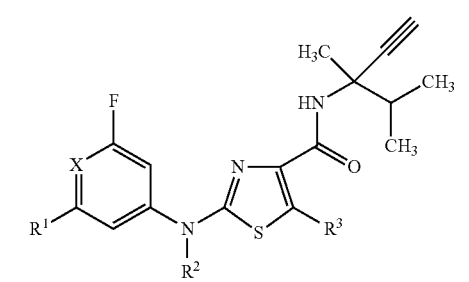

wherein $R^1$, $R^2$, $R^3$ and X are as defined in Table 1.

n) 80 compounds of formula (I.n):

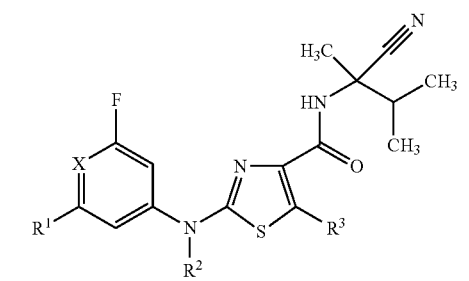

wherein $R^1$, $R^2$, $R^3$ and X are as defined in Table 1.

o) 80 compounds of formula (I.o):

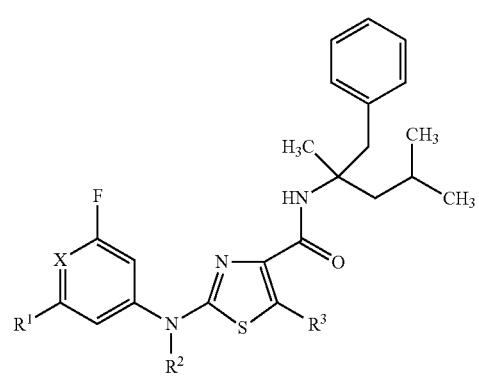

wherein $R^1$, $R^2$, $R^3$ and X are as defined in Table 1.

p) 80 compounds of formula (I.p):

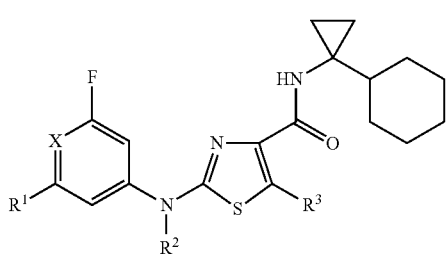

Wherein R¹, R², R³ and X are as defined in Table 1.

q) 80 compounds of formula (I.q):

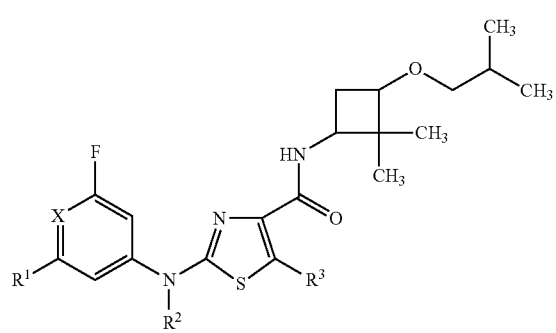

wherein R¹, R², R³ and X are as defined in Table 1.

r) 80 compounds of formula (I.r):

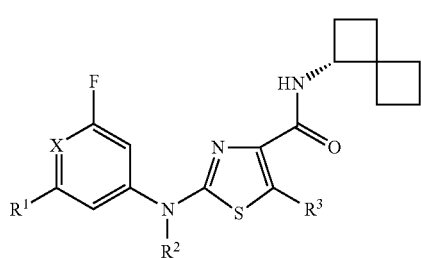

wherein R¹, R², R³ and X are as defined in Table 1.

s) 80 compounds of formula (I.s):

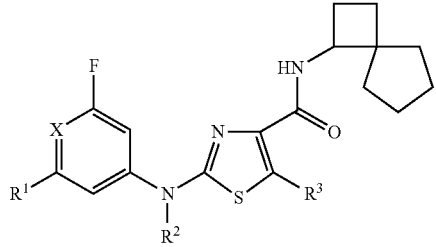

wherein R¹, R², R³ and X are as defined in Table 1.

t) 80 compounds of formula (I.t):

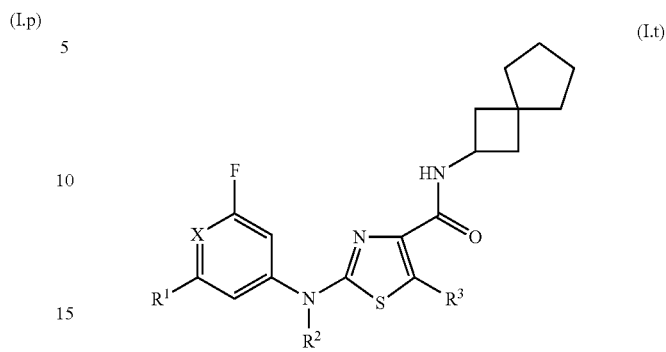

wherein R¹, R², R³ and X are as defined in Table 1.

u) 80 compounds of formula (I.u):

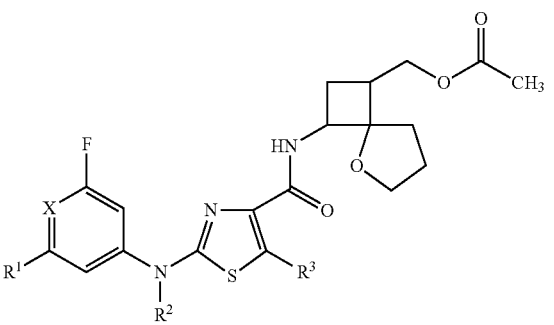

wherein R¹, R², R³ and X are as defined in Table 1.

v) 80 compounds of formula (I.v):

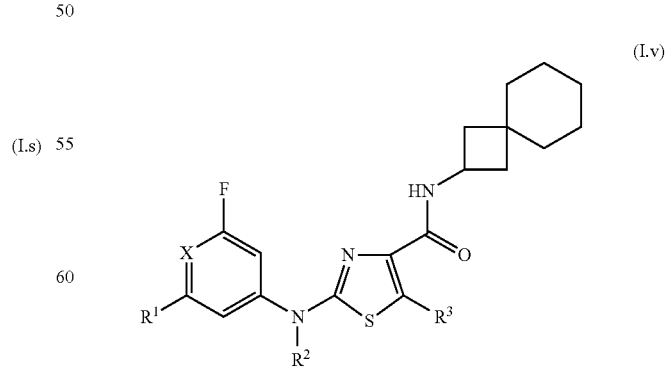

wherein R¹, R², R³ and X are as defined in Table 1.

w) 80 compounds of formula (I.w):

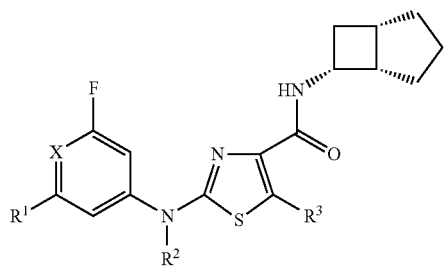

wherein $R^1$, $R^2$, $R^3$ and X are as defined in Table 1.

x) 80 compounds of formula (I.x):

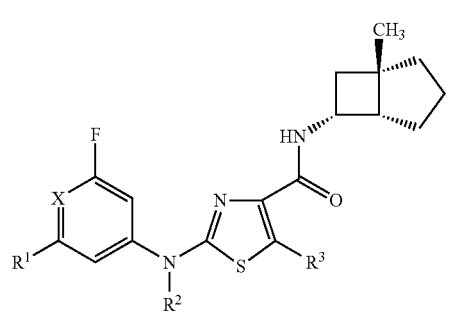

wherein $R^1$, $R^2$, $R^3$ and X are as defined in Table 1.

y) 80 compounds of formula (I.y):

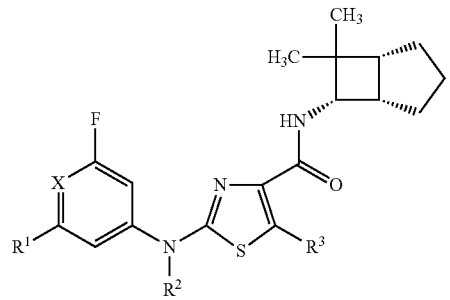

wherein $R^1$, $R^2$, $R^3$ and X are as defined in Table 1.

z) 80 compounds of formula (I.z):

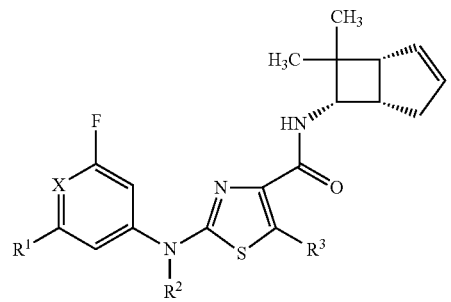

wherein $R^1$, $R^2$, $R^3$ and X are as defined in Table 1.

aa) 80 compounds of formula (I.aa):

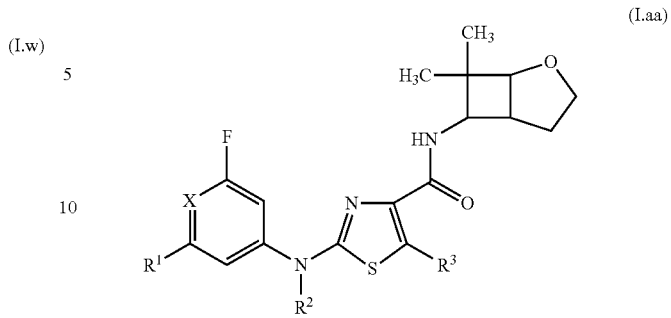

wherein $R^1$, $R^2$, $R^3$ and X are as defined in Table 1.

ab) 80 compounds of formula (I.ab):

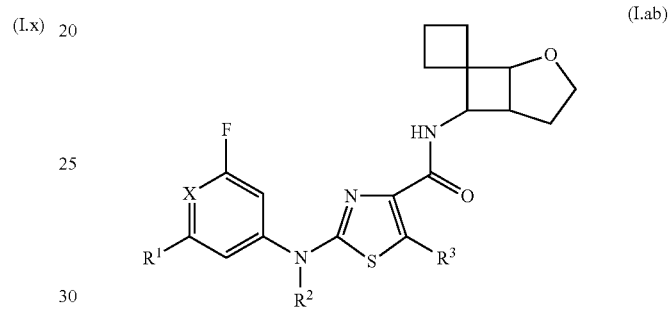

wherein $R^1$, $R^2$, $R^3$ and X are as defined in Table 1.

ac) 80 compounds of formula (I.ac):

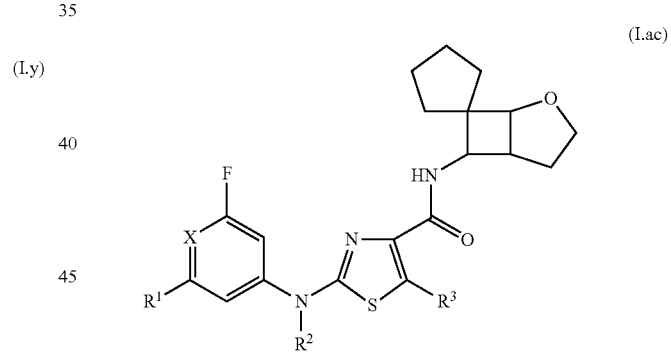

wherein $R^1$, $R^2$, $R^3$ and X are as defined in Table 1.

ad) 80 compounds of formula (I.ad):

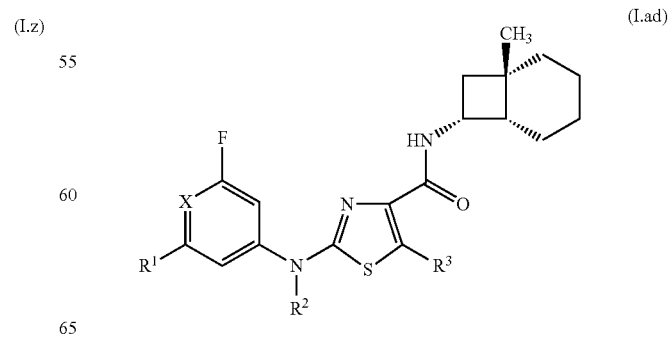

wherein $R^1$, $R^2$, $R^3$ and X are as defined in Table 1.

ae) 80 compounds of formula (I.ae):

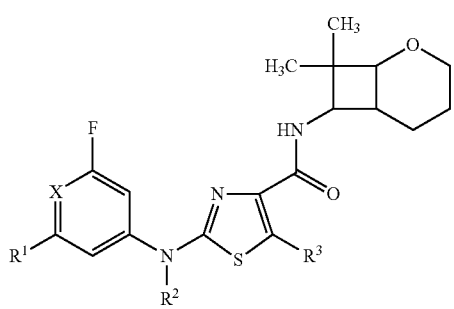

wherein $R^1$, $R^2$, $R^3$ and X are as defined in Table 1.

af) 80 compounds of formula (I.af):

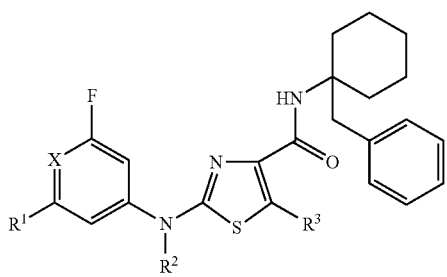

wherein $R^1$, $R^2$, $R^3$ and X are as defined in Table 1.

ag) 80 compounds of formula (I.ag):

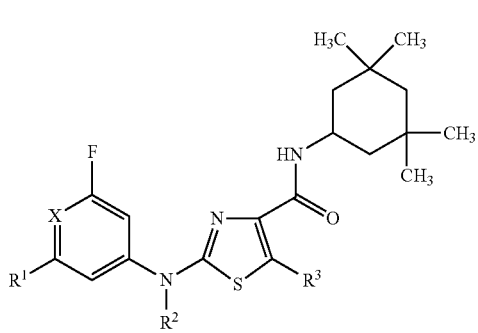

wherein $R^1$, $R^2$, $R^3$ and X are as defined in Table 1.

ah) 80 compounds of formula (I.ah):

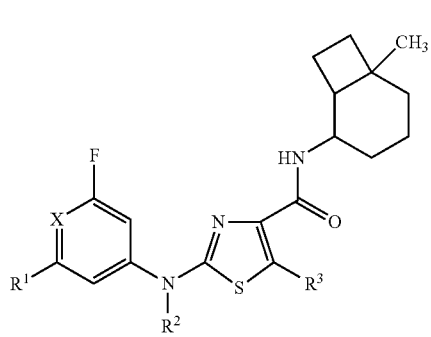

wherein $R^1$, $R^2$, $R^3$ and X are as defined in Table 1.

ai) 80 compounds of formula (I.ai):

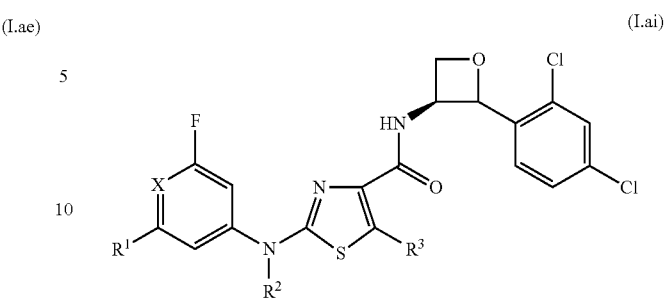

wherein $R^1$, $R^2$, $R^3$ and X are as defined in Table 1.

aj) 80 compounds of formula (I.aj):

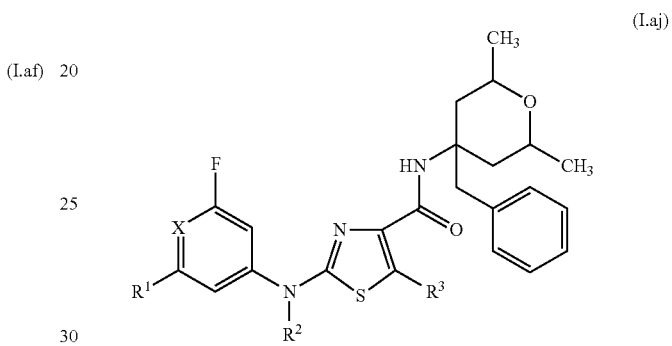

wherein $R^1$, $R^2$, $R^3$ and X are as defined in Table 1.

ak) 80 compounds of formula (I.ak):

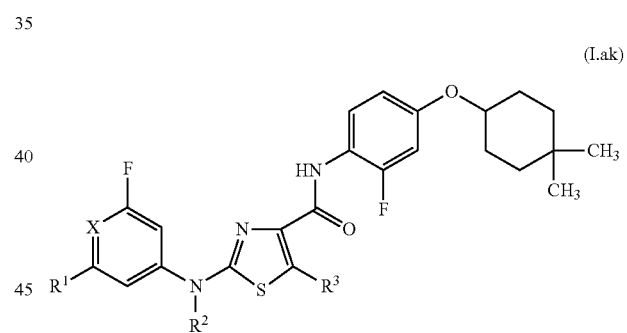

wherein $R^1$, $R^2$, $R^3$ and X are as defined in Table 1.

am) 80 compounds of formula (I.am):

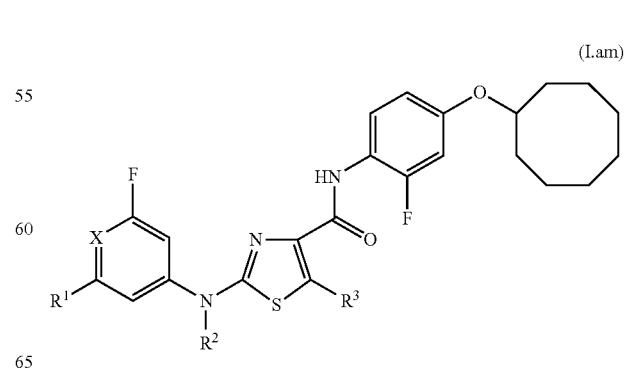

wherein $R^1$, $R^2$, $R^3$ and X are as defined in Table 1.

an) 80 compounds of formula (I.an):

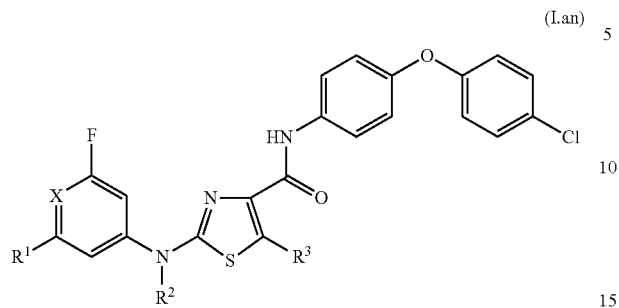

wherein $R^1$, $R^2$, $R^3$ and X are as defined in Table 1.

ao) 80 compounds of formula (I.ao):

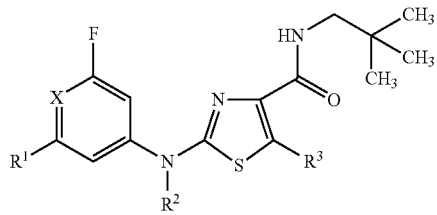

wherein $R^1$, $R^2$, $R^3$ and X are as defined in Table 1.

ap) 80 compounds of formula (I.ap):

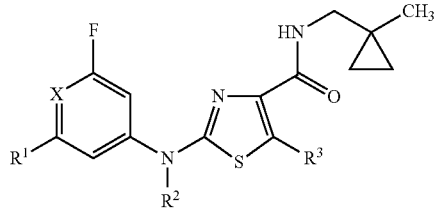

wherein $R^1$, $R^2$, $R^3$ and X are as defined in Table 1.

aq) 80 compounds of formula (I.aq):

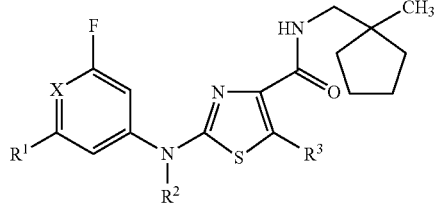

wherein $R^1$, $R^2$, $R^3$ and X are as defined in Table 1.

ar) 80 compounds of formula (I.ar):

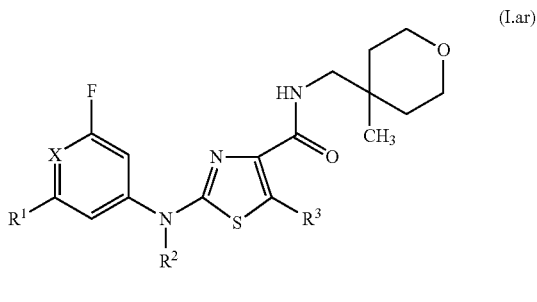

wherein $R^1$, $R^2$, $R^3$ and X are as defined in Table 1.

as) 80 compounds of formula (I.as):

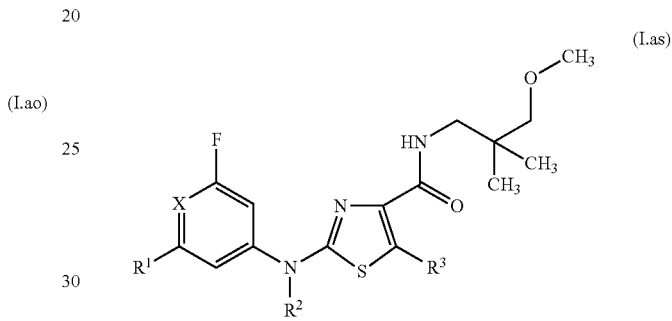

wherein $R^1$, $R^2$, $R^3$ and X are as defined in Table 1.

at) 80 compounds of formula (I.at):

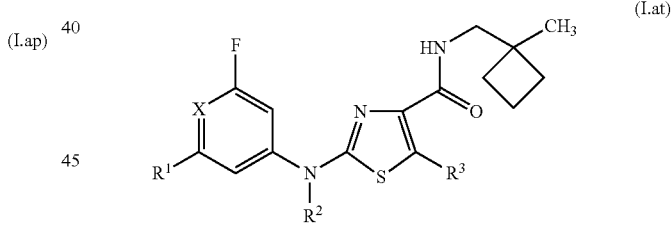

wherein $R^1$, $R^2$, $R^3$ and X are as defined in Table 1.

au) 80 compounds of formula (I.au):

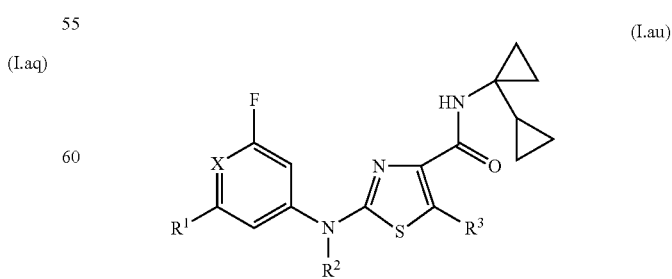

wherein $R^1$, $R^2$, $R^3$ and X are as defined in Table 1.

av) 80 compounds of formula (I.av):

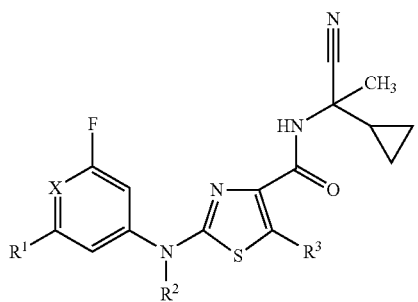
(I.av)

wherein R¹, R², R³ and X are as defined in Table 1.

aw) 80 compounds of formula (I.aw):

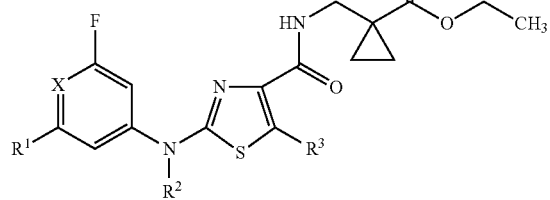
(I.aw)

wherein R¹, R², R³ and X are as defined in Table 1.

ax) 80 compounds of formula (I.ax):

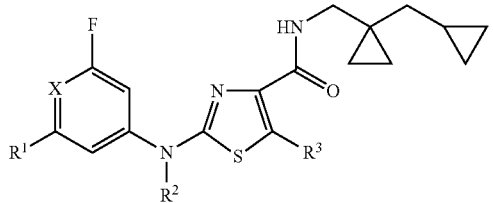
(I.ax)

wherein R¹, R², R³ and X are as defined in Table 1.

ay) 80 compounds of formula (I.ay):

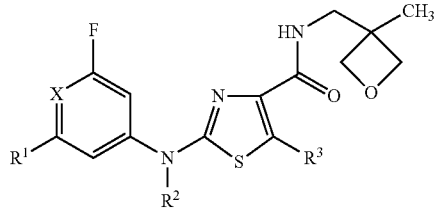
(I.ay)

wherein R¹, R², R³ and X are as defined in Table 1.

az) 80 compounds of formula (I.az):

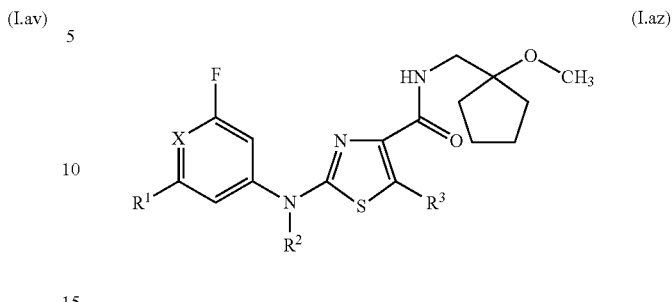
(I.az)

wherein R¹, R², R³ and X are as defined in Table 1.

ba) 80 compounds of formula (I.ba):

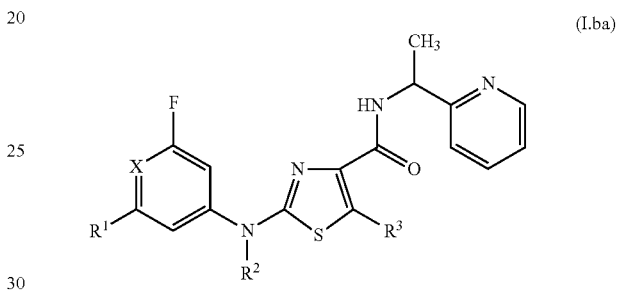
(I.ba)

wherein R¹, R², R³ and X are as defined in Table 1.

bb) 80 compounds of formula (I.bb):

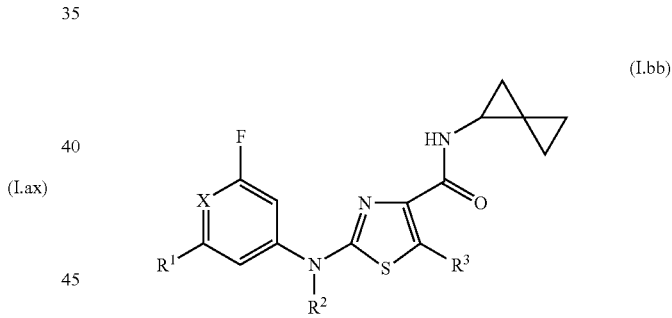
(I.bb)

wherein R¹, R², R³ and X are as defined in Table 1.

bc) 80 compounds of formula (I.bc):

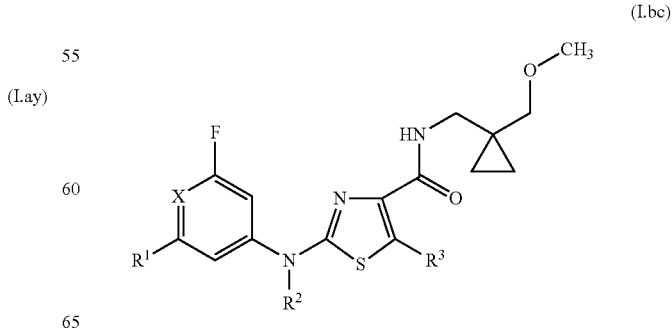
(I.bc)

wherein R¹, R², R³ and X are as defined in Table 1.

bd) 80 compounds of formula (I.bd):

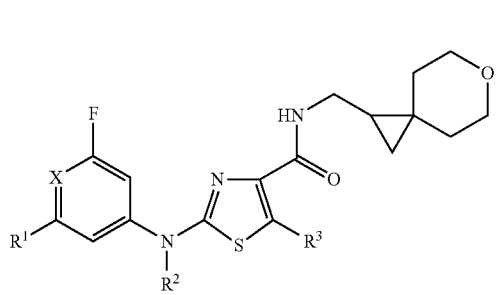

(I.bd)

wherein $R^1$, $R^2$, $R^3$ and X are as defined in Table 1.
be) 80 compounds of formula (I.be):

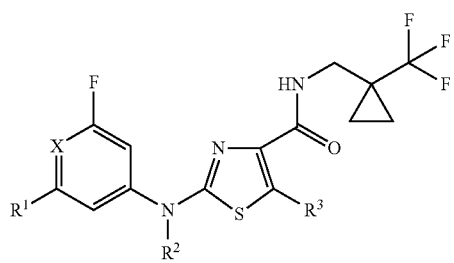

(I.be)

wherein $R^1$, $R^2$, $R^3$ and X are as defined in Table 1.
bf) 80 compounds of formula (I.bf):

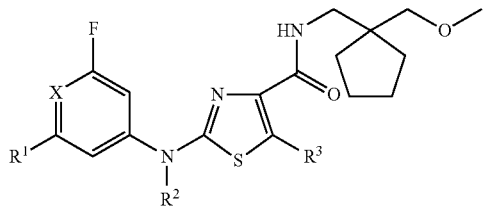

(I.bf)

wherein $R^1$, $R^2$, $R^3$ and X are as defined in Table 1.
bg) 80 compounds of formula (I.bg):

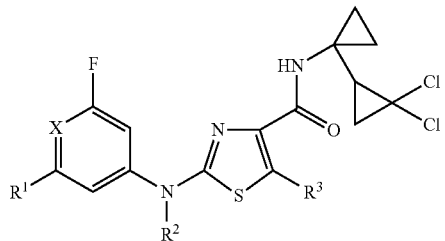

(I.bg)

wherein $R^1$, $R^2$, $R^3$ and X are as defined in Table 1.

bh) 80 compounds of formula (I.bh):

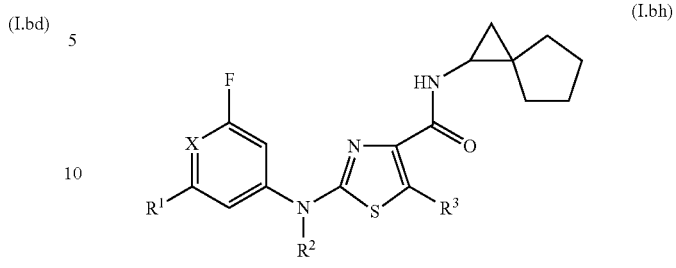

(I.bh)

wherein $R^1$, $R^2$, $R^3$ and X are as defined in Table 1.
bi) 80 compounds of formula (I.bi):

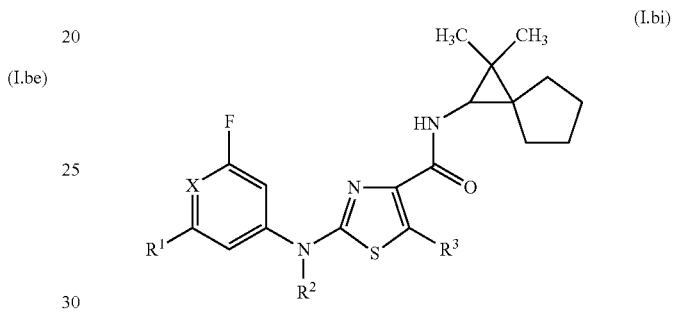

(I.bi)

wherein $R^1$, $R^2$, $R^3$ and X are as defined in Table 1.
bj) 80 compounds of formula (I.bj):

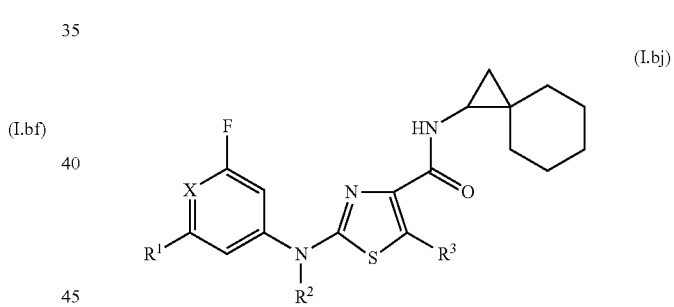

(I.bj)

wherein $R^1$, $R^2$, $R^3$ and X are as defined in Table 1.
bk) 80 compounds of formula (I.bk):

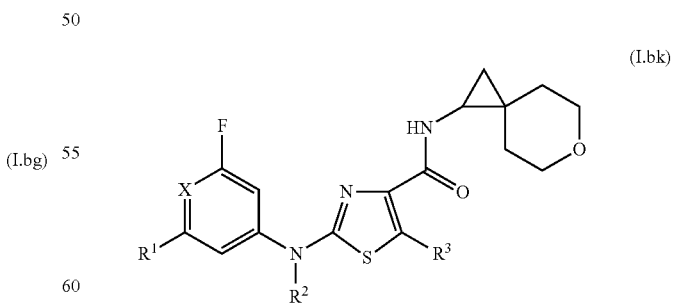

(I.bk)

wherein $R^1$, $R^2$, $R^3$ and X are as defined in Table 1.

Throughout this description, temperatures are given in degrees Celsius (° C.) and "m.p." means melting point. LC/MS means Liquid Chromatography Mass Spectrometry and the description of the apparatus and the method is:

(ACQUITY UPLC from Waters, Phenomenex Gemini C18, 3 μm particle size, 110 Angstrom, 30×3 mm column, 1.7 mL/min., 60° C., H₂O+0.05% HCOOH (95%)/CH₃CN/MeOH 4:1+0.04% HCOOH (5%)—2 min.—CH₃CN/MeOH 4:1+0.04% HCOOH (5%)—0.8 min., ACQUITY SQD Mass Spectrometer from Waters, ionization method: electrospray (ESI), Polarity: positive ions, Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700)).

TABLE 2

Melting point and LC/MS data for selected compounds of Table 1.

| Compound no. | Melting point (° C.) | LC/MS Rt = Retention time |
|---|---|---|
| I.a.3 | | Rt = 1.11 min; MS: m/z = 396 (M + 1) |
| I.b.3 | | Rt = 1.13 min; MS: m/z = 414 (M + 1) |
| I.c.3 | | Rt = 1.18 min; MS: m/z = 430 (M + 1) |
| I.d.3 | | Rt = 1.19 min; MS: m/z = 476 (M + 1) |
| I.e.2 | | Rt = 1.30 min; MS: m/z = 446 (M + 1) |
| I.e.3 | | Rt = 1.26 min; MS: m/z = 380 (M + 1) |
| I.f.3 | | Rt = 1.19 min; MS: m/z = 374 (M + 1) |
| I.g.3 | | Rt = 1.14 min; MS: m/z = 441 (M + 1) |
| I.h.3 | | Rt = 1.18 min; MS: m/z = 567 (M + 1) |
| I.i.3 | | Rt = 2.05 min; MS: m/z = 394 (M + 1) |
| I.j.3 | | Rt = 1.65 min; MS: m/z = 370 (M + 1) |
| I.k.3 | | Rt = 1.25 min; MS: m/z = 430 (M + 1) |
| I.m.3 | | Rt = 1.99 min; MS: m/z = 364 (M + 1) |
| I.n.3 | | Rt = 1.83 min; MS: m/z = 365 (M + 1) |
| I.o.3 | | Rt = 1.33 min; MS: m/z = 444 (M + 1) |
| I.p.3 | | Rt = 2.19 min; MS: m/z = 392 (M + 1) |
| I.q.3 | | Rt = 2.24 min; MS: m/z = 424 (M + 1) |
| I.r.2 | | Rt = 1.22 min; MS: m/z = 430 (M + 1) |
| I.r.3 | | Rt = 1.22 min; MS: m/z = 364 (M + 1) |
| I.s.3 | | Rt = 1.24 min; MS: m/z = 378 (M + 1) |
| I.t.3 | | Rt = 1.25 min; MS: m/z = 378 (M + 1) |
| I.u.3 | | Rt = 1.09 min; MS: m/z = 452 (M + 1) |
| I.v.3 | | Rt = 1.30 min; MS: m/z = 392 (M + 1) |
| I.w.2 | | Rt = 1.20 min; MS: m/z = 430 (M + 1) |
| I.w.3 | | Rt = 1.22 min; MS: m/z = 364 (M + 1) |
| I.x.3 | | Rt = 1.27 min; MS: m/z = 378 (M + 1) |
| I.y.1 | | Rt = 1.30 min; MS: m/z = 412 (M + 1) |
| I.y.2 | | Rt = 1.31 min; MS: m/z = 458 (M + 1) |
| I.y.3 | | Rt = 1.29 min; MS: m/z = 392 (M + 1) |
| I.aa.3 | | Rt = 1.77 min; MS: m/z = 394 (M + 1) |
| I.ab.3 | | Rt = 1.83 min; MS: m/z = 406 (M + 1) |
| I.ac.3 | | Rt = 1.93 min; MS: m/z = 420 (M + 1) |
| I.ad.3 | | Rt = 1.30 min; MS: m/z = 392 (M + 1) |
| I.ae.3 | | Rt = 1.95 min; MS: m/z = 408 (M + 1) |
| I.af.3 | | Rt = 1.32 min; MS: m/z = 442 (M + 1) |
| I.ag.3 | | Rt = 1.37 min; MS: m/z = 408 (M + 1) |
| I.ah.2 | | Rt = 1.33 min; MS: m/z = 458 (M + 1) |
| I.ah.3 | | Rt = 2.21 min; MS: m/z = 392 (M + 1) |
| I.ai.3 | | Rt = 1.16 min; MS: m/z = 470 (M + 1) |
| I.aj.3 | | Rt = 1.23 min; MS: m/z = 472 (M + 1) |
| I.ak.3 | | Rt = 1.42 min; MS: m/z = 490 (M + 1) |
| I.am.3 | | Rt = 1.43 min; MS: m/z = 490 (M + 1) |
| I.an.3 | | Rt = 1.32 min; MS: m/z = 472 (M + 1) |
| I.e.43 | 163-165 | |
| I.f.8 | | Rt = 2.06 min; MS: m/z = 390 (M + 1) |
| I.f.18 | | Rt = 1.83 min; MS: m/z = 379 (M + 1) |
| I.f.23 | 53-56 | |
| I.f.33 | | Rt = 1.89 min; MS: m/z = 385 (M + 1) |
| I.f.41 | | Rt = 1.69 min; MS: m/z = 395 (M + 1) |
| I.f.43 | 199-200 | |
| I.s.8 | | Rt = 2.31 min; MS: m/z = 394 (M + 1) |
| I.s.18 | | Rt = 2.05 min; MS: m/z = 385 (M + 1) |
| I.s.23 | | Rt = 2.21 min; MS: m/z = 374 (M + 1) |
| I.s.33 | | Rt = 2.12 min; MS: m/z = 390 (M + 1) |
| I.s.41 | | Rt = 1.92 min; MS: m/z = 399 (M + 1) |
| I.s.43 | 156-162 | |
| I.z.43 | | Rt = 1.99 min; MS: m/z = 391 (M + 1) |
| I.aa.43 | | Rt = 1.75 min; MS: m/z = 409 (M + 1) |
| I.ao.3 | 104-107 | |
| I.ao.43 | 170-173 | |
| I.ap.3 | 189-192 | |
| I.ap.43 | 182-187 | |
| I.aq.3 | 163-168 | |
| I.aq.43 | | Rt = 1.14 min; MS: m/z = 367 (M + 1) |
| I.ar.3 | 147-150 | |
| I.ar.43 | | Rt = 0.96 min; MS: m/z = 383 (M + 1) |
| I.as.3 | 130-135 | |
| I.as.43 | 147-159 | |
| I.at.3 | 183-187 | |
| I.at.43 | 138-149 | |
| I.au.3 | 47-60 | |
| I.au.43 | 165-190 | |
| I.av.43 | 80-91 | |
| I.aw.3 | 158-160 | |
| I.ax.3 | 100-135 | |
| I.ax.43 | | Rt = 1.14 min; MS: m/z = 379 (M + 1) |
| I.ay.3 | 155-158 | |
| I.az.3 | 140-143 | |
| I.ba.43 | | Rt = 1.36 min; MS: m/z = 374 (M + 1) |
| I.bb.3 | 145-175 | |
| I.bb.43 | 129-158 | |
| I.bc.3 | 159-162 | |
| I.bc.43 | 162-169 | |
| I.bd.43 | 65-81 | |
| I.be.3 | | Rt = 1.12 min; MS: m/z = 392 (M + 1) |
| I.bf.3 | 155-158 | |

Formulation Examples

| Wettable powders | a) | b) | c) |
|---|---|---|---|
| active ingredient [compound of formula (I)] | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient [compound of formula (I)] | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The active ingredient is thoroughly mixed with the adjuvants and the mixture is thoroughly ground in a suitable mill, affording powders that can be used directly for seed treatment.

Emulsifiable Concentrate

| active ingredient [compound of formula (I)] | 10% |
|---|---|
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |

| | |
|---|---|
| Cyclohexanone | 30% |
| xylene mixture | 50% |

Emulsions of any required dilution, which can be used in plant protection, can be obtained from this concentrate by dilution with water.

| Dusts | a) | b) | c) |
|---|---|---|---|
| Active ingredient [compound of formula (I)] | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

Extruder Granules

| | |
|---|---|
| Active ingredient [compound of formula (I)] | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

Coated Granules

| | |
|---|---|
| Active ingredient [compound of formula (I)] | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

Suspension Concentrate

| | |
|---|---|
| active ingredient [compound of formula (I)] | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Flowable Concentrate for Seed Treatment

| | |
|---|---|
| active ingredient [compound of formula (I)] | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

Slow Release Capsule Suspension 28 parts of a combination of the compound of formula (I) are mixed with 2 parts of an aromatic solvent and 7 parts of toluene diisocyanate/polymethylene-polyphenylisocyanate-mixture (8:1). This mixture is emulsified in a mixture of 1.2 parts of polyvinyl alcohol, 0.05 parts of a defoamer and 51.6 parts of water until the desired particle size is achieved. To this emulsion a mixture of 2.8 parts 1,6-diaminohexane in 5.3 parts of water is added. The mixture is agitated until the polymerization reaction is completed.

The obtained capsule suspension is stabilized by adding 0.25 parts of a thickener and 3 parts of a dispersing agent. The capsule suspension formulation contains 28% of the active ingredients. The medium capsule diameter is 8-15 microns.

The resulting formulation is applied to seeds as an aqueous suspension in an apparatus suitable for that purpose.

Biological Examples

*Alternaria solani*/Tomato/Leaf Disc (Early Blight)

Tomato leaf disks cv. Baby are placed on agar in multiwell plates (24-well format) and sprayed with the test compound formulated with DMSO and Tween20 and diluted in water. The leaf disks are inoculated with a spore suspension of the fungus 2 days after application. The inoculated leaf disks are incubated at 23° C./21° C. (day/night) and 80% relative humidity (rh) under a light regime of 12/12 h (light/dark) in a climate cabinet and the activity of a compound is assessed as percent disease control compared to untreated when an appropriate level of disease damage appears on untreated check disk leaf disks (5-7 days after application).

Compounds I.a.3, I.e.3, I.r.3, I.s.3, I.y.1, I.y.3, I.ac.3, I.s.43, I.ao.3, I.au.3, I.at.3, I.bb.3, I.bb.43 at 200 ppm in the formulation gives at least 80% disease control in this test when compared to untreated checks under the same conditions, which show extensive mycelial growth.

*Blumeria graminis* f. Sp. *Tritici* (*Erysiphe graminis* f. Sp. *Tritici*)/Wheat/Leaf Disc Preventative (Powdery Mildew on Wheat)

Wheat leaf segments cv. Kanzler are placed on agar in a multiwell plate (24-well format) and sprayed with the test compound formulated with DMSO and Tween20 and diluted in water. The leaf disks are inoculated by shaking powdery mildew infected plants above the test plates 1 day after application. The inoculated leaf disks are incubated at 20° C. and 60% rh under a light regime of 24 h darkness followed by 12 h light/12 h darkness in a climate chamber and the activity of a compound is assessed as percent disease control compared to untreated when an appropriate level of disease damage appears on untreated check leaf segments (6-8 days after application).

Compounds I.e.2, I.e.3, I.f.3, I.i.3, I.m.3, I.n.3, I.q.3, I.r.2, I.r.3, I.s.3, I.w.2, I.w.3, I.y.1, I.y.2, I.y.3, I.aa.3, I.ab.3, I.ac.3, I.ad.3, I.ae.3, I.ah.2, I.e.43, I.s.43, I.z.43, I.aa.43, I.ao.3, I.ao.43, I.ap.3, I.ap.43, I.aq.3, I.aq.43, I.ar.3, I.ar.43, I.as.43, I.at.3, I.at.43, I.au.3, I.au.43, I.av.43, I.ax.43, I.ay.3, I.bb.3, I.bb.43, I.be.3 at 200 ppm in the formulation give at least 80% disease control in this test when compared to untreated checks under the same conditions, which show extensive mycelial growth.

*Botryotinia fuckeliana* (*Botrytis cinerea*)/Liquid Culture (Gray Mould)

Conidia of the fungus from cryogenic storage are directly mixed into nutrient broth (Vogels broth). After placing a (DMSO) solution of test compound into a microtiter plate (96-well format), the nutrient broth containing the fungal spores is added. The test plates are incubated at 24° C. and the inhibition of growth is determined photometrically 3-4 days after application.

Compounds I.e.2, I.f.3, I.n.3, I.r.2, I.r.3, I.v.3, I.w.2, I.w.3, I.y.1, I.y.2, I.aa.3, I.ac.3, I.ag.3, I.ah.2, I.ah.3, I.s.43, I.aa.43, I.au.3, I.ax.3, I.ax.43, I.ay.3 at 200 ppm in the formulation give at least 80% disease control in this test when compared to untreated checks under the same conditions, which show extensive mycelial growth.

*Gaeumannomyces graminis*/Liquid Culture (Take-All of Cereals)

Mycelial fragments of the fungus from cryogenic storage were directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

Compounds I.a.3, I.b.3, I.c.3, I.d.3, I.e.2, I.e.3, I.f.3, I.g.3, I.h.3, I.i.3, I.j.3, I.k.3, I.m.3, I.n.3, I.o.3, I.p.3, I.q.3, I.r.2, I.r.3, I.s.3, I.t.3, I.u.3, I.v.3, I.w.2, I.w.3, I.x.3, I.y.1, I.y.2, I.y.3, I.aa.3, I.ab.3, I.ac.3, I.ad.3, I.ae.3, I.af.3, I.ag.3, I.ah.2, I.ah.3, I.ai.3, I.aj.3, I.ak.3, I.am.3 and I.an.3 at 200 ppm in the formulation give at least 80% disease control in this test when compared to untreated control leaf disks under the same conditions, which show extensive disease development.

*Glomerella lacenarium* (*Colletotrichum lacenarium*)/Liquid Culture (Anthracnose)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is measured photometrically 3 to 4 days after application.

Compounds I.a.3, I.b.3, I.c.3, I.e.2, I.e.3, I.f.3, I.h.3, I.i.3, I.k.3, I.m.3, I.n.3, I.p.3, I.q.3, I.r.2, I.r.3, I.s.3, I.t.3, I.u.3, I.v.3, I.w.2, I.w.3, I.x.3, I.y.1, I.y.2, I.y.3, I.aa.3, I.ab.3, I.ac.3, I.ad.3, I.ae.3, I.ag.3, I.ah.2, I.ah.3, I.e.43, I.s.43, I.z.43, I.aa.43, I.ao.3, I.ao.43, I.ap.3, I.ap.43, I.aq.3, I.aq.43, I.at.3, I.at.43, I.au.3, I.au.43, I.av.43, I.aw.3, I.ax.3, I.ax.43, I.ay.3, I.bb.3, I.bb.43, I.be.3, I.bf.3 at 200 ppm in the formulation give at least 80% disease control in this test when compared to untreated checks under the same conditions, which show extensive mycelial growth.

*Magnaporthe risea* (*Pyricularia oryzae*)/Rice/Leaf Disc Preventative (Rice Blast)

Rice leaf segments cv. Ballila are placed on agar in a multiwell plate (24-well format) and sprayed with the test compound formulated with DMSO and Tween20 and diluted in water. The leaf segments are inoculated with a spore suspension of the fungus 2 days after application. The inoculated leaf segments are incubated at 22° C. and 80% rh under a light regime of 24 h darkness followed by 12 h light/12 h darkness in a climate cabinet and the activity of a compound is assessed as percent disease control compared to untreated when an appropriate level of disease damage appears in untreated check leaf segments (5 to 7 days after application).

Compounds I.a.3, I.b.3, I.e.3, I.f.3, I.k.3, I.m.3, I.n.3, I.p.3, I.r.2, I.r.3, I.s.3, I.t.3, I.y.2, I.y.3, I.aa.3, I.ab.3, I.ac.3, I.ah.2, I.s.43, I.ao.3, I.ao.43, I.ap.3, I.ap.43, I.aq.3, I.ar.43, I.at.3, I.at.43, I.au.3, I.au.43, I.av.43, I.aw.3, I.ax.3, I.ax.43, I.ay.3, I.bb.3, I.bb.43 at 200 ppm in the formulation gives at least 80% disease control in this test when compared to untreated checks under the same conditions, which show extensive mycelial growth.

*Monocraphella nivalis* (*Microdochium nivale*)/Liquid Culture (Foot Rot Cereals)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

Compounds I.a.3, I.b.3, I.c.3, I.d.3, I.e.2, I.e.3, I.f.3, I.i.3, I.g.3, I.h.3, I.k.3, I.m.3, I.n.3, I.p.3, I.q.3, I.r.2, I.r.3, I.s.3, I.t.3, I.u.3, I.v.3, I.w.2, I.w.3, I.x.3, I.y.1, I.y.2, I.y.3, I.aa.3, I.ab.3, I.ac.3, I.ad.3, I.ae.3, I.ag.3, I.ah.2, I.ah.3, I.ai.3, I.aj.3, I.e.43, I.s.43, I.z.43, I.aa.43, I.ao.3, I.ao.43, I.ap.3, I.aq.3, I.at.3, I.au.3, I.au.43, I.av.43, I.aw.3, I.ax.3, I.ax.43, I.ay.3, I.bb.3, I.bb.43, I.bf.3 at 200 ppm in the formulation give at least 80% disease control in this test when compared to untreated checks under the same conditions, which show extensive mycelial growth.

*Mycosphaerella arachidis* (*Cercospora arachidicola*)/Liquid Culture (Early Leaf Spot)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4-5 days after application.

Compounds I.b.3, I.e.2, I.e.3, I.f.3, I.m.3, I.n.3, I.p.3, I.q.3, I.r.2, I.r.3, I.s.3, I.v.3, I.w.2, I.w.3, I.x.3, I.y.2, I.y.3, I.aa.3, I.ab.3, I.ac.3, I.ae.3, I.ah.3, I.s.43, I.z.43, I.ao.3, I.ao.43, I.ap.3, I.ap.43, I.aq.3, I.at.3, I.at.43, I.au.3, I.ax.3, I.ax.43, I.bb.3, I.bb.43 at 200 ppm in the formulation give at least 80% disease control in this test when compared to untreated checks under the same conditions, which show extensive mycelial growth.

*Mycosphaerella raminicola* (*Septoria tritici*)/Liquid Culture (*Septoria* blotch)

Conidia of the fungus from cryogenic storage are directly mixed into nutrient broth (PDB potato dextrose broth). After placing a (DMSO) solution of test compound into a microtiter plate (96-well format), the nutrient broth containing the fungal spores is added. The test plates are incubated at 24° C. and the inhibition of growth is determined photometrically 4 to 5 days after application.

Compounds I.a.3, I.b.3, I.c.3, I.e.2, I.e.3, I.f.3, I.h.3, I.k.3, I.m.3, I.n.3, I.p.3, I.q.3, I.r.2, I.r.3, I.s.3, I.t.3, I.u.3, I.v.3, I.w.2, I.w.3, I.x.3, I.y.1, I.y.2, I.y.3, I.aa.3, I.ab.3, I.ac.3, I.ad.3, I.ae.3, I.ag.3, I.ah.2, I.ah.3, I.ak.3, I.e.43, I.s.43, I.z.43, I.aa.43, I.ao.3, I.ao.43, I.ap.3, I.ap.43, I.aq.3, I.aq.43, I.ar.43, I.as.43, I.at.3, I.at.43, I.au.3, I.au.43, I.av.43, I.aw.3, I.ax.3, I.ax.43, I.bb.3, I.bb.43, I.be.3 at 200 ppm in the formulation give at least 80% disease control in this test when compared to untreated checks under the same conditions, which show extensive mycelial growth.

*Puccinia recondita* f. Sp. *Tritici*/Wheat/Leaf Disc Preventative (Brown Rust)

Wheat leaf segments cv. Kanzler are placed on agar in multiwell plates (24-well format) and sprayed with the formulated test compound diluted in water. The leaf disks are inoculated with a spore suspension of the fungus 1 day after application. The inoculated leaf segments are incubated at 19° C. and 75% rh under a light regime of 12 h light/12 h darkness in a climate cabinet and the activity of a compound is assessed as percent disease control compared to untreated when an appropriate level of disease damage appears in untreated check leaf segments (7-9 days after application).

Compounds I.a.3, I.b.3, I.c.3, I.e.2, I.e.3, I.f.3, I.i.3, I.m.3, I.n.3, I.p.3, I.r.2, I.r.3, I.s.3, I.t.3, I.w.2, I.w.3, I.y.1, I.y.2, I.y.3, I.aa.3, I.ab.3, I.ac.3, I.ad.3, I.ae.3, I.ah.2, I.e.43, I.s.43, I.z.43, I.aa.43, I.ao.3, I.ao.43, I.ap.3, I.ap.43, I.aq.3, I.aq.43, I.ar.43, I.as.43, I.at.3, I.at.43, I.au.3, I.au.43, I.av.43, I.aw.3, I.ax.3, I.ax.43, I.ba.43, I.bb.3, I.bb.43, I.bf.3 at 200 ppm in the formulation give at least 80% disease control in this test when compared to untreated checks under the same conditions, which show extensive mycelial growth.

*Pyrenophora teres*/Barley/Leaf Disc Preventative (Net Blotch)

Barley leaf segments cv. Hasso are placed on agar in a multiwell plate (24-well format) and sprayed with the test compound formulated with DMSO and Tween20 and diluted in water. The leaf segments are inoculated with a spore suspension of the fungus 2 days after application. The inoculated leaf segments are incubated at 20° C. and 65% rh under a light regime of 12 h light/12 h darkness in a climate cabinet and the activity of a compound is assessed as disease control compared to untreated when an appropriate level of disease damage appears in untreated check leaf segments (5 to 7 days after application).

Compounds I.b.3, I.e.2, I.e.3, I.h.3, I.r.2, I.r.3, I.s.3, I.t.3, I.w.2, I.w.3, I.y.1, I.y.2, I.aa.3, I.ab.3, I.ac.3, I.ad.3, I.ae.3, I.s.43, I.z.43, I.ao.3, I.ao.43, I.ap.3, I.aq.3, I.at.3, I.au.3, I.ay.3, I.bb.43 and I.be.3 at 200 ppm of the formulation give at least 80% disease control in this test when compared to untreated checks under the same conditions, which show extensive mycelial growth.

The invention claimed is:
1. A compound of formula (I):

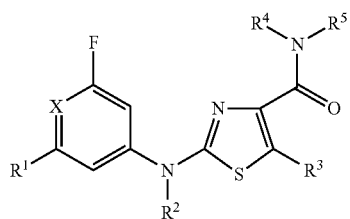

wherein,
$R^1$ is halogen, cyano, $C_1$-$C_6$alkyl or $C_1$-$C_6$alkoxy, wherein $C_1$-$C_6$alkyl and $C_1$-$C_6$alkoxy are optionally substituted with 1 to 3 groups represented by $R^6$;
$R^2$ and $R^4$ are independently hydrogen, $C_1$-$C_6$alkyl, $C_1$-$C_6$alkoxy or $C_3$-$C_6$cycloalkyl,
wherein $C_1$-$C_6$alkyl, $C_1$-$C_6$alkoxy and $C_3$-$C_6$cycloalkyl are optionally substituted with 1 to 3 groups represented by $R^6$;
$R^3$ is halogen, $C_1$-$C_6$alkyl, $C_1$-$C_6$alkoxy or $C_3$-$C_6$cycloalkyl, wherein $C_1$-$C_6$alkyl, $C_1$-$C_6$alkoxy and $C_3$-$C_6$cycloalkyl are optionally substituted with 1 to 3 groups represented by $R^6$;
$R^5$ is $C_1$-$C_{10}$alkyl, $C_3$-$C_{10}$cycloalkyl, $C_3$-$C_{10}$cycloalkenyl, $C_3$-$C_{10}$cycloalkyl$C_1$-$C_2$alkyl, $C_2$-$C_{10}$alkenyl, $C_2$-$C_{10}$alkynyl, aryl, heteroaryl wherein the heteroaryl is a 5- or 6-membered aromatic monocyclic ring comprising 1, 2, 3 or 4 heteroatoms individually selected from nitrogen, oxygen and sulfur, heterocyclyl wherein the heterocyclyl is a 4-, 5- or 6-membered non-aromatic monocyclic ring comprising 1, 2 or 3 heteroatoms individually selected from nitrogen, oxygen and sulfur, heterocyclyl$C_1$-$C_2$alkyl, or a 5- to 10-membered non-aromatic annulated or spirocyclic carbobicyclyl ring system optionally comprising 1, 2, 3, 4 or 5 heteroatoms individually selected from nitrogen, oxygen and sulfur, and optionally bonded to the rest of the molecule through a $C_1$-$C_2$alkylene linker;
wherein any of said $C_1$-$C_{10}$alkyl, $C_3$-$C_{10}$cycloalkyl, $C_1$-$C_{10}$cycloalkenyl, $C_2$-$C_{10}$alkenyl and $C_2$-$C_{10}$alkynyl moieties are optionally substituted with 1 to 4 groups represented by $R^7$ or 1 group represented by $R^8$; or
wherein any of said aryl, heteroaryl and heterocyclyl moieties are optionally substituted with 1 to 3 groups represented by $R^9$ or 1 group represented by $R^{10}$, or are optionally substituted with 1 or 2 groups represented by $R^9$ and 1 group represented by $R^{10}$; or
wherein the annulated or spirocyclic carbobicyclyl ring system is optionally substituted with 1 to 3 groups represented by $R^7$, or the annulated carbobicyclyl ring system is optionally substituted by $C_3$-$C_6$cycloalkyl to form a spirocyclyl moiety,
$R^6$ is independently selected from halogen, cyano, hydroxyl, $C_1$-$C_6$alkoxy, and $C_3$-$C_6$cycloalkyl;
$R^7$ is independently selected from halogen, cyano, hydroxyl, $C_1$-$C_6$alkyl, $C_1$-$C_6$haloalkyl, $C_1$-$C_6$alkoxy, $C_1$-$C_6$alkoxy$C_1$-$C_6$alkyl, $C_3$-$C_6$cycloalkyl, $C_3$-$C_6$cycloalkyl$C_{1-2}$alkyl, $C_2$-$C_6$acyl, $C_2$-$C_6$acyloxy, $C_2$-$C_6$acyloxy$C_1$-$C_6$alkyl and $C_1$-$C_4$alkoxycarbonyl;
wherein when $R^7$ is $C_3$-$C_6$cycloalkyl$C_{1-2}$alkyl, the $C_3$-$C_6$cycloalkyl moiety is optionally substituted with 1 or 2 groups independently selected from halogen and $C_1$-$C_6$alkyl;
$R^8$ is aryl, aryloxy, aryl$C_1$-$C_6$alkyl, heteroaryl wherein the heteroaryl is a 5- or 6-membered aromatic monocyclic ring comprising 1, 2, 3 or 4 heteroatoms individually selected from nitrogen, oxygen and sulfur, heteroaryloxy or heteroaryl$C_1$-$C_6$alkyl, wherein aryl and heteroaryl are optionally substituted with 1 to 3 groups represented by $R^9$ or 1 group represented by $R^{10}$;
$R^9$ is independently selected from halogen, cyano, hydroxyl, $C_1$-$C_6$alkyl, $C_1$-$C_6$alkoxy, $C_1$-$C_6$alkylthio, $C_2$-$C_6$alkenyl, $C_2$-$C_6$alkenyloxy, $C_2$-$C_6$alkynyl, $C_2$-$C_6$alkynyloxy,
wherein $C_1$-$C_6$alkyl, $C_1$-$C_6$alkoxy, $C_1$-$C_6$alkylthio, $C_2$-$C_6$alkenyl, $C_2$-$C_6$alkenyloxy, $C_2$-$C_6$alkynyl, $C_2$-$C_6$alkynyloxy, are optionally substituted with 1 to 3 groups represented by $R^{11}$;
$R^{10}$ is selected from $C_3$-$C_6$cycloalkyl, $C_3$-$C_8$cycloalkoxy, $C_3$-$C_6$cycloalkylthio, aryl, aryloxy, arylthio, aryl$C_1$-$C_6$alkyl, heteroaryl wherein the heteroaryl is a 5- or 6-membered aromatic monocyclic ring comprising 1, 2, 3 or 4 heteroatoms individually selected from nitrogen, oxygen and sulfur, heteroaryloxy, heteroarylthio, heteroaryl$C_1$-$C_6$alkyl, heterocyclyl wherein the heterocyclyl is a 4-, 5- or 6-membered non-aromatic monocyclic ring comprising 1, 2 or 3 heteroatoms individually selected from nitrogen, oxygen and sulfur, heterocyclyloxy, heterocyclylthio or heterocyclyl$C_1$-$C_6$alkyl, wherein $C_3$-$C_6$cycloalkyl, $C_3$-$C_8$cycloalkoxy, $C_3$-$C_6$cycloalkylthio, aryl, aryloxy, arylthio, aryl$C_1$-$C_6$alkyl, heteroaryl, heteroaryloxy, heteroarylthio, heteroaryl$C_1$-$C_6$alkyl, heterocyclyl, heterocyclyloxy, heterocyclylthio and heterocyclyl$C_1$-$C_6$alkyl are optionally substituted with 1 to 3 groups represented by $R^{11}$;

$R^{11}$ is independently selected from halogen and methyl;

X is N;

or a salt or an N-oxide thereof.

2. The compound according to claim 1, wherein $R^1$ is halogen, cyano, methyl, trifluoromethyl, methoxy or trifluoromethoxy.

3. The compound according to claim 1, wherein $R^2$ is hydrogen.

4. The compound according to claim 1, wherein $R^3$ is halogen or $C_1$-$C_4$alkyl.

5. The compound according to claim 1, wherein $R^4$ is hydrogen.

6. The compound according to claim 1, wherein:

$R^5$ is $C_1$-$C_7$alkyl, $C_3$-$C_6$cycloalkyl, $C_3$-$C_6$cycloalkyl$C_1$-$C_2$alkyl, $C_3$-$C_6$cycloalkenyl, $C_2$-$C_6$alkenyl, $C_2$-$C_7$alkynyl, phenyl, heteroaryl wherein the heteroaryl is a 5- or 6-membered aromatic monocyclic ring comprising 1, 2, 3 or 4 heteroatoms individually selected from nitrogen, oxygen and sulfur, heterocyclyl wherein the heterocyclyl is a 4-, 5- or 6-membered non-aromatic monocyclic ring comprising 1, 2 or 3 heteroatoms individually selected from nitrogen, oxygen and sulfur, heterocyclyl$C_1$-$C_2$alkyl, or a 5- to 10-membered non-aromatic annulated or spirocyclic carbobicyclyl ring system optionally comprising 1, 2 or 3 heteroatoms individually selected from nitrogen, oxygen and sulfur, and optionally bonded to the rest of the molecule through a $C_1$-$C_2$alkylene linker;

wherein any of said $C_1$-$C_7$alkyl, $C_3$-$C_6$cycloalkyl, $C_3$-$C_6$cycloalkenyl, $C_2$-$C_6$alkenyl and $C_2$-$C_7$alkynyl moieties are optionally substituted with 1 to 4 groups represented by $R^7$ or 1 group represented by $R^8$; or wherein any of said phenyl, heteroaryl and heterocyclyl moieties are optionally substituted with 1 to 3 groups represented by $R^9$ or 1 group represented by $R^{10}$, or are optionally substituted with 1 or 2 groups represented by $R^9$ and 1 group represented by $R^{10}$; or wherein the annulated or spirocyclic carbobicyclyl ring is optionally substituted with 1 to 3 groups represented by $R^7$, or the annulated carbobicyclyl ring system is optionally substituted by $C_3$-$C_6$cycloalkyl to form a spirocyclyl moiety.

7. The compound according to claim 1, wherein:

$R^5$ is $C_1$-$C_6$alkyl, $C_3$-$C_6$cycloalkyl, $C_3$-$C_5$cycloalkyl$C_{1-2}$alkyl, $C_2$-$C_6$alkynyl, phenyl, heterocyclyl, wherein the heterocyclyl is a 4- or 6-membered non-aromatic monocyclic ring comprising 1 oxygen atom, heterocyclyl$C_1$alkyl, or a 5- to 9-membered non-aromatic annulated or spirocyclic carbobicyclyl ring system optionally comprising 1 oxygen atom, and optionally bonded to the rest of the molecule through a methylene linker;

wherein any of said $C_1$-$C_6$alkyl, $C_3$-$C_6$cycloalkyl and $C_2$-$C_6$alkynyl, moieties are optionally substituted with 1 to 4 groups represented by $R^7$ or 1 group represented by $R^8$; or wherein any of said phenyl or heterocyclyl moieties are optionally substituted with 1 or 2 groups represented by $R^9$ or 1 group represented by $R^{10}$, or are optionally substituted with 1 or 2 groups represented by $R^9$ and 1 group represented by $R^{10}$; or wherein the annulated or spirocyclic carbobicyclyl ring system is optionally substituted with 1 or 2 groups represented by $R^7$, or the annulated carbobicyclyl ring system is optionally substituted by $C_4$-$C_5$cycloalkyl to form a spirocycle.

8. The compound according to claim 1, wherein:

$R^5$ is $C_1$-$C_6$alkyl, $C_2$-$C_6$alkynyl, $C_3$-$C_6$cycloalkyl or $C_3$-$C_6$cycloalkyl$C_1$-$C_2$alkyl, wherein any of the $C_1$-$C_6$alkyl, $C_2$-$C_6$alkynyl and $C_3$-$C_6$cycloalkyl moieties are optionally substituted with 1 to 4 groups represented by $R^7$ or 1 group represented by $R^8$, wherein $R^7$ is independently selected from halogen, cyano, hydroxyl, $C_1$-$C_6$alkyl, $C_1$-$C_6$haloalkyl, $C_1$-$C_4$alkoxy, $C_1$-$C_4$alkoxy$C_1$-$C_4$alkyl, $C_3$-$C_6$cycloalkyl, $C_3$-$C_6$cycloalkyl$C_{1-2}$alkyl, and $C_1$-$C_3$alkoxycarbonyl, and $R^8$ is phenyl, benzyl or isoxazole optionally substituted with 1 to 3 groups represented by $R^9$ or 1 group represented by $R^{10}$, and wherein $R^9$ is halogen and $R^{10}$ is phenyl optionally substituted by 1 to 3 groups represented by $R^{11}$ which is halogen;

or $R^5$ is phenyl, oxetanyl, tetrahydrofuranyl or tetrahydropyranyl each optionally substituted with 1 to 3 groups represented by $R^9$ or 1 group represented by $R^{10}$, or 1 or 2 groups represented by $R^9$ and 1 group represented by $R^{10}$, wherein $R^9$ is independently selected from halogen and $C_1$-$C_4$alkyl, and $R^{10}$ is selected from phenyl, benzyl or $C_6$-$C_8$cycloalkoxy each optionally substituted by 1 to 3 groups represented by $R^{11}$;

or $R^5$ is an annulated or spirocyclic ring system selected from:

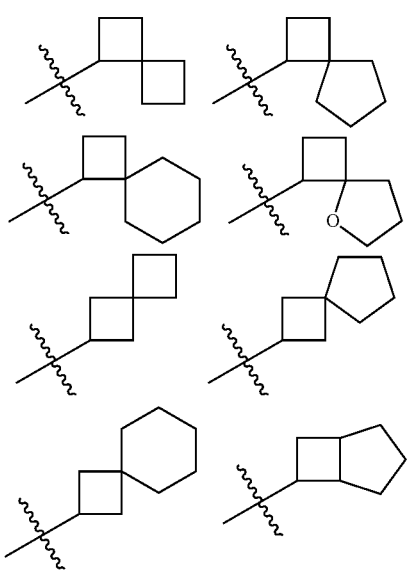

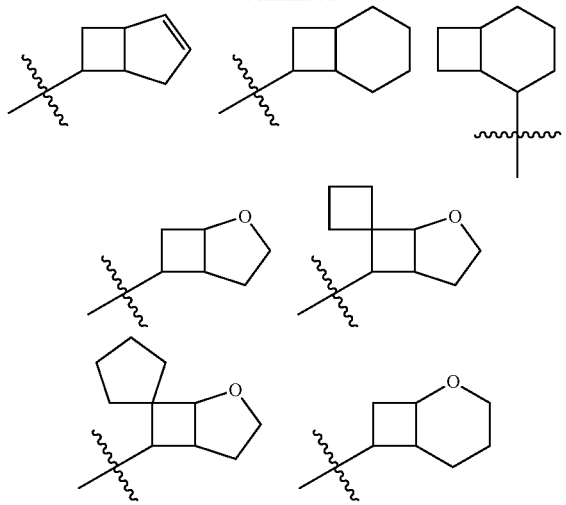

each optionally substituted by 1 to 3 groups represented by $R^7$ independently selected from $C_1$-$C_4$alkyl and $C_2$-$C_4$acyloxy$C_1$-$C_4$alkyl.

9. The compound according to claim 1, wherein:

$R^5$ is $C_1$-$C_4$alkyl optionally substituted by 1 group represented by $R^7$ selected from $C_3$-$C_6$cycloalkyl; or $R^5$ is an annulated or spirocyclic ring system selected from:

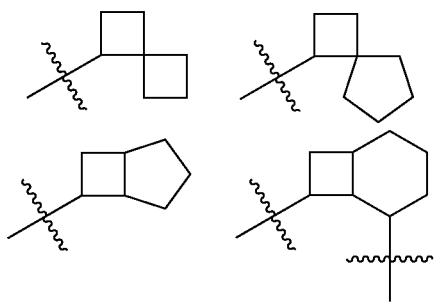

each optionally substituted by 1 to 3 groups represented by $R^5$ independently selected from $C_1$-$C_4$alkyl.

10. The compound according to claim 9, wherein $R^5$ is an annulated or spirocyclic ring system substituted by 1 to 3 groups represented by $R^7$, and $R^7$ is methyl.

11. An agrochemical composition comprising a fungicidally effective amount of a compound of formula (I) according to claim 1.

12. The composition according to claim 11, further comprising at least one additional active ingredient and/or an agrochemically-acceptable diluent or carrier.

13. A method of controlling or preventing infestation of useful plants by phytopathogenic microorganisms, wherein a fungicidally effective amount of a compound of formula (I) according to claim 1, or a composition comprising this compound as active ingredient, is applied to the plants, to parts thereof or the locus thereof.

14. The compound according to claim 1, $R^5$ is substituted by $R^7$ or 1 group represented by $R^8$.

15. The compound according to claim 14, wherein $R^S$ is $C_1$-$C_{10}$alkyl, $C_3$-$C_{10}$cycloalkyl, $C_3$-$C_{10}$cycloalkenyl, $C_3$-$C_{10}$cycloalkyl$C_1$-$C_2$alkyl, $C_2$-$C_{10}$alkenyl, or $C_2$-$C_{10}$alkynyl.

16. The compound according to claim 15, wherein $R^1$ is halogen.

17. The compound according to claim 16, wherein $R^5$ is cyclobutyl.

18. The compound according to claim 1, $R^5$ is an annulated or spirocyclic ring system selected from:

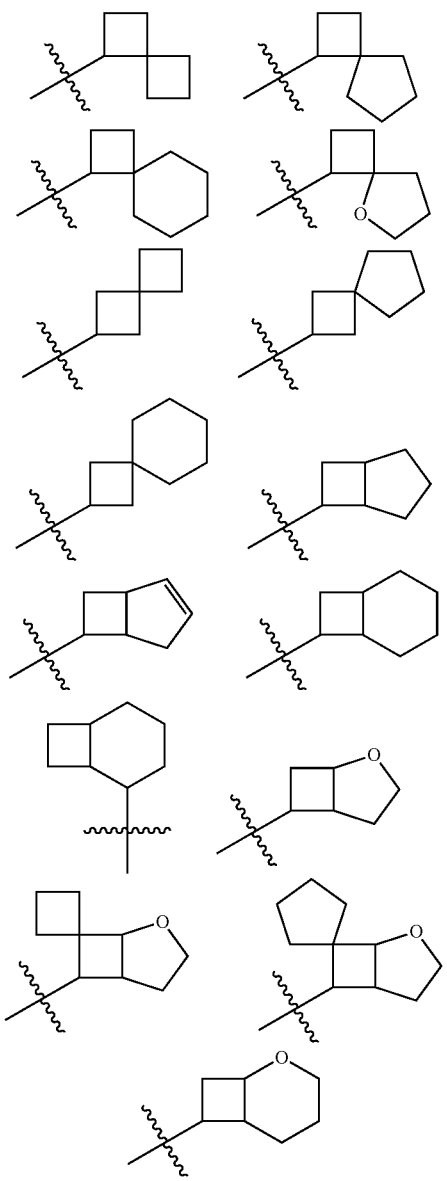

each optionally substituted by 1 to 3 groups represented by $R^7$ independently selected from $C_1$-$C_4$alkyl and $C_2$-$C_4$acyloxy$C_1$-$C_4$alkyl.

19. The compound according to claim 1, wherein $R^4$ is $C_1$-$C_6$alkyl, $C_1$-$C_6$alkoxy or $C_3$-$C_6$cycloalkyl, wherein $C_1$-$C_6$alkyl, $C_1$-$C_6$alkoxy and $C_3$-$C_6$cycloalkyl are optionally substituted with 1 to 3 groups represented by $R^6$.

* * * * *